United States Patent
Adam et al.

(10) Patent No.: US 6,610,747 B2
(45) Date of Patent: Aug. 26, 2003

(54) PHENOXYBENZYLAMINE DERIVATIVES AS SSRIS

(75) Inventors: Mavis Diane Adam, Niantic, CT (US); Mark David Andrews, County of Kent (GB); Mark Leonard Elliott, Canterbury, CT (US); Geoffrey Edward Gymer, County of Kent (GB); David Hepworth, County of Kent (GB); Harry Ralph Howard, Jr., Bristol, CT (US); Donald Stuart Middleton, County of Kent (GB); Alan Stobie, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/941,177

(22) Filed: Aug. 27, 2001

(65) Prior Publication Data

US 2003/0060456 A1 Mar. 27, 2003

Related U.S. Application Data

(60) Provisional application No. 60/292,400, filed on May 21, 2001, and provisional application No. 60/240,271, filed on Oct. 13, 2000.

(30) Foreign Application Priority Data

Aug. 31, 2000 (GB) ................................ 0021593
Mar. 21, 2001 (GB) ................................ 0107116

(51) Int. Cl.⁷ ........................ A61K 31/18; C07C 311/15
(52) U.S. Cl. ................... 514/603; 564/86; 564/99; 564/162; 564/336; 562/432; 560/17; 560/24; 560/25; 560/27; 560/157; 514/478; 514/544; 514/568; 514/605; 514/617
(58) Field of Search ............... 564/86, 99, 162, 564/336; 562/432; 514/478, 594, 568, 603, 617, 605; 560/17, 24, 25, 27, 157

(56) References Cited

U.S. PATENT DOCUMENTS

| | | | |
|---|---|---|---|
| 4,161,529 A | 7/1979 | Beregi et al. | 424/274 |
| 5,190,965 A | 3/1993 | Ruigt et al. | 514/401 |
| 5,430,063 A | 7/1995 | Ruigt et al. | 514/650 |
| 5,691,373 A | 11/1997 | Berryman et al. | 514/464 |

FOREIGN PATENT DOCUMENTS

| | | | |
|---|---|---|---|
| EP | 0394043 | 4/1990 | |
| EP | 0402097 | 6/1990 | |
| EP | 0516234 | 5/1992 | C07C/217/58 |
| WO | WO9623783 | 8/1996 | |
| WO | WO9637204 | 11/1996 | |
| WO | WO9717325 | 5/1997 | |
| WO | WO9947497 | 9/1999 | C07C/315/00 |
| WO | WO0050380 | 8/2000 | |
| WO | WO0127068 | 4/2001 | |
| WO | WO0172687 | 4/2001 | C07C/217/58 |

Primary Examiner—C. S. Aulakh
(74) Attorney, Agent, or Firm—Peter C. Richardson; Gregg C. Benson; A. Dean Olson

(57) ABSTRACT

A compound of general formula (I) wherein $R^1$ and $R^2$ are H, $C_1$–$C_6$alkyl or $(CH_2)_d(C_3$–$C_6$cycloalkyl) wherein d=0, 1, 2 or 3; or $R^1$ and $R^2$ together with the nitrogen to which they are attached form an azetidine ring; Z or Y is —$SR^3$ and the other Z or Y is halogen or —$R^3$; wherein $R^3$ is $C_1$–$C_4$ alkyl optionally substituted with fluorine; except that $R^3$ is not $CF_3$; or Z and Y are linked so that, together with the interconnecting atoms, Z and Y form a fused 5 to 7-membered carbocyclic or heterocyclic ring, and wherein when Z and Y form a heterocyclic ring, in addition to carbon atoms, the linkage contains one or two heteroatoms independently selected from oxygen, sulfur and nitrogen; $R^4$ and $R^5$, which may be the same or different, are: A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; or a 5- or 6-membered heterocyclic ring containing 1, 2 or 3 heteroatoms selected from N, S and O, optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)$_2$.

(I)

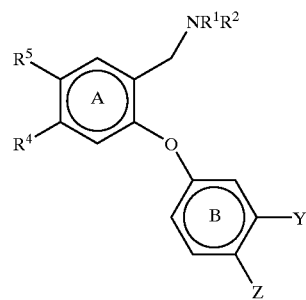

39 Claims, No Drawings

PHENOXYBENZYLAMINE DERIVATIVES AS SSRIS

This application claims priority from co-pending U.S. Provisional Application Number 60/240,271 filed Oct. 13, 2000 and U.S. Provisional Application No. 60/292,400 filed May 21, 2001 and United Kingdom Application Number 0021593.9 filed Aug. 31, 2000 and United Kingdom Application Number 0107116.6 filed Mar. 21, 2001.

This invention relates to novel diphenyl ether compounds which inhibit monoamine re-uptake. In particular compounds of the present invention exhibit activity as selective serotonin re-uptake inhibitors (SSRIs) and have utility therefore in a variety of therapeutic areas. Notably the compounds of the present invention are useful in the treatment or prevention of a variety of disorders, including those in which the regulation of monoamine transporter function is implicated, such as depression, attention deficit hyperactivity disorder, obsessive-compulsive disorder, post-traumatic stress disorder, substance abuse disorders and sexual dysfunction including premature ejaculation, and to pharmaceutical formulations containing such compounds.

According to a first aspect, the invention provides a compound of general formula (I), pharmaceutically acceptable salts, solvates or polymorphs thereof;

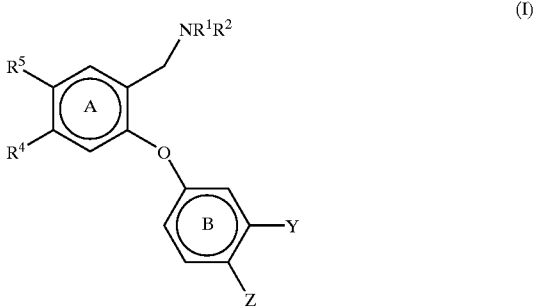

wherein;

$R^1$ and $R^2$, which may be the same or different, are H, $C_1$–$C_6$alkyl or $(CH_2)_d(C_3$–$C_6$cycloalkyl) wherein d=0, 1, 2 or 3; or $R^1$ and $R^2$ together with the nitrogen to which they are attached form an azetidine ring;

Z or Y is —$SR^3$ and the other Z or Y is halogen or —$R^3$; wherein $R^3$ is independently $C_1$–$C_4$ alkyl optionally substituted with fluorine; except that $R^3$ is not $CF_3$;

or Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen; with the proviso that when $R^5$ is fluorine and $R^2$ is methyl then the fused ring is not 1,3-dioxolane and Z and Y together do not form a fused phenyl ring;

$R^4$ and $R^5$, which may be the same or different, are:

A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$ alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F (preferably up to 3), OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and O optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)_2$.

Unless otherwise indicated, any alkyl group may be straight or branched and is of 1 to 6 carbon atoms, preferably 1 to 4 and particularly 1 to 3 carbon atoms.

Unless otherwise indicated, any carbocyclyl group contains 3 to 8 ring-atoms, and may be saturated, unsaturated or aromatic. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocyclic should be similarly construed. In addition, the term carbocyclyl includes any fused combination of carbocyclyl groups, for example naphthyl, phenanthryl, indanyl and indenyl.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Halo means fluoro, chloro, bromo or iodo.

Preferably $R^1$ and $R^2$, which may be the same or different, are hydrogen or $C_1$–$C_6$alkyl. More preferably hydrogen or methyl.

When Z or Y is —$SR^3$, $R^3$ is preferably methyl or ethyl.

When Z and Y form a fused ring, the ring is preferably a heterocyclic ring. More preferably, the linkage contains one or two sulfur atoms.

Preferably $R^4$ and $R^5$ are not both hydrogen.

Preferably $R^4$ and $R^5$, which may be the same or different, are

—$(CH_2)_p$—X, where p is 0, 1 or 2 (preferably 0 or 1); X is hydrogen, hydroxy, $CONR^6R^7$, $SO_2NR^6R^7$, $NR^8SO_2R^9$, $SR^{10}$, $SOR^9$ or $SO_2R^{10}$ wherein $R^6$, $R^7$, $R^8$, $R^9$ and $R^{10}$ are as defined in the first aspect, or a 5- or 6-membered heterocyclic ring containing 1, 2 or 3 heteroatoms selected from N, S and O (preferably oxadiazolyl, triazolyl, imidazolyl, oxazolyl, pyrazolyl, pyridinyl or pyrimidinyl).

More preferably $R^4$ and $R^5$, which may be the same or different, are:

—$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen or $C_1$–$C_3$alkyl optionally substituted by hydroxy, —$CONH_2$ or $C_1$–$C_3$alkoxy (preferably methoxy); $R^8$ is hydrogen, hydroxyethyl or methyl; or $R^9$ is methyl, ethyl, isopropyl, trifluoromethyl or methoxyethyl; or triazolyl, imidazolyl or pyrazolyl.

More preferably still $R^4$ is hydrogen.

Preferably $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy). More preferably $R^6$ and $R^7$, which may be the same or different, are hydrogen or methyl, more preferably still hydrogen.

When present, $R^{12}$ is preferably oxadiazolyl, triazolyl, imidazolyl, oxazolyl, pyrazolyl, pyridinyl or pyrimidinyl. More preferably triazolyl, imidazolyl or pyrazolyl.

In the case where $R^6$ and $R^7$, together with the nitrogen to which they are attached, form a heterocyclic ring, preferred rings are pyrrolidine or piperidine rings each of which may be substituted by OH or $CONH_2$ or a morpholine ring which may be substituted by $CONH_2$.

Preferably $R^{11}$ is hydrogen or $C_{1-6}$ alkyl.

Preferably $R^8$ is hydrogen, hydroxyethyl or methyl. More preferably hydrogen.

Preferably $R^9$ is methyl, ethyl, isopropyl, trifluoromethyl or methoxyethyl. More preferably methyl or ethyl (preferably methyl).

Preferably $R^{10}$ is methyl or ethyl.

Preferably p is 1 or 0, more preferably 0.

Preferably $R^1$ and $R^2$, which may be the same or different, are hydrogen or methyl;

when present, $R^3$ is methyl or ethyl; or Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen; and $R^4$ and $R^5$, which may be the same or different, are $(CH_2)_p$—X, where p is 0 or 1; X is hydrogen, hydroxy, $CONR^6R^7$, $SO_2NR^6R^7$, $NR^8SO_2R^9$, $SR^{10}$, $SOR^9$ or $SO_2R^{10}$ and wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); or $R^6$ and $R^7$, together with the nitrogen to which they are attached, may form a morpholine, pyrrolidine or piperidine ring each of which may be substituted by OH or $CONH_2$; $R^8$ is hydrogen, hydroxyethyl or methyl (preferably hydrogen); $R^9$ is methyl, ethyl, isopropyl, trifluoromethyl or methoxyethyl; and $R^{10}$ is methyl or ethyl; or an oxadiazolyl, triazolyl, imidazolyl, oxazolyl, pyrazolyl, pyridinyl or pyrimidinyl group.

More preferably $R^1$ and $R^2$, which may be the same or different, are hydrogen or methyl;

when present, $R^3$ is methyl or ethyl; or Z and Y are linked so that, together with the interconnecting atoms, Z and Y form a fused 5 to 7-membered heterocyclic ring containing 1 or 2 sulfur atoms; and $R^4$ and $R^5$, which may be the same or different, are —$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); $R^8$ is hydrogen, hydroxyethyl or methyl; $R^9$ is methyl, ethyl, isopropyl, trifluoromethyl or methoxyethyl; or triazolyl, imidazolyl or pyrazolyl.

More preferably still $R^1$ and $R^2$, which may be the same or different, are hydrogen or methyl;

when present $R^3$ is methyl or ethyl; or Z and Y are linked so that, together with the interconnecting atoms, Z and Y form a fused saturated 5 to 7-membered heterocyclic ring containing 1 or 2 sulfur atoms;

$R^4$ is hydrogen, and $R^5$ is

—$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); $R^8$ is hydrogen, hydroxyethyl or methyl; $R^9$ is methyl, ethyl, isopropyl, trifluoromethyl or methoxyethyl; or triazolyl, imidazolyl or pyrazolyl.

More preferably still $R^4$ and $R^5$ are not both hydrogen.

Preferred compounds are:

4-(2,3-dihydro-1-benzothien-5-yloxy)-3-[(methylamino)methyl]-benzenesulfonamide (Example 2);

3-[(dimethylamino)methyl]-4-[3-methyl-4-(methylsulfanyl)phenoxy]-benzenesulfonamide (Example 12);

4-(2,3-dihydro-1-benzothien-5-yloxy)-3-[(dimethylamino)methyl]-benzenesulfonamide (Example 16);

4-[3-chloro-4-(methylsulfanyl)phenoxy]-3-[(dimethylamino)methyl]-benzenesulfonamide (Example 17);

3-[(dimethylamino)methyl]-4-[3-fluoro-4-(methylsulfanyl)phenoxy]-benzenesulfonamide (Example 18);

N,N-dimethyl-N-[2-(6-quinolinyloxy)benzyl]amine (Example 29);

3-[(methylamino)methyl]-4-(6-quinolinyloxy)benzenesulfonamide (Example 35);

4-(2,3-dihydro-1-benzothien-5-yloxy)-3-[(methylamino)methyl]benzamide (Example 60);

4-(2,3-dihydro-1-benzothien-5-yloxy)-N-methyl-3-[(methylamino)methyl]-benzamide (Example 62);

N-{3-[(methylamino)methyl]-4-[3-methyl-4-(methylsulfanyl)phenoxy]benzyl}methanesulfonamide (Example 75);

3-[(methylamino)methyl]-4-[3-methyl-4-(methylsulfanyl)phenoxy]benzamide (Example 79);

4-(2,3-dihydro-1,4-benzoxathiin-7-yloxy)-3-[(dimethylamino)methyl]benzamide (Example 88);

{3-[(dimethylamino)methyl]-4-[3-fluoro-4-(methylsulfanyl)phenoxy]phenyl}-methanol (Example 90);

3-[(dimethylamino)methyl]-4-(6-quinolinyloxy)benzamide (Example 100);

3-[(methylamino)methyl]-4-(6-quinolinyloxy)benzamide (Example 102);

N-methyl-N-{3-[(methylamino)methyl]-4-[3-methyl-4-(methylsulfanyl)phenoxy]-phenyl}methanesulfonamide (Example 116) and N-{4-(2,3-dihydro-1,4-benzoxathiin-7-yloxy)-3-[(dimethylamino)methyl]phenyl}-methanesulfonamide (Example 124).

According to a second aspect the invention provides compound of formula (I) or (XIX)

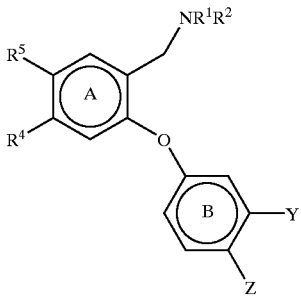
(I)

and pharmaceutically acceptable salts or solvates thereof wherein (in this aspect): $R^1$ and $R^2$ independently represent H, $C_1$–$C_6$ alkyl or $(CH_2)_d(C_3$–$C_6$cycloalkyl) wherein d=0, 1, 2 or 3, or wherein $NR^1R^2$ when taken together represent a 4-membered ring wherein $R^1$ and $R^2$ together represent $C_3$ alkyl; Z and Y both independently represent —$SR^3$ wherein, when Z=—$SR^3$ then Y=halogen, —$OR^a$, —$R^a$ or —$SR^a$; or when Y=—$SR^3$ then Z=halogen, —$OR^a$, $R^a$ or —$SR^a$; and $R^3$ and $R^a$ independently represent: $C_1$–$C_4$ alkyl (optionally substituted with fluorine atoms e.g. —$CF_3$); or Z and Y when taken together can represent a fused 5 to 7 membered ring as illustrated by general formula XIX, wherein said 5 to 7 membered ring may be saturated, unsaturated or aromatic, and wherein said 5 to 7 membered ring may optionally contain one or more heteroatoms P and Q, wherein P and Q=may be independently O, S or N, and wherein E, F, or G independently represent CH or $CH_2$ and wherein k and p may independently be=0, 1, 2 or 3, and m=1, 2 or 3; and

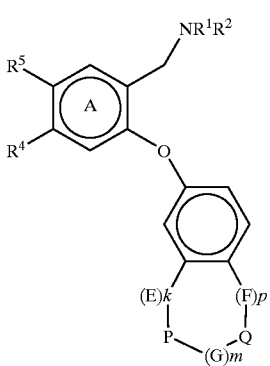
(XIX)

$R^4$ and $R^5$ independently represent A—X wherein A=—$(CH_2)_n$—, wherein n represents 0, 1 or 2 and wherein X represents: H, F, Cl, Br, I, $CONR^6R^7$ or $SO_2NR^6R^7$, OH, $NR^8SO_2R^9$, $NO_2$, $NR^6R^{11}$, CN, $CO_2R^{10}$, CHO, $S(O)_mR^{10}$ wherein m=0, 1 or 2 and wherein $R^6$, $R^7$, $R^8$ and $R^{10}$ independently represent H or $C_{1-6}$ alkyl, wherein $R^9$ represents $C_{1-6}$ alkyl, $R^{11}$ represents H, $C_{1-6}$ alkyl, $C(O)R^6$, $CO_2R^9$, $C(O)NHR^6$ or $SO_2NR^6R^6$ and wherein said $C_{1-6}$ alkyl group is optionally substituted by one or more groups selected from OH, $CO_2H$, $C_{3-6}$ cycloalkyl, $NH_2$, $CONH_2$, $C_{1-6}$ alkoxy, $C_{1-6}$ alkoxycarbonyl and a 5- or 6-membered heterocyclic ring containing 1, 2 or 3 heteroatoms selected from N, S and O; or with the proviso that when P=Q=oxygen then both k and p are not zero; with the proviso that Z and Y together do not form a fused phenyl ring; $R^4$ or $R^5$ may be representative of a 5- or 6-membered heterocyclic ring containing 1, 2 or 3 heteroatoms selected from N, S and O; and in addition, $R^6$ and $R^7$ may, together with the N atom to which they are attached, represent a 5- or 6-membered heterocyclic ring which may be optionally substituted; and pharmaceutically acceptable salts or solvates thereof with the proviso that both $R^4$ and $R^5$ are not H.

For the avoidance of doubt, unless otherwise indicated, the term substituted means substituted by one or more defined groups. In the case where groups may be selected from a number of alternatives groups, the selected groups may be the same or different.

For the avoidance of doubt, the term independently means that where more than one substituent is selected from a number of possible substituents, those substituents may be the same or different.

According to a third aspect, the invention provides a compound of general formula I and pharmaceutically acceptable salts thereof, wherein $R^1$, $R^2$, $R^3$, Z and Y are as defined in the first aspect; and $R^4$ and $R^5$, which may be the same or different, are —$(CH_2)_p$—A', wherein p is 0, 1 or 2 and A' is a polar group. In this aspect, polar groups may be defined as those having a negative π-value (see C Hansch and A Leo, 'Substituent Constants for Correlation Analysis in Chemistry and Biology', Wiley, N.Y., 1979). In this system, H has a π-value of 0.00, —$OCH_3$ has a π-value of –0.02, and —$SO_2NH_2$ has a π-value of –1.82, for example [see Table VI-I, 'Well-Characterized Aromatic Substituents', p 49, ibid]. More preferred polar groups have a more negative π-value: thus, preferred groups have π-values of a greater negative value than –0.1, more preferably a greater negative value than –0.5, and most preferably a greater negative value than –1.0. Even when p is other than zero in the above definition, the definition of A' is based on the above reference as if p was zero.

Unless otherwise specified, the compounds of the first, second and third aspects are hereinafter defined as compounds of the invention.

The compounds of the invention have the advantage that they are selective inhibitors of the re-uptake of serotonin (SRIs) (and so are likely to have reduced side effects), they have a rapid onset of action (making them suitable for administration shortly before an effect is required), they have desirable potency and associated properties. Compounds that selectively inhibit the re-uptake of serotonin, but not noradrenaline or dopamine, are preferred.

We have found that compounds of formula I which possess these properties have a relatively polar group at $R^4/R^5$.

The pharmaceutically or veterinarily acceptable salts of the compounds of formula I which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc, diolamine, olamine, ethylenediamine, tromethamine, chloine, megulamine and diethanolamine salts. For reviews on suitable pharmaceutical salts see Berge et al, J. Pharm, Sci., 66, 1–19, 1977; P L Gould, International Journal of Pharmaceutics, 33 (1986), 201–217; and Bighley et al, Encyclopedia of Pharmaceutical Technology, Marcel Dekker Inc, New York 1996, Volume 13, page 453–497.

Hereinafter, the compounds, their pharmaceutically acceptable salts, their solvates and polymorphs, defined in any aspect of the invention (except intermediate compounds in chemical processes) are referred to as "compounds of the invention".

The pharmaceutically acceptable solvates of the compounds of the invention include the hydrates thereof.

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers, the invention includes individual isomers as well as mixtures thereof.

In cases where the compounds of the invention exist as diastereoisomers, the invention includes individual diastereoisomers as well as mixtures thereof.

Separation of diastereoisomers or E and Z isomers may be achieved by conventional techniques, e.g. by fractional crystallisation, chromatography or H.P.L.C. An individual enantiomer of a compound of the invention may be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds of the invention.

Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

The invention also includes all suitable isotopic variations of the compounds of the invention. An isotopic variation is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as $^3$H or $^{14}$C is incorporated, are useful in drug and/or substrate tissue distribution studies. Tritiated, i.e. $^3$H, and carbon-14, i.e. $^{14}$C isotopes are particularly preferred for their ease of preparation and detectability. Further, substitution with isotopes such as deuterium, i.e. $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the methods or preparations described in the Examples and Preparations hereafter using appropriate isotopic variations of suitable reagents.

Compounds of the invention may be prepared, in known manner in a variety of ways. In the following reaction schemes and hereafter, unless otherwise stated, $R^1$ to $R^{13}$, Z and Y are as defined in the first aspect. These processes form further aspects of the invention.

Throughout the specification, general formulae are designated by Roman numerals I, II, III, IV etc. Subsets of these general formulae are defined as Ia, Ib, Ic etc, . . . IVa, IVb, IVc etc.

Compounds of general formula (I) may be prepared from compounds of formula (II) by reaction with an amine of general formula $HNR^1R^2$, or with a suitable salt form thereof, together with a hydride reducing agent in a suitable solvent (see Scheme 1). When either $R^1$ or $R^2$ is hydrogen, suitable solvents include protic solvents such as ethanol, and sodium borohydride is an appropriate reducing agent as exemplified by Example 36 herein. When neither $R^1$ or $R^2$ are hydrogen, tetrahydrofuran/dichloromethane is a suitable solvent system and sodium triacetoxyborohydride is a suitable reducing agent. In such reactions the use of a salt form of $HNR^1R^2$, such as the hydrochloride is preferable, and an auxiliary base, to aid solubility of the $HNR^1R^2$ salt, such as triethylamine may optionally be added along with acetic acid, as exemplified by Example 25 herein.

SCHEME 1

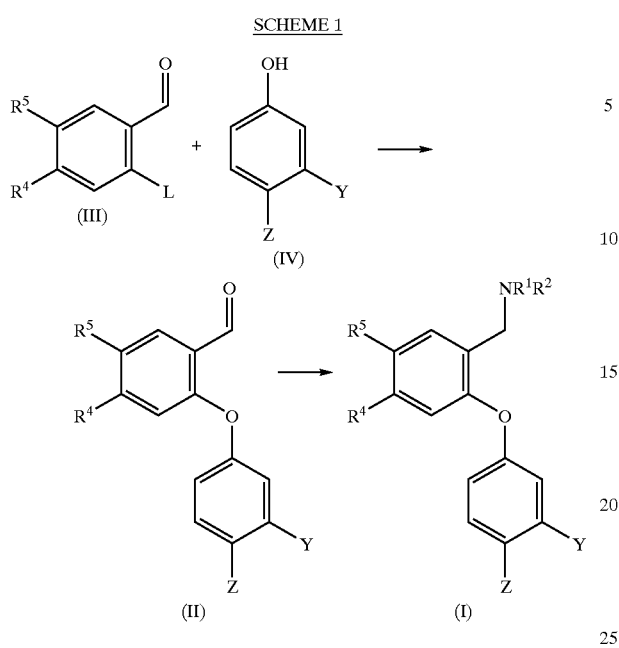

Compounds of formula (II) may be prepared in turn from the coupling of compounds of general formula (IV) with aldehyde compounds of general formula (III), wherein L is a suitable leaving group such as halogen (F, Cl, Br or I) or a sulfonate ester such as trifluoromethanesulfonate or methanesulfonate, preferably L is F or Cl. Such coupling reaction may be accomplished by techniques known in the art, such as via reaction with potassium carbonate in a suitable solvent such as dimethylformamide under appropriate reaction conditions such as elevated temperature and in an inert atmosphere.

Thus according to a further aspect, the invention provides a process for preparing compounds of general formula (I) from compounds of the general formula (II).

Alternatively, $R^4$ and/or $R^5$ may be introduced after ether coupling (see Scheme 2). Compounds of general formula (I) may be prepared from compounds of general formula (Ia), i.e. compounds of general formula (I) where $R^4$ and $R^5$ are hydrogen. Compounds of general formula (Ia) may be prepared from (IIa) in an analogous fashion to the preparation of (I) from (II) (see Scheme 1), while compounds of general formula (IIa) may be prepared from (IV) and (IIIa) in an analogous fashion to the preparation of (II) (see Scheme 1).

SCHEME 2

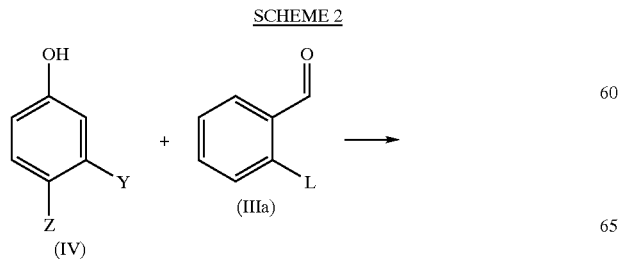

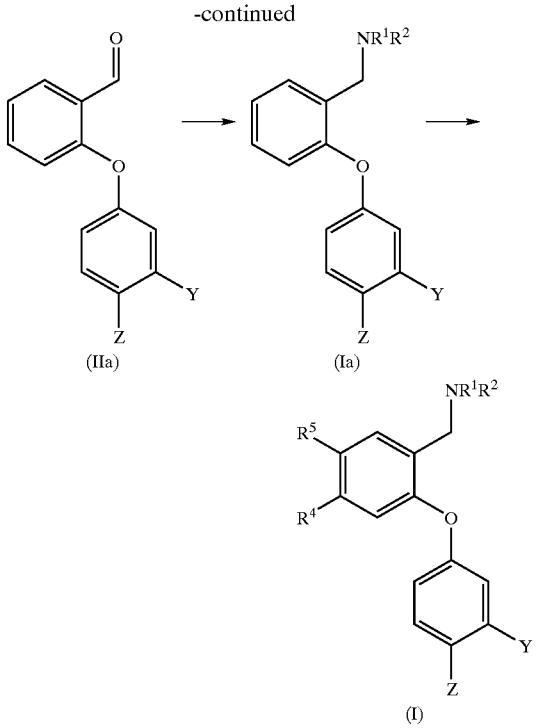

Thus according to a further aspect, the invention provides a process for preparing compounds of general formula (I) from compounds of the general formula (Ia).

Methodologies for introducing $R^4$ and/or $R^5$ into compounds of formula (Ia) include:

i) Where $R^4/R^5$ are halogen, by reaction of (Ia) with a suitable halogenating agent in an inert solvent which does not adversely affect the reaction. Suitable halogenating agents include trifluoromethanesulfonic acid and N-iodosuccinimide and suitable inert solvents include dichloromethane.

ii) Where $R^4/R^5$ are $—NO_2$, by reaction of (Ia) with a suitable nitrating agent, such as an alkali metal nitrate, in a solvent which does not adversely affect the reaction at, or below, room temperature. Suitable nitrating agents include trifluoromethanesulfonic acid/potassium nitrate and suitable solvents include trifluoroacetic acid.

iii) Where $R^4/R^5$ is $—SO_2NR^6R^7$ by reaction of an intermediate sulfonyl chloride with the requisite amine of formula $HNR^6R^7$ in a suitable solvent. Suitable solvents include a mixture of water and dichloromethane and the reactions are generally performed at or below room temperature. The intermediate sulfonyl chlorides may be prepared from compounds of formula (Ia) by reaction with chlorosulfonic acid under low temperature conditions in the presence of a solvent which does not adversely affect the reaction, either with or without subsequent treatment with a chlorinating agent such as phosphorus oxychloride, phosphorus pentachloride, oxalyl chloride or thionyl chloride in a solvent which does not adversely affect the reaction. Suitable solvents for the reaction with chlorosulfonic acid include trifluoroacetic acid and a typical reaction temperature is 0° C. Suitable solvents for the reaction with chlorinating agents include acetonitrile and suitable conditions include at reflux, as illustrated in Example 12 herein.

For example, compounds of formula (Iq), where $R^5$ is —$SO_2NR^6R^7$, may be prepared via the intermediate sulfonyl chlorides (XVIII) from compounds of formula (Ia) by reaction of (Ia) with chlorosulfonic acid, either with or without subsequent treatment with a chlorinating agent such as phosphorus oxychloride, phosphorus pentachloride, oxalyl chloride or thionyl chloride, followed by reaction with $HNR^6R^7$ (see scheme 2a). Reaction conditions typically comprise low temperature. The reaction can take place either neat, i.e. in the absence of solvent, or in the presence of an inert solvent which does not adversely affect the reaction. The intermediate sulfonyl chloride (XVII) may be isolated, purified and then reacted with $HNR^6R^7$, alternatively it may be generated in situ, without isolation, and then reacted with $HNR^6R^7$.

SCHEME 2a

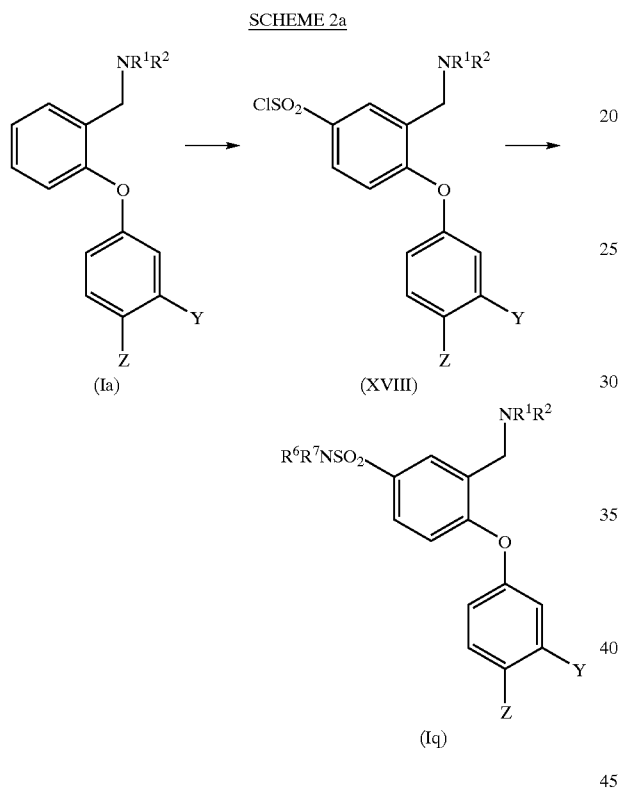

Thus according to a further aspect, the invention provides a process for preparing compounds of general formula (I) from compounds of the general formula (II). In a preferred embodiment, there is provided a process for preparing compounds of formula (Iq) by reacting compounds of formula (Ia) in a suitable solvent, with chlorosulfonic acid, either with or without subsequent treatment with a chlorinating agent such as phosphorus oxychloride, phosphorus pentachloride, oxalyl chloride or thionyl chloride, to give compounds of formula (XVIII) followed by reaction with $HNR^6R^7$ to give compounds of formula (Iq). Preferably compounds of formula (XVIII) are generated in situ and reacted with $HNR^6R^7$ without isolation.

Alternatively, compounds of general formula (I) having a particular $R^4/R^5$ substituent may be converted into other compounds of formula (I) using known techniques. For example:

i) When $R^4/R^5$ is halogen such as chloro, bromo or iodo, it may be converted to cyano via reaction with a cyanide salt in the presence of a Pd(0) or (II) catalyst in a high boiling solvent at elevated temperatures. Suitable Pd catalysts include palladium tetrakis (triphenylphosphine), suitable cyanide salts include $Zn(CN)_2$ and suitable high boiling solvents which do not adversely affect the reaction include dimethylformamide as exemplified by Example 78 herein;

ii) When $R^4/R^5$ is halogen such as chloro, bromo or iodo, it may be converted to the corresponding ester —$CO_2R$ by treatment with carbon monoxide at high pressure with a Pd(0) or (II) catalyst, in an alcohol solvent (ROH wherein R is $C_1$–$C_4$ alkyl), in the presence of a base at elevated temperatures. For example the reaction may be carried out at pressures in the region of about 100 p.s.i, whilst suitable Pd catalysts include dichlorobis (triphenylphosphine) palladium (II), suitable bases include triethylamine and suitable alcohol solvents include methanol as exemplified by Preparation 50 herein;

iii) When $R^4/R^5$ is nitro, it may be reduced to the corresponding —$NH_2$ group via treatment with a reducing agent in a protic solvent at, or above, room temperature. Suitable reducing agents include iron powder/calcium chloride, suitable protic solvents include aqueous ethanol and a typical reaction temperature is from about 70° C. to about 100° C., preferably about 90° C., as exemplified by Example 103 herein;

iv) When $R^4/R^5$ is —$NH_2$, it may be converted to the corresponding —$NHSO_2R^9$ group by reaction with a sulfonylating agent in the presence of a base in an inert solvent which does not adversely affect the reaction at, or below, room temperature. Suitable sulfonylating agents include methanesulfonyl chloride, suitable bases include triethylamine and suitable inert solvents include dichloromethane as exemplified by Example 128 herein;

v) When $R^4/R^5$ is a —$NHSO_2R^9$ group, it may be converted to the corresponding —$NR^8SO_2R^9$ group via treatment with an alkylating agent and a base in a suitable inert solvent. Examples of suitable alkylating agents include methyl iodide, suitable bases include potassium carbonate and suitable inert solvents include acetonitrile, as exemplified by Preparation 88 herein;

vi) When $R^4/R^5$ is a nitrile —CN, it may be converted to the corresponding —$C(O)NH_2$ group by hydrolysis under basic, oxidative or acid conditions. Basic hydrolysis is preferably conducted with a hydroxide salt such as potassium hydroxide in a protic solvent such as t-butanol at elevated temperatures, as exemplified in Example 79 herein.

vii) When $R^4/R^5$ is an ester —$CO_2R$, it may be reduced to the corresponding alcohol group —$CH_2OH$ via treatment with a hydride reducing agent, such as lithium aluminium hydride, as exemplified by Preparation 69 herein;

viii) When $R^4/R^5$ is an ester —$CO_2R$, it may be converted to the corresponding acid —$CO_2H$ by treatment with a suitable hydroxide salt in the presence of water and a suitable co-solvent. Suitable hydroxide salts include lithium hydroxide and suitable co-solvents include tetrahydrofuran, as exemplified by Preparation 55 herein;

ix) When $R^4/R^5$ is an acid —$CO_2H$, it may be converted to the corresponding amide —$CONR^6R^7$ by treatment with a coupling agent, a base and an amine $HNR^6R^7$ in a suitable inert solvent which does not adversely affect the reaction. Suitable coupling agents include 1-(3-dimethylaminopropyl)-3-ethylcarbodiimide hydrochloride in the presence of 1-hydroxybenzotriazole, suitable bases include triethylamine and suitable solvents include dichloromethane, as exemplified by Preparation 59 herein;

x) When $R^4/R^5$ is halogen such as chloro, bromo or iodo, it may be converted to an α,β-unsaturated amide, by treatment with acrylamide, a Pd(0) or (II) catalyst and a suitable base, in an inert solvent which does not adversely affect the reaction, at elevated temperatures. Suitable Pd catalysts include palladium (II) acetate in the presence of tri(o-tolyl)phosphine, suitable bases include triethylamine and suitable inert solvents include acetonitrile as exemplified by Example 50 herein;

xi) When $R^4/R^5$ is an α,β-unsaturated amide, it may be converted to $—CH_2CH_2CO_2NH_2$, by treatment with a suitable reducing agent at an appropriate temperature, in a suitable solvent which does not adversely affect the reaction. Suitable reducing agents include samarium diiodide at room temperature and suitable solvents include tetrahydrofuran containing a small amount of water, as exemplified by Example 51 herein;

xii) When $R^4/R^5$ is $—CH_2OH$, it may be converted to $—CH_2NR^8SO_2R^9$ by means of a Mitsunobu reaction at an appropriate temperature, in a suitable solvent which does not adversely affect the reaction. Suitable reagents include diethyl azodicarboxylate, triphenylphosphine and tert-butyl methylsulfonylcarbamate, 0° C. is a suitable reaction temperature and tetrahydrofuran is a suitable solvent as exemplified by Preparation 72 herein;

Alternatively, compounds of general formula (I) having a particular $NR^1R^2$ group may be converted into other compounds of general formula (I) having a different $NR^1R^2$ group. For example:

i) Compounds of formula (Ib) wherein either $R^1$ or $R^2$ is hydrogen, can be converted into a compound of formula (Ic) wherein neither $R^1$ nor $R^2$ are hydrogen, by reaction of the compound of formula (Ib) with an aldehyde and a hydride reducing agent. Suitable aldehydes include formaldehyde, suitable reducing agents include sodium tri(acetoxy)borohydride and the reaction is preferably conducted in a solvent which does not interfere with the reaction, such as dichloromethane at or below room temperature, as exemplified by Example 12 herein.

ii) Compounds of formula (Ib) wherein $R^1$ or $R^2$ is hydrogen, can be converted into a compound of formula (Ic) wherein $R^1$ or $R^2$ is methyl, by reaction of the compound of formula (Ib) with a formylating agent in a suitable solvent, followed by subsequent reduction of the intermediate N-formyl compound with a hydride reducing agent in an inert solvent, preferably at elevated temperature. Suitable formylating agents include pentafluorophenyl formate (formed from formic acid, pentafluorophenol and dicyclohexylcarbodiimide) and suitable solvents for the formylation include dichloromethane. Suitable reducing agents include borane-tetrahydrofuran complex and suitable inert solvents for the reduction include tetrahydrofuran as exemplified by Example 110 herein.

Alternatively, compounds of general formula (I) may be prepared from compounds of formula V (see Scheme 3) wherein L is as defined for Scheme 1 and T is a group which can be converted into $CH_2NR^1R^2$. Examples of suitable T substitutents include: $—CO_2R^{10}$, $—CN$ and $—C(O)NR^1R^2$.

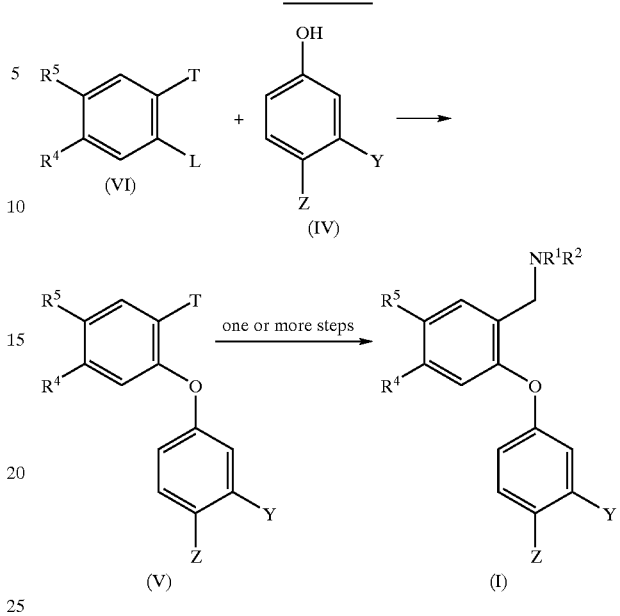

SCHEME 3

Methodologies for converting compounds of formula (V) to (I), include:

i) Where T is $—CO_2R^{10}$ and $R^{10}$=methyl or ethyl, by reaction with an amine of general formula $NHR^1R^2$ to form an amide, followed by reduction to provide an amine.

ii) Where T=$—CN$, by reduction to its corresponding amine of formula $—CH_2NH_2$.

iii) Where T=$—C(O)NR^1R^2$, by reduction to provide an amine.

Compounds of general formula (V) may be prepared in turn by the coupling of compounds of general formula (VI) and compounds of the general formula (IV). Reagents and conditions for such coupling reactions are as previously defined for the coupling of compounds of general formulae (IV) and (III) in Scheme 1.

Compounds of general formula (VI) may be prepared in turn from compounds of general formula (VII) (see Scheme 4).

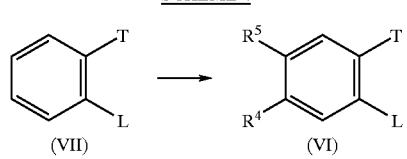

SCHEME 4

Compounds of formula (VI) may be prepared by aromatic electrophilic substitution of compounds of formula (VII) to give compounds of formula (VI) directly. Alternatively compounds of formula (VI) may be prepared in two or more steps; aromatic electrophilic substitution of compounds of formula (VII) to give intermediate compounds which then undergo further reaction to give compounds of formula (VI). The intermediate compounds may be isolated or generated in situ without isolation. A preferred route is shown in Scheme 5.

SCHEME 5

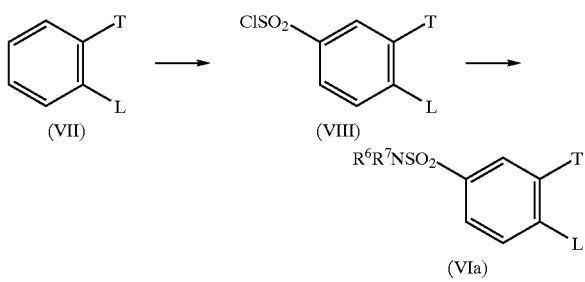

Compounds of formula (VII) are reacted with sulfonyl chloride to give compounds of formula (VII) followed by reaction with NHR⁶R⁷ to give compounds of formula (VIa).

According to further aspects, the invention provides compounds of formulae (II), (IIa) and (V) as defined above.

Compounds of formulae (III), (IIIa), (IV), (VI) or (VII) are either known and available from commercial sources or are available from commercially available materials using known techniques (see Examples hereinafter).

It will be apparent to those skilled in the art that sensitive functional groups may need to be protected and deprotected during synthesis of a compound of formula I. This may be achieved by conventional techniques, for example as described in 'Protective Groups in Organic Synthesis', 3rd edition, by T W Greene and P G M Wuts, John Wiley and Sons Inc, 1999. Example 35 provides one example of a protecting group strategy employed in the synthesis of a compound of the present invention.

The skilled chemist will appreciate that diaryl ethers may be prepared using a number of synthetic methodologies. For a review of methodologies see J S Sawyer, *Tetrahedron*, 56 (2000) 5045–5065, incorporated herein by reference.

The compounds of the invention are useful because they have pharmacological activity in mammals, including humans. More particularly, they are useful in the treatment or prevention of a disorder in which the regulation of monoamine transporter function is implicated. Disease states that may be mentioned include hypertension, depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

Disorders of particular interest include depression, attention deficit hyperactivity disorder, obsessive-compulsive disorder, post-traumatic stress disorder, substance abuse disorders and sexual dysfunction including (in particular) premature ejaculation. Premature ejaculation may be defined as persistent or recurrent ejaculation before, upon or shortly after penile penetration of a sexual partner. It may also be defined as ejaculation occurring before the individual wishes [see 'The Merck Manual', 16th edition, p 1576, published by Merck Research Laboratories, 1992].

Thus, according to further aspects, the invention provides:
  i) a compound of the invention for use as a pharmaceutical;
  ii) the use of a compound of the invention in the manufacture of a medicament for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation;
  iii) the use of a compound of the invention in the manufacture of a medicament for the treatment or prevention of premature ejaculation;
  iv) a method of treatment or prevention of depression, attention deficit hyperactivity disorder, obsessive-compulsive disorder, post-traumatic stress disorder, substance abuse disorders or sexual dysfunction including premature ejaculation, which comprises administering a therapeutically effective amount of a compound of the invention to a patient in need of such treatment or prevention;
  v) a method of increasing ejaculatory latency which comprises the administration of an effective amount of a compound of the invention to a male desiring increased ejaculatory latency; and
  vi) a compound of the invention for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation.
  vii) a compound of the invention for treating premature ejaculation.

It is to be appreciated that all references herein to treatment include curative, palliative and prophylactic treatment.

The compounds of the invention may be administered alone or as part of a combination therapy. If a combination of active agents are administered, then they may be administered simultaneously, separately or sequentially. In particular, the compounds of the invention may be combined with the following preferably for the treatment of PE:
  i) Alpha-blockers (e.g. phentolamine, doxazasim, tamsulosin, terazasin, prazasin and Example 19 of WO9830560. A possible rationale for alpha-blockers treating premature ejaculation is as follows. Muscular activity of the ejaculatory smooth muscles (vas deferens, seminal vesicles and urethra) are controlled by the sympathetic nervous system through the release of noradrenalin. Noradrenalin acts on the alpha 1 adrenoreceptors, stimulating muscle contractions, leading to seminal emission and subsequently ejaculation. Blocking these receptors will therefore inhibit ejaculation.
ii) Apomorphine—teachings on the use of apomorphine as a pharmaceutical may be found in U.S. Pat. No. 5,945,117.
iii) Dopamine D2 agonists (e.g. Premiprixal, Pharmacia Upjohn compound number PNU95666).
iv) Melanocortin receptor agonists (e.g. Melanotan II).
v) PGE1 receptor agonists (e.g. alprostadil).
vi) Mono amine transport inhibitors, particularly Noradrenaline Re-uptake Inhibitors (NRIs) (e.g. Reboxetine), other Serotonin Re-uptake Inhibitors (SRIs) (e.g. paroxetine) or Dopamine Re-uptake Inhibitors (DRIs).
vii) 5-HT3 antagonists (e.g. ondansetron and granisetron). A possible rationale for 5-HT3 antagonists treating premature ejaculation is as follows. 5-HT3 receptors, present in the lumen of the posterior portion of the urethra, are stimulated by 5-HT in the semen during seminal emission, leading to a sensitisation of the spinal relex pathway which leads to ejaculation. Therefore, an antagonist would prevent this sensitisation and thus delay ejaculation.
viii) PDE inhibitors such as PDE2 (e.g. erythro-9-(2-hydroxyl-3-nonyl)-adenine) and Example 100 of EP 0771799-incorporated herein by reference) and in particular a PDE5 inhibitor (e.g. sildenafil, 1-{[3-(3,4-dihydro-5-methyl-4-oxo-7-propylimidazo[5,1-f]-astrazin-2-yl)-4-ethoxyphenyl]sulfonyl}-4-ethylpiperazine i.e. vardenafil/Bayer BA 38-9456 or IC351 (see structure below, Icos Lilly)). A possible rationale for PDE inhibitors treating premature ejaculation is as follows. c AMP and CGMP levels in the ejaculatory smooth muscles regulate muscle tone of these ejaculatory muscles and so delay ejaculation.

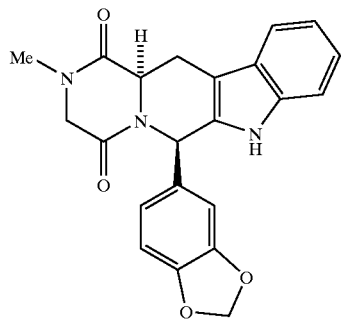

IC351 (Icos Lilly)

ix) Potassium channel openers.
x) P2X purinergic receptor antagonists.
xi) Endothelin receptor antagonists For human use the compounds of the invention can be administered alone but in human therapy will generally be administered in admixture with a suitable pharmaceutical excipient, diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The following dosage levels and other dosage levels herein are for the average human subject having a weight range of about 65 to 70 kg. The skilled person will readily be able to determine the dosage levels required for a subject whose weight falls outside this range, such as children and the elderly.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound of the invention whilst tablet fill weights may range from 50 mg to 1000 mg. An example formulation for a 10 mg tablet is illustrated:

| Ingredient | % w/w |
|---|---|
| Compound of the invention | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetra-fluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of compounds of the invention will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred. Preferably, administration takes place shortly before an effect is required.

For veterinary use, a compound of the invention is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of the invention and a pharmaceutically acceptable adjuvant, diluent or carrier.

The invention is illustrated by the following non-limiting examples in which the following abbreviations and definitions are used:

| | |
|---|---|
| Arbocel ® | filter agent |
| br | broad |
| Boc | tert-butoxycarbonyl |
| CDI | carbonyldiimidazole |
| δ | chemical shift |
| d | doublet |
| Δ | heat |
| DCCI | dicyclohexylcarbodiimide |
| DCM | dichloromethane |
| DMF | N,N-dimethylformamide |
| DMSO | dimethylsulfoxide |
| ES+ | electrospray ionisation positive scan |
| ES− | electrospray ionisation negative scan |
| Ex | Example |
| h | hours |
| HOBt | 1-hydroxybenzotriazole |
| HPLC | high pressure liquid chromatography |
| m/z | mass spectrum peak |
| min | minutes |
| MS | mass spectrum |
| NMR | nuclear magnetic resonance |
| Prec | precursor |
| Prep | preparation |
| q | quartet |
| s | singlet |
| t | triplet |
| Tf | trifluoromethanesulfonyl |
| TFA | trifluoroacetic acid |
| THF | tetrahydrofuran |
| TLC | thin layer chromatography |
| TS+ | thermospray ionisation positive scan |
| WSCDI | 1-(3-dimethylaminopropyl)-3-ethylcarbodiimide hydrochloride |

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO, dimethylsulfoxide. The abbreviation psi means pounds per square inch and LRMS means low resolution mass spectrometry. Where thin layer chromatography (TLC) has been used it refers to silica gel TLC using silica gel 60 F$_{254}$ plates, R$_f$ is the distance travelled by a compound divided by the distance travelled by the solvent front on a TLC plate. Melting points were determined using a Perkin Elmer DSC7 at a heating rate of 20° C./minute).

Where indicated, compounds were characterised as their hydrochloride salts. A typical procedure for formation of hydrochloride salts is given in Example 12. The procedure can be carried out with other solvents e.g. diethyl ether or DCM.

Commercial starting materials were obtained from Aldrich Chemical Co, Lancaster Synthesis Ltd or Acros Organics.

EXAMPLES 1

3-[(Methylamino)methyl]-4-[3-methyl-4-methylsulfanyl)phenoxy]-benzenesulfonamide

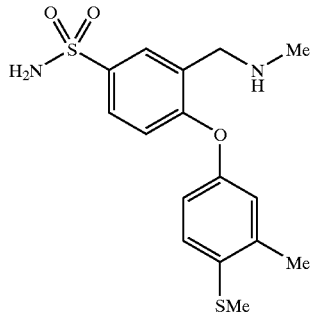

The amide of Preparation 8 (760 mg, 2.07 mmol) was slurried in THF (10 mL) and the resulting suspension was treated with borane.tetrahydrofuran complex (1M solution in THF, 6.22 mL, 6.22 mmol) at room temperature. The resulting solution was heated at reflux for 5 hours under an atmosphere of dry nitrogen. The reaction was cooled to room temperature and treated cautiously with 6M HCl solution (6 mL). The resulting mixture was heated at reflux for 30 min. After cooling to room temperature the mixture was diluted with water (10 mL) and basified by cautious addition of potassium carbonate solid. The aqueous layer was extracted with EtOAc (20 mL) which gave a precipitate in the organic layer, and the aqueous layer was further extracted with DCM (2×20 mL). The EtOAc fraction was washed with 2M NaOH (20 mL) giving a clear two-phase separation and the basic layer was extracted with DCM (4×25 mL). All the organic fractions were combined and washed with brine (20 mL), dried (MgSO$_4$) and evaporated to a colourless oil. Purification by flash chromatography [SiO$_2$; 95:5:0.5 to 90:10:1 (EtOAc/MeOH/880 NH$_3$)] afforded a white powder of the desired amine (646 mg, 89%). δ$_H$ (300 MHz, d$_6$-DMSO) 2.26 (3H, d), 2.32 (3H, d), 2.45 (3H, d), 3.75 (2H, d), 6.90 (3H, m), 7.25 (3H, br), 7.67 (1H, t) 7.98 (1H, d); MS m/z (TS+) 353 (MH+).

Compounds of formula Id, i.e. compounds of general formula I where R$^1$ is methyl, R$^2$ is hydrogen and R$^5$ is —SO$_2$NH$_2$, shown in Table 1 were prepared in an analogous fashion to Example 1 from the precursors indicated.

TABLE 1
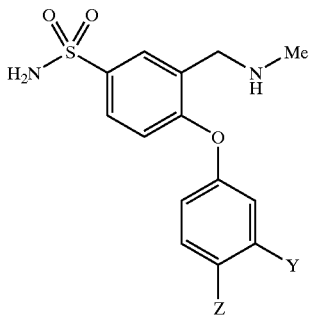
(Id)
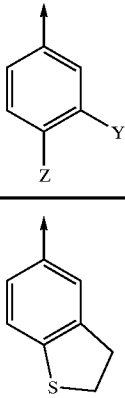
| Example | Precursor | Z | data |
|---|---|---|---|
| 2 | Prep 9 | 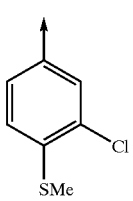 | HCl salt: δ_H (CD_3OD, 400 MHz) 2.80 (3H, s), 3.42 (2H, m), 4.41 (2H, s), 6.86–7.00 (2H, m), 7.09 (1H, s), 7.23 (1H, d), 7.90 (1H, d), 8.05 (1H, s); MS m/z (TS$^+$) 351 (MH$^+$) |
| 3 | Prep 12 | 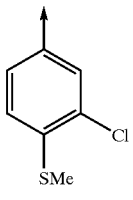 | HCl salt: δ_H (CD_3OD, 300 MHz) 2.54 (3H, s), 2.82 (3H, s), 4.43 (2H, s), 7.00 (1H, d), 7.20 (1H, d), 7.34 (1H, s), 7.42 (1H, d), 7.95 (1H, d), 8.11 (1H, s); MS m/z (TS$^+$) 373 (MH$^+$) |
| 4 | Prep 11 | 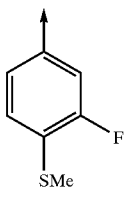 | HCl salt: δ_H (CD_3OD, 400 MHz) 2.45 (3H, s), 2.73 (3H, s), 5.44 (2H, s), 6.97 (3H, m), 7.42 (1H, m), 7.89 (1H, m), 8.03 (1H, s); MS m/z (ES$^+$) 357 (MH$^+$) |
| 5 | Prep 10 | 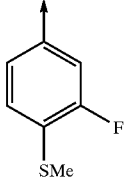 | HCl salt: δ_H (CD_3OD, 400 MHz) 2.79 (3H, s), 3.18 (2H, m), 4.38 (2H, s), 4.41 (2H, m), 6.68 (2H, m), 6.97 (1H, d), 7.13 (1H, d), 7.91 (1H, d), 8.03 (1 H, s); MS m/z (TS$^+$) 367 (MH$^+$) |
| 6 | Prep 13 | 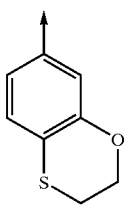 | HCl salt: δ_H (CD_3OD, 400 MHz) 2.78 (3H, s), 3.15 (2H, m), 4.38 (4H, m), 6.79 (1H, d), 6.85 (3H, m), 7.84 (1H, d), 8.00 (1H, s); MS m/z (ES$^+$) 367 (MH$^+$) |

TABLE 1-continued (Id)

Structure: 4-amino-sulfonyl-2-(N-methylaminomethyl)phenyl aryl ether with Y, Z substituents on pendant phenyl ring.

| Example | Precursor | Z (structure with Y) | data |
|---|---|---|---|
| 7 | Prep 14 | 2,3-dihydrobenzofuran-5-yl | HCl salt: $\delta_H$ (CD$_3$OD, 400 MHz) 2.81 (3H, s), 4.43 (2H, s), 5.09 (4K, s), 6.93 (1H, d), 7.12 (2H, s + d), 7.40 (1H, d), 7.90 (1H, d), 8.08 (1H, s); MS m/z (TS$^+$) 335 (MH$^+$) |
| 8 | Prep 15 | indan-5-yl | HCl salt: $\delta_H$ (CD$_3$OD, 400 MHz) 2.16 (2H, m), 2.80 (3H, s), 2.92 (4H, t), 4.40 (2H, s), 6.86 (1H, d), 6.94 (1H, d), 7.03 (1H, s), 7.30 (1H, d), 7.88 (1H, d), 8.03 (1H, s); MS m/z (TS$^+$) 333 (MH$^+$) |
| 9 | Prep 16 | 4-methyl-3-(methylthio)phenyl | HCl salt: $\delta_H$ (CD$_3$OD, 400 MHz) 2.32 (3H, s), 2.43 (3H, s), 2.81 (3H, s), 4.41 (2H, s), 6.84 (1H, d), 6.91 (1H, d), 7.06 (1H, s), 7.24 (1H, d), 7.89 (1H, d), 8.05 (1H, s); MS m/z (ES$^+$) 352 (MH$^+$) |
| 10 | Prep 17 | 1,3-dihydrobenzo[c]thiophen-5-yl | HCl salt: $\delta_H$ (CD$_3$OD, 400 MHz) 2.78 (3H, s), 4.21 (4H, s), 4.39 (2H, s), 6.89 (1H, d), 7.01 (1H, d), 7.08 (1H, s), 7.38 (1H, d), 7.85 (1H, d), 8.02 (1H, s); MS m/z (TS$^+$) 351 (MH$^+$) |
| 11 | Prep 18 | 2,3-dihydrobenzo[b]thiophen-5-yl | $\delta_H$ (CD$_3$OD, 400 MHz) 2.76 (3H, s), 3.30 (2H, m), 3.42 (2H, m), 4.33 (2H, s), 6.90 (1H, d), 6.94 (1H, d), 7.00 (1H, s), 7.29 (2H, d), 7.89 (1H, d), 8.04 (1H, s); MS m/z (ES$^+$) 351 (MH$^+$), (ES$^-$) 349 (M − H$^+$) |

EXAMPLES 12 AND 13

3-[(Dimethylamino)methyl]-4-[3-methyl-4-(methylsulfanyl)phenoxy]-benzenesulfonamide (Example 12) and 3-[(dimethylamino)methyl]-N-methyl-4-[3-methyl-4-(methylsulfanyl)phenoxy] benzenesulfonamide (Example 13)

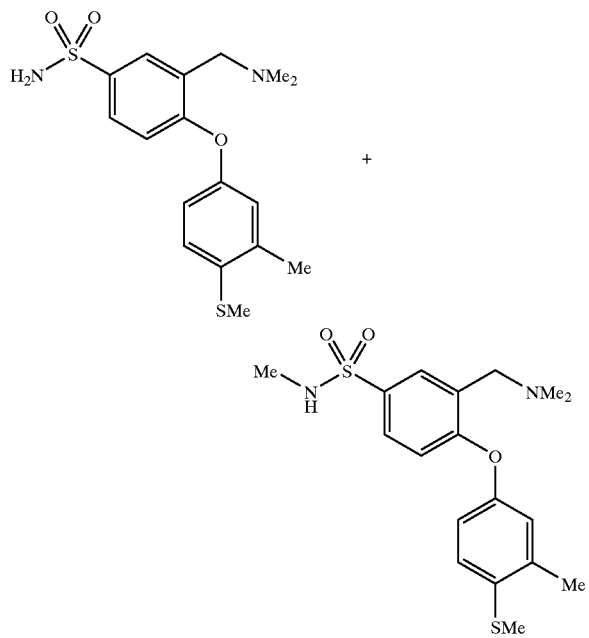

Formaldehyde (37% aq. solution, 282 µL, 3.76 mmol) was added to a suspension of the secondary amine from Example 1 (409 mg, 1.16 mmol) in DCM (20 mL) at room temperature under nitrogen. The resulting mixture was stirred for 15 minutes before the addition of sodium triacetoxyborohydride (984 mg, 4.64 mmol). The resulting reaction mixture was stirred for 5 hours before being basified with saturated $NaHCO_3$ solution (10 mL) and extracted with DCM (3×20 mL). The organic layers were washed with brine (10 mL), dried ($MgSO_4$) and evaporated to a yellow oil. This was purified by HPLC (Phenomonex Luna $C_{18}$ 75×4.6 mm column, $CH_3CN$, $H_2O$, TFA). Fractions containing the major product were evaporated and the residue was treated with sat. $NaHCO_3$ solution (5 mL), and extracted with DCM (3×30 mL). The combined organic fractions were washed with brine (30 mL), dried ($MgSO_4$) and evaporated to give a white foam (155 mg, 36%) of Example 12; $\delta_H$ (300 MHz, $CDCl_3$) 2.30 (6H, s), 2.35 (3H, s), 2.48 (3H, s), 3.60 (2H, s), 6.83 (3H, m), 7.20 (1H, m), 7.28 (2H, s), 7.74 (1H, d), 8.08 (1H, s); MS m/z (TS+) 367 (MH+).

A minor product was also obtained after HPLC purification. The relevant fractions were evaporated and the residue was treated with sat. $NaHCO_3$ solution (5 mL), and extracted with DCM (2×30 mL). The combined organic fractions were washed with brine (30 mL), dried ($MgSO_4$) and evaporated to a gum. This was taken up in DCM (5 mL), treated with 1M ethereal HCl (2 mL) and evaporated to give a white powder (39 mg, 9%) of Example 13; HCl salt: $\delta_H$ ($CDCl_3$, 300 MHz) 2.30 (6H, s), 2.35 (3H, s), 2.48 (3H, s), 3.60 (2H, s), 6.83 (3H, m), 7.20 (1H, m), 7.28 (2H, s), 7.74 (1H, d), 8.08 (1H, s); MS m/z (TS+) 381 (MH+).

In a repeat reaction, using 1 equivalent of formaldehyde to the amine of Example 1, Example 12 was obtained in 78% yield after column chromatography [$SiO_2$; 95:5:0.5 to 90:10:1 (EtOAc/MeOH/880 $NH_3$)]. This was taken up in EtOAc and converted to the HCl salt by the addition of 1M ethereal HCl. The resulting precipitate was filtered and dried in vacuo to give Example 12 HCl salt; m.p. 188° C.

Alternatively, Example 12 can also be formed from the amine of Example 1 by the method of Example 110.

Example 12 was also prepared as follows.

A solution of the hydrochloride salt from Example 94 (20 g) in trifluoroacetic acid (100 mL) was slowly added to a solution of chlorosulfonic acid (72 g) keeping the temperature between 0 and 5° C. After 1 h the reaction mixture was quenched slowly into water (200 mL), at 0–20° C. The mixture was then extracted with dichloromethane (200 mL) and separated. The aqueous layer was then extracted with dichloromethane (60 mL) and separated. The combined organic layers were washed with water (200 mL). The layers were separated and the dichloromethane removed in vacuo to give a solid. Acetonitrile (240 mL) was added and to this slurry was added phosphorus oxychloride (28.8 mL). The solution was then heated at reflux overnight. The reaction mixture was cooled to room temperature and quenched into a stirred mixture of ammonia (90 mL), dichloromethane (240 mL) and water (100 mL), keeping the temperature between 0° C. and 10° C. The mixture was adjusted with ammonia (if necessary) to greater than pH 8. After 15 mins the reaction mixture was allowed to warm to room temperature and the layers separated. The organic layer was concentrated in vacuo to give a thick brown oil. This was dissolved in acetone (100 mL) and slurried with carbon (Norit SX plus, 50% w/w) filtered and treated with another charge of carbon (Norit SX plus, 50% w/w). This mixture was again filtered and the solution concentrated, replacing with water (200 mL). The slurry was granulated, filtered and vacuum dried overnight to give the title product as a creamy white solid (yield 40%).

EXAMPLES 14 AND 15

4-(2,3-Dihydro-1,4-benzoxathiin-7-yloxy)-3-[(dimethylamino)methyl]-benzenesulfonamide and 4-(2,3-dihydro-1,4-benzoxathiin-7-yloxy)-3-[(dimethylamino)methyl]-N-methylbenzenesulfonamide

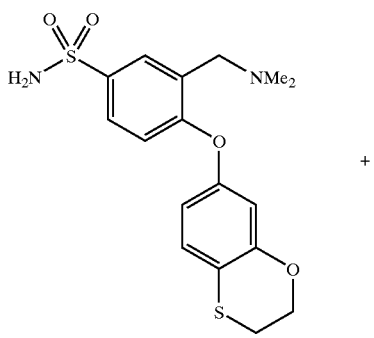

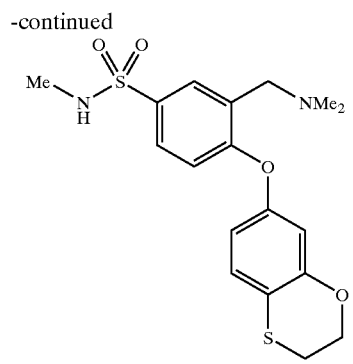

These compounds were formed in an analogous fashion to Examples 12 and 13 starting from the secondary amine of Example 5.

EXAMPLE 14

HCl salt: $\delta_H$ (CD$_3$OD, 400 MHz) 2.97 (6H, s), 3.18 (2H, m), 4.42 (2H, m), 4.52 (2H, s), 6.68 (2H, d), 6.99 (1H, d), 7.14 (1H, d), 7.94 (1H, d), 8.07 (1H, s); MS m/z (ES$^+$) 381 (MH$^+$).

EXAMPLE 15

HCl salt: $\delta_H$ (CD$_3$OD, 400 MHz) 2.56 (3H, s), 2.80 (6H, s), 3.17 (2H, m), 4.35 (2H, s), 4.41 (2H, m), 6.68 (2H, m), 6.98 (1H, d), 7.13 (1H, d), 7.81 (1H, d), 8.00 (1H, s); MS m/z (ES$^+$) 395 (MH$^+$).

Compounds of formula Ie, i.e. compounds of general formula I where R$^1$ and R$^2$ are methyl and R$^5$ is —SO$_2$NH$_2$, shown in Table 2 were prepared according to Example 12 from the precursors indicated. The N-methyl sulfonamides analogous to Example 13 were not isolated in these reactions and HPLC purification was not required.

TABLE 2

(Ie)

| Example | Precursor | Z / Y | data |
|---|---|---|---|
| 16 | Example 2 | (2,3-dihydrobenzothiophen-5-yl) | HCl salt: $\delta_H$ (CD$_3$OD, 400 MHz) 2.98 (6H, s), 3.41 (2H, m), 4.58 (2H, s), 6.95 (2H, m), 7.08 (1H, s), 7.25 (1H, d), 7.95 (1H, d), 8.05 (1H, s); MS m/z (ES$^+$) 365 (MH$^+$) |
| 17 | Example 3 | Z=SMe, Y=Cl | HCl salt: $\delta_H$ (CD$_3$OD, 300 MHz) 2.54 (3H, s), 2.98 (6H, s), 4.53 (2H, s), 7.01 (1H, d), 7.20 (1H, dd), 7.33 (1H, s), 7.42 (1H, d), 7.99 (1H, d), 8.04 (1H, s); MS m/z (TS$^+$) 387 (MH$^+$) |

TABLE 2-continued

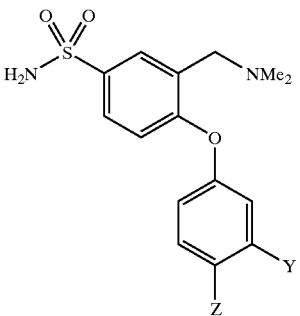

(Ie)

| Example | Precursor | Z / Y | data |
|---|---|---|---|
| 18 | Example 4 | 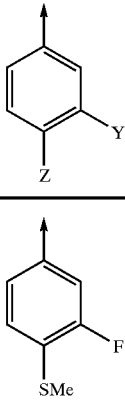 | HCl salt: δ$_H$ (CD$_3$OD, 400 MHz) 2.43 (3H, s), 2.88 (6H, s), 4.42 (2H, s), 6.99 (3H, m), 7.42 (1H, t), 7.92 (1H, d), 8.06 (1H, s); MS m/z (ES$^+$) 371 (MH$^+$) |
| 19 | Example 6 | 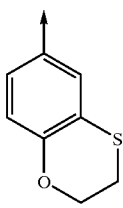 | HCl salt: δ$_H$ (CD$_3$OD, 400 MHz) 2.89 (3H, s), 3.17 (2H, m), 4.39 (2H, m), 4.47 (2H, s), 6.78 (1H, d), 6.87 (3H, m), 7.89 (1H, d), 8.01 (1H, s); MS m/z (TS$^+$) 367 (MH$^+$) |
| 20 | Example 7 | 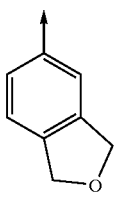 | TFA salt: δ$_H$ (CDCl$_3$, 400 MHz) 2.22 (6H, s), 3.60 (2H, t), 5.05 (4H, d), 6.75–6.90 (3H, m), 7.20 (1H, d), 7.60 (1H, m), 8.00 (1H, m); MS m/z 349 (MH$^+$) |
| 21 | Example 8 | 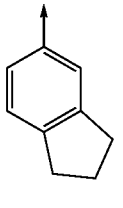 | HCl salt: δ$_H$ (CD$_3$OD, 400 MHz) 2.10 (2H, m), 2.85–3.00 (10H, m), 4.30 (1H, brs), 4.50 (2H, s), 6.80–6.95 (2H, m), 7.05 (1H, s), 7.25 (1H, d), 7.80 (1H, d), 8.10 (1H, s); MS m/z (ES$^+$) 347 (MH$^+$) |
| 22 | Example 10 | 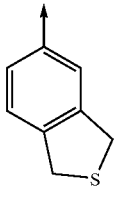 | HCl salt: δ$_H$ (CD$_3$OD, 400 MHz) 2.93 (6H, s), 4.21 (4H, s), 4.50 (2H, s), 6.91 (1H, d), 7.02 (1H, d), 7.09 (1H, s), 7.37 (1H, d), 7.91 (1H, d), 8.05 (1H, s); MS m/z (TS$^+$) 365 (MH$^+$) |

TABLE 2-continued

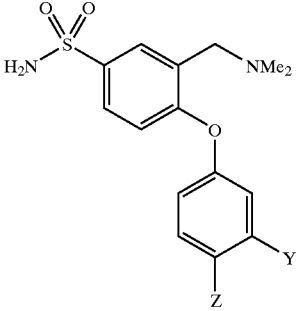

| Example | Precursor | Z | data |
|---------|-----------|---|------|
| 23 | Example 11 | 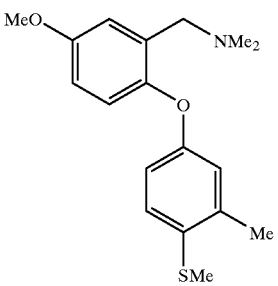 | HCl salt: $\delta_H$ (DMSO-$d_6$, 400 MHz) 2.76 (6H, s), 3.21 (2H, t), 3.38 (2H, t), 4.39 (2H, s), 6.80 (1H, d), 6.86 (1H, d), 7.10 (1H, s), 7.28 (3H, m), 7.80 (1H, d), 8.06 (1H, s), 10.23 (1H, br); MS m/z (TS$^+$) 365 (MH$^+$) |

EXAMPLES 24

3-[(Dimethylamino)methyl]-4-[4-methyl-3-(methylsulfanyl)phenoxy]-benzenesulfonamide

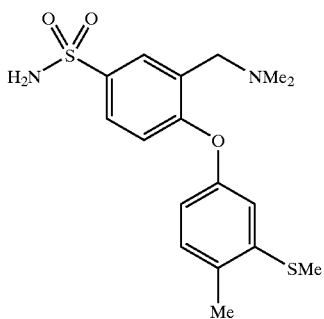

The title compound was prepared from the secondary amine of Example 9 by the method of Example 110; $\delta_H$ (CD$_3$OD, 400 MHz) 2.27 (3H, s), 2.41 (3H, s), 2.61 (6H, s), 4.19 (2H, s), 6.76 (1H, d), 6.88–6.93 (2H, m), 7.20 (1H, d), 7.82 (1H, d), 8.03 (1H, d); MS m/z (TS$^+$) 367 (MH$^+$).

EXAMPLES 25

N-{5-Methoxy-2-[3-methyl-4-(methylsulfanyl)phenoxy]benzyl}-N,N-dimethylamine

Dimethylamine hydrochloride (424 mg, 5.2 mmol), Et$_3$N (725 μL, 5.2 mmol), AcOH (298 μL, 5.2 mmol) and sodium triacetoxyborohydride (1.10 g, 5.2 mmol) were added to a solution of the aldehyde from Preparation 24 (1.00 g, 3.47 mmol) in THF (15 mL) and DCM (15 mL) and the mixture was stirred at room temperature for 16 h. After removing the solvent in vacuo the residue was taken up in 2M HCl (20 mL) and washed with ether (2×15 mL). The aqueous layer was basified with NaOH pellets and extracted with DCM (4×20 mL). The combined DCM extracts were washed with brine, dried (MgSO$_4$) and evaporated. The residue was taken up in a small amount of DCM and treated with 1M ethereal HCl to precipitate the HCl salt. This was filtered, washed with ether and dried to give a white solid (936 mg) contaminated with triethylamine hydrochloride. This was dissolved in 1M NaOH (10 mL) and extracted with EtOAc (3×15 mL). The organic extracts were washed with brine (10 mL), dried (MgSO$_4$) and evaporated before being re-dissolved in EtOAc and evaporated again. The residue was taken up in DCM and treated with 1M ethereal HCl to precipitate the HCl salt, which was filtered, washed with ether and dried to give a white solid (635 mg, 52%); $\delta_H$ (CDCl$_3$, 300 MHz) 2.35 (3H, s), 2.45 (3H, s), 2.79 (6H, s), 3.90 (3H, s), 4.21 (2H, s), 6.70 (1H, d), 6.73 (1H, s), 6.90 (2H, m), 7.18 (1H, d), 7.65 (1H, s), 12.83 (1H, brs); MS m/z (TS$^+$) 318 (MH$^+$).

Compounds of formula If, i.e. compounds of general formula I where R$^1$ and R$^2$ are methyl, shown in Table 3 were prepared according to Example 25 from the precursors indicated.

TABLE 3

(If)

| Example | Precursor | R$^4$ | R$^5$ | Z | data |
|---------|-----------|-------|-------|---|------|
| 26 | Prep 25 | H | F | quinolinyl | HCl salt: $\delta_H$ (CDCl$_3$, 300 MHz) 2.23 (6H, s), 3.41 (2H, s), 6.98 (2H, m), 7.34 (2H, m), 7.48 (1H, dd), 7.98 (1H, d), 8.08 (1H, d), 8.80 (1H, s); MS m/z (TS$^+$) 297 (MH$^+$) |
| 27 | Prep 39 | H | —NO$_2$ | 3-Me-4-SMe-phenyl | $\delta_H$ (CDCl$_3$, 300 MHz) 2.32 (6H, s), 2.36 (3H, s), 2.47 (3H, s), 3.60 (2H, s), 6.80 (1H, d), 6.87 (2H, d), 7.19 (1H, d), 8.03 (1H, d), 8.40 (1H, d); MS m/z (ES$^+$) 333 (MH$^+$) |
| 28 | Prep 38 | H | —NO$_2$ | 2,3-dihydrobenzothiophenyl | Taken on crude at ~75% purity; $\delta_H$ (CDCl$_3$, 400 MHz) 2.33 (6H, s), 3.24 (2H, m), 3.38 (2H, m), 3.66 (2H, s), 6.76 (2H, m), 6.86 (1H, m), 7.17 (1H, d), 8.00 (1H, dd), 8.37 (1H, d) |
| 29 | Prep 26 | H | H | quinolinyl | $\delta_H$ (CDCl$_3$, 300 MHz) 2.28 (6H, s), 3.50 (2H, s), 7.03 (2H, m), 7.20–7.40 (3H, m), 7.52 (2H, m), 7.98 (1H, d), 8.09 (1H, d), 8.81 (1H, m); MS m/z (TS$^+$) 279 (MH$^+$) |

TABLE 3-continued (If)

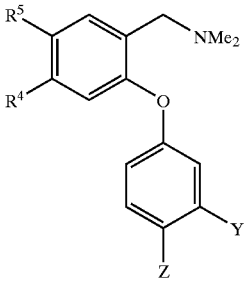

| Example | Precursor | R⁴ | R⁵ | Z (structure) | data |
|---|---|---|---|---|---|
| 30 | Prep 27 | H | H | quinazoline | HCl salt: δ_H (d_6-DMSO, 300 MHz) 2.77 (6H, d), 4.38 (2H, d), 7.08 (1H, d), 7.36 (1H, t), 7.52 (1H, t), 7.62 (1H, s), 7.80 (1H, d), 7.91 (1H, dd), 8.10 (1H, d), 9.25 (1H, s), 9.52 (1H, s); MS m/z (TS⁺) 280 (MH⁺) |
| 31 | Prep 29 | H | H | benzothiazole | Maleate salt: δ_H (d_6-DMSO, 300 MHz) 2.77 (6H, S), 4.33 (2H, s), 5.98 (2H, s), 6.87 (1H, d), 7.21 (1H, dt), 7.30 (1H, dd), 7.41 (1H, dt), 7.58 (1H, dd), 7.88 (1H, d), 8.11 (1H, d), 9.32 (1H, S); MS m/z 285 (MH⁺) |
| 32 | Prep 33 | H | Br | 2,3-dihydrobenzothiophene | HCl salt: δ_H (DMSO-d_6, 400 MHz) 2.77 (6H, d), 3.23 (3H, m). 3.39 (2H, m), 4.32 (2H, d), 6.75 (2H, m), 7.03 (1H, s), 7.26 (1H, d), 7.57 (1H, dd), 7.87 (1H, s), 10.06 (1H, br, s); MS m/z (ES⁺) 366 (MH⁺) |
| 33 | Prep 32 | Br | H | Y=Me, Z=SMe | δ_H (CDCl₃, 400 MHz) 2.22 (6H, s), 2.30 (3H, s), 2.41 (3H, s), 3.41 (2H, s), 6.76 (2H, m), 6.94 (1H, s), 7.18 (1H, s), 7.21 (1H, obs), 7.30 (1H, d); MS m/z (TS⁺) 366/368 (MH⁺) |

EXAMPLE 34

3-[(Dimethylamino)methyl]-N-methyl-4-(6-quinolinyloxy)benzenesulfonamide

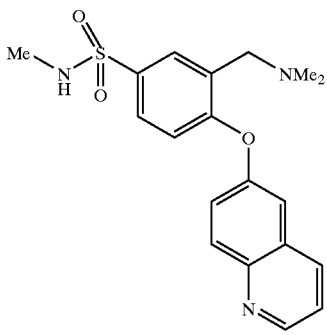

Chlorosulfonic acid (106 μL, 1.6 mmol) was added to a solution of Example 29 (50 mg, 0.16 mmol) in DCM (2 mL) and the mixture was stirred for 3 h at room temperature. Water (2 mL) was added, the mixture was adjusted to pH 6 with sat aq NaHCO$_3$ and extracted with DCM (2×5 mL). The organic extracts were dried (MgSO$_4$) and filtered and 8M methylamine in EtOH (0.3 mL) was added. After standing for 1 h the solvent was removed in vacuo and the residue was purified by column chromatography [SiO$_2$; 95:5:0.5 (DCM/MeOH/880 NH$_3$)]. The product was taken up in EtOAc and converted to the HCl salt by the addition of ethereal HCl. This gave the desired product as a hygroscopic solid (3 mg, 5%); $\delta_H$ (CD$_3$OD, 300MHz) 2.60 (3H, s), 2.99 (6H, s), 4.60 (2H, s), 7.21 (1H, d), 7.96 (1H, d), 8.04 (3H, m), 8.19 (1H, s), 8.38 (1H, d), 9.03 (1H, d), 9.18 (1H, d); MS m/z (TS$^+$) 371 (MH$^+$).

EXAMPLE 35

3-[(Methylamino)methyl]-4-(6-quinolinyloxy)benzenesulfonamide

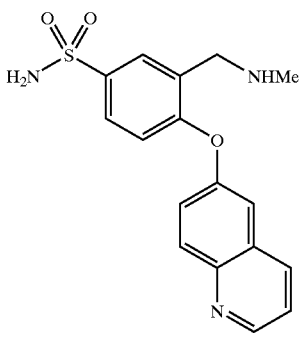

Trifluoroacetic anhydride (0.96 mL, 6.8 mmol) was added to a solution of the amine of Example 48 (900 mg, 3.4 mmol) and triethylamine (1.9 mL, 13.6 mmol) in CH$_2$Cl$_2$ (15 mL) at 0° C. and the mixture was stirred for 5 min. The solvent was removed in vacuo and the residue was partitioned between CH$_2$Cl$_2$ and water. The organic layer was washed with brine, dried (MgSO$_4$) and evaporated to give a yellow oil, which was used without further purification. This crude oil was taken up in CH$_2$Cl$_2$ (20 mL), cooled to 0° C. and ClSO$_3$H (2.4 mL, 36.1 mmol) was added dropwise. The mixture was allowed to warm to room temperature and stirred for 4 h before being poured into ice water. The mixture was extracted with CH$_2$Cl$_2$ (50 mL) and the organic layer was treated with a saturated solution of NH$_3$ in MeOH (10 mL). After stirring for 4 h 1M LiOH (20 mL) was added and stirring was continued overnight. Tlc analysis indicated reaction was incomplete so further 1M LiOH (50 mL) was added and the mixture was stirred for 2 h. The mixture was acidified to pH 8 with 2M HCl and extracted with CH$_2$Cl$_2$ (3×200 mL). The combined organic extracts were dried (MgSO$_4$) and evaporated and the residue was triturated with ether to give the title compound (500 mg, 43%) as a yellow solid; $\delta_H$ (CDCl$_3$, 400 MHz) 2.46 (3H, s), 3.87 (2H, s), 6.93 (1H, d), 7.25 (1H, s), 7.39 (1H, t), 7.42 (1H, d), 7.78 (1H, d), 8.00–8.08 (2H, m), 8.12 (1H, d), 8.86 (1H, s); MS m/z (ES$^+$) 344 (MH$^+$).

EXAMPLE 36

N-[5-Bromo-2-(2,3-dihydro-1-benzothien-5-yloxy)benzyl]-N-methylamine

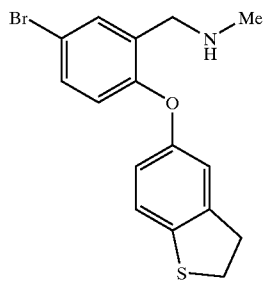

The aldehyde of Preparation 19 (1.10 g, 3.28 mmol) was dissolved in 8M methylamine in EtOH (4.1 mL, 32.8 mmol) and stirred for 5 h before the portionwise addition of NaBH$_4$ (372 mg, 9.83 mmol) over 30 min. EtOH (100 mL) was added and the reaction was stirred for 16 h before being concentrated in vacuo. The residue was quenched with 6M HCl until pH 1 and the precipitated HCl salt was collected by filtration, washed with water (100 mL) and dried in vacuo to give a crystalline solid (1.04 g, 82%); $\delta_H$ (CDCl$_3$, 400 MHz) 2.62 (3H, s), 3.26 (2H, t), 3.41 (2H, t), 4.18 (2H, s), 6.66 (1H, d), 6.90 (1H, d), 7.03 (1H, s), 7.19 (1H, d), 7.39 (1H, d), 7.80 (1H, s); MS m/z (ES$^+$) 350, 352 (MH$^+$).

Compounds of formula Ig, i.e. compounds of general formula I where R$^1$ and R$^4$ are hydrogen and R$^2$ is methyl, shown in Table 4 were prepared according to Example 36 from the precursors indicated. For those compounds which were isolated as the free base the reaction mixture was partitioned between 2M HCl and ether after removal of the reaction solvent in vacuo. The aqueous layer was then basified and extracted with DCM, the DCM layer being dried (MgSO$_4$) and evaporated to give the desired secondary amine.

TABLE 4

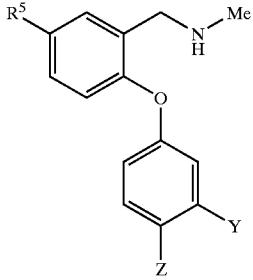

(Ig)

| Example | Precursor | R⁵ | Z 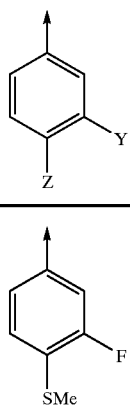 Y | data |
|---|---|---|---|---|
| 37 | Prep 20 | Br | 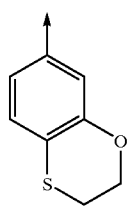 (F, SMe) | HCl salt: δ$_H$ (d$_6$-DMSO, 300 MHz) 2.48 (3H, s), 2.59 (3H, s), 4.18 (2H, s), 6.88 (1H, d), 7.01 (1H, d), 7.16 (1H, d), 7.45 (1H, t), 7.59 (1H, d), 7.91 (1H, s); MS m/z (TS⁺) 356, 358 (MH⁺) |
| 38 | Prep 21 | Br | 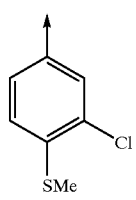 (benzodioxine-S) | δ$_H$ (CDCl$_3$, 400 MHz) 2.43 (3H, s), 3.11 (2H, t), 3.78 (2H, s), 4.41 (2H, t), 6.44 (1H, s), 6.51 (1H, d), 6.77 (1H, d), 6.98 (1H, d), 7.31 (1H, d), 7.55 (1H, s); MS m/z (ES⁺) 366, 368 (MH⁺) |
| 39 | Prep 22 | Br | 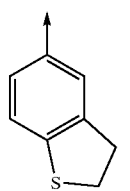 (Cl, SMe) | δ$_H$ (CDCl$_3$, 400 MHz) 2.41 (3H, s), 2.45 (3H, s), 3.72 (2H, s), 6.77 (1H d), 6.85 (1H, d), 6.99 (1H, s), 7.18 (1H, d), 7.36 (1H, d), 7.59 (1H, s); MS m/z (TS⁺) 372, 374 (MH⁺) |
| 40 | Prep 38 | —NO$_2$ | 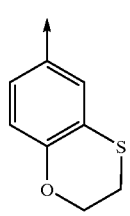 (dihydrobenzothiophene) | δ$_H$ (CDCl$_3$, 300 MHz) 2.55 (3H, s), 3.30 (2H, m), 3.43 (2H, m), 3.95 (2H, s), 6.80 (2H, m), 6.91 (1H, s), 7.22 (1H, d), 8.05 (1H, d), 8.40 (1H, s); MS m/z (ES⁺) 317 (MH⁺) |
| 41 | Prep 36 | —NO$_2$ | (benzodioxine-S) | δ$_H$ (CDCl$_3$, 400 MHz) 2.45 (3H, S), 3.10 (2H, m), 3.86 (2H, s), 4.40 (2H, m), 6.53 (2H, m), 6.80 (1H, d), 7.01 (1H, d), 8.00 (1H, d), 8.27 (1H, s); MS m/z (TS⁺) 333 (MH⁺) |

TABLE 4-continued

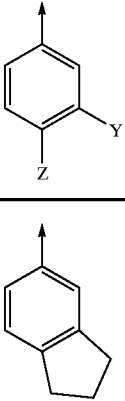

(Ig)

| Example | Precursor | R⁵ | Z/Y group | data |
|---|---|---|---|---|
| 42 | Prep 40 | —NO₂ | (indane) | $\delta_H$ (CDCl$_3$, 400 MHz) 2.14 (2H, m), 2.52 (3H, s), 2.93 (4H, t), 3.92 (2H, s), 6.78 (1H, d), 6.81 (1H, d), 6.91 (1H, s), 7.22 (1H, d), 8.02 (1H, dd), 8.29 (1H, s); MS m/z (TS⁺) 299 (MH⁺) |
| 43 | Prep 24 | —OMe | Y=Me, Z=SMe | HCl salt: $\delta_H$ (CDCl$_3$, 300 MHz) 2.35 (3H, s), 2.45 (3H, s), 2.60 (3H, s), 3.84 (3H, s), 4.17 (2H, s), 6.80 (1H, d), 6.82 (1H, s), 6.88 (2H, s), 7.15 (1H, d), 7.42 (1H, s), 9.85 (2H, brs); MS m/z (TS⁺) 304 (MH⁺) |
| 44 | Prep 23 | Br | Y=Me, Z=SMe | $\delta_H$ (CDCl$_3$, 300 MHz) 2.35 (3H, s), 2.45 (6H, s), 3.77 (2H, s), 6.73 (2H, m), 6.80 (1H, s), 7.19 (1H, d), 7.32 (1H, d), 7.57 (1H, s); MS m/z (TS⁺) 352, 354 (MH⁺) |
| 45 | Prep 30 | H | Y=Me, Z=SMe | HCl salt: $\delta_H$ (d$_6$-DMSO, 400 MHz) 2.22 (3H, s), 2.42 (3H, s), 2.58 (3H, s), 4.18 (2H, s), 6.78 (1H, d), 6.96 (1H, d), 6.99 (1H, s), 7.18 (1H, t), 7.25 (1H, d), 7.38 (1H, t), 7.60 (1H, d); MS m/z (ES⁺) 274 (MH⁺) |

TABLE 4-continued (Ig)

[Structure Ig: R⁵-substituted phenyl with CH₂-NH-Me group, connected via O to a phenyl bearing Y and Z substituents]

| Example | Precursor | R⁵ | Z [with Y] | data |
|---|---|---|---|---|
| 46 | Prep 31 | H | 2,3-dihydrobenzothiophen-5-yl | HCl salt: $\delta_H$ (CDCl₃, 400 MHz) 2.55 (3H, brs), 3.21 (2H, t), 3.32 (2H, m), 4.17 (2H, s), 6.76 (1H, d), 6.84 (1H, d), 6.99 (1H, s), 7.04 (1H, m), 7.12 (1H, d), 7.28 (1H, obs), 7.61 (1H, d); MS m/z (ES⁺) 272 (MH⁺) |
| 47 | Prep 28 | H | quinolin-7-yl | Maleate salt: $\delta_H$ (DMSO-d₆, 400 MHz) 2.60 (3H, s), 4.19 (2H, s), 5.99 (2H, s), 7.03 (1H, d), 7.29 (1H, m), 7.37 (1H, s), 7.45 (3H, m), 7.60 (1H, d), 8.06 (1H, d), 8.37 (1H, d), 8.74 (2H, br), 8.83 (1H, dd); MS m/z 264 (MH⁺) |
| 48 | Prep 26 | H | quinolin-6-yl | $\delta_H$ (CDCl₃, 300 MHz) 2.64 (3H, s), 4.25 (2H, s), 6.89 (1H, d), 7.19 (1H, t), 7.30–7.41 (2H, m), 7.45 (1H, s), 7.49 (1H, d), 7.69 (1H, d), 8.08 (1H, d), 8.16 (1H, d), 8.87 (1H, d); MS m/z (ES⁺) 529 (2M + H⁺) |
| 49 | Prep 34 | —CN | quinolin-6-yl | HCl salt: $\delta_H$ (CD₃OD, 400 MHz) 2.81 (3H, s), 3.30 (1H, br), 4.42 (2H, s), 7.17 (1H, br), 7.82 (1H, br), 8.06 (1H, br), 8.11 (3H, br), 8.39 (1H, br), 9.18 (1H, br), 9.21 (1H, br); MS m/z (ES⁺) 290 (MH⁺) |

[a] —2M Methylamine in MeOH (2 equiv.) and Ti(OⁱPr)₄ (2 equiv.) in EtOH (~0.1 M soln of aldehyde) were used in place of methylamine in EtOH. After isolation of the free base it was converted to the maleate salt by standard methods.

EXAMPLE 50

(2E)-3-{4-(2,3-Dihydro-1-benzothien-6-yloxy)-3-[(dimethylamino)methyl]phenyl}-2-propenamide

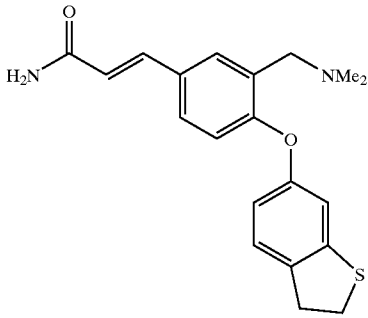

A mixture of the bromide of Example 32 (400 mg, 1.10 mmol), acrylamide (156 mg, 2.19 mmol), triethylamine (0.38 mL, 2.74 mmol), palladium 11 acetate (12.5 mg, 0.06 mmol) and tri-o-tolylphosphine (33.4 mg, 0.11 mmol) in acetonitrile (15 mL) was heated at reflux for 72 h. After cooling to room temperature the solvent was removed in vacuo and the residue was partitioned between EtOAc (50 mL) and 2M HCl (50 mL). The aqueous phase was basified with 2M NaOH and extracted with EtOAc (3×50 mL). The combined basic extracts were dried (MgSO$_4$) and evaporated. The residue was purified by column chromatography [SiO$_2$; 96:4:0.5 (DCM/MeOH/880 NH$_3$) increasing polarity to 90:10:1] to give the title compound (196 mg, 50%) as a beige foam; $\delta_H$ (CDCl$_3$, 400 MHz) 2.28 (6H, s), 3.24 (2H, t), 3.38 (2H, t), 3.51 (2H, s), 5.73 (2H, br), 6.42 (1H, d), 6.69 (1H, dd), 6.82 (2H, m), 7.10 (1H, d), 7.32 (1H, d), 7.60 (1H, d), 7.69 (1H, s); MS m/z (ES$^+$) 355 (MH$^+$).

EXAMPLE 50

3-{4-(2,3-Dihydro-1-benzothien-6-yloxy)-3-[(dimethylamino)methyl]phenyl}propanamide

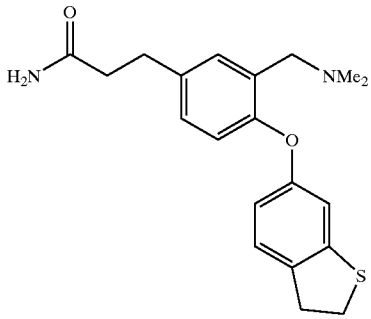

A solution of SmI$_2$ in THF (0.1 M, 21.9 mL, 2.19 mmol) was added to a solution of the alkene of Example 50 (194 mg, 0.55 mmol) in THF (5 mL) under nitrogen followed by water (1 mL). After stirring at room temperature for 10 min the reaction was quenched with 6M NaOH (10 mL) and stirred for 30 min. The organic phase was separated and the aqueous phase was extracted with EtOAc (2×20 mL). The combined organic layers were dried (MgSO$_4$) and evaporated to an oil, which was purified by column chromatography [SiO$_2$; 93:7:1 (DCM/MeOH/880 NH$_3$) increasing polarity to 90:10:1] to give the title compound (90 mg, 46%); $\delta_H$ (CDCl$_3$, 400 MHz) 2.25 (6H, s), 2.54 (2H, t), 2.97 (2H, t), 3.22 (2H, t), 3.36 (2H, t), 3.42 (2H, s), 5.20–5.46 (2H, br), 6.54 (1H, d), 6.73 (1H, s), 6.81 (1H, d), 7.05 (2H, m), 7.31 (1H, s); MS m/z (TS$^+$) 357 (MH$^+$).

Compounds of formula If, i.e. compounds of general formula I where R$^1$ and R$^2$ are methyl, shown in Table 5 were prepared according to Preparation 50 from the precursors indicated.

TABLE 5

(If)

| Example | Precursor | R$^4$ | R$^5$ | Z | data |
|---|---|---|---|---|---|
| 52 | Example 32 | H | —CO$_2$Me | (2,3-dihydrobenzothien-6-yl) | $\delta_H$ (CDCl$_3$, 400 MHz) 2.29 (6H, s), 3.26 (3H, m), 3.39 (2H, m), 3.54 (2H, s), 3.89 (3H, s), 6.62 (1H, d), 6.84 (2H, m) 7.13 (1H, d), 7.86 (1H, d), 8.12 (1H, s); MS m/z (TS$^+$) 344 (MH$^+$) |

TABLE 5-continued

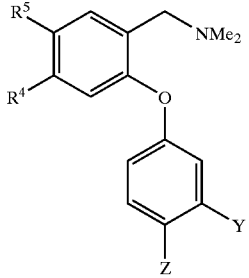

(If)

| Example | Precursor | R⁴ | R⁵ | Z | data |
|---|---|---|---|---|---|
| 53 | Example 33 | —CO₂Me | H | 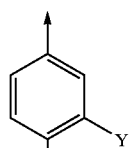 | $\delta_H$ (CDCl₃, 400 MHz) 2.24 (6H, s), 2.33 (3H, s), 2.42 (3H, s), 3.48 (2H, s), 3.82 (3H, s), 6.73 (2H, m), 7.14 (1H, d), 7.50 (1H, s), 7.55 (1H, d), 7.78 (1H, d); MS m/z (TS⁺) 346 (MH⁺) |

Compounds of formula If, i.e. compounds of general formula I where $R^1$ and $R^2$ are methyl, shown in Table 6 were prepared according to Preparation 55 from the precursors indicated.

TABLE 6

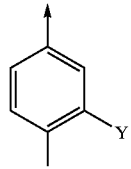

| Example | Precursor | R⁴ | R⁵ | Z | data |
|---|---|---|---|---|---|
| 54 | Example 52 | H | —CO₂H | 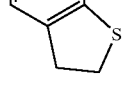 | $\delta_H$ (CD₃OD, 400 MHz) 2.95 (6H, s), 3.29 (2H, m), 3.42 (2H, m), 4.52 (2H, s), 6.80 (1H, d), 6.89 (1H, d), 7.03 (1H, s), 7.29 (1H, d), 8.06 (1H, d), 8.23 (1H, s); MS m/z (TS⁺) 330 (MH⁺) |
| 55 (~80% purity) | Example 55 | —CO₂H | H |  | $\delta_H$ (CD₃OD, 400 MHz) 2.27 (3S, s), 2.42 (3H, s), 2.88 (6H, s), 4.43 (2H, s), 6.95 (2H, m), 7.26 (1H, m), 7.42 (2H, m), 7.72 (1H, m) |

Compounds of formula If, i.e. compounds of general formula I where $R^1$ and $R^2$ are methyl, shown in Table 7 were prepared according to Preparation 59 from the precursors indicated.

TABLE 7

| Example | Precursor | $R^4$ | $R^5$ | Z | data |
|---|---|---|---|---|---|
| 56 | Example 54 | H | —CONH$_2$ | 2,3-dihydrobenzothiophene | $\delta_H$ (CDCl$_3$, 400 MHz) 2.27 (6H, s), 3.25 (2H, m), 3.38 (2H, m), 3.54 (2H, s), 5.90–6.38 (2H, br), 6.59 (1H, d), 6.80 (1H, s), 6.86 (1H, d), 7.11 (1H, d), 7.71 (1H, d), 7.92 (1H, s); MS m/z (TS$^+$) 329 (MH$^+$) |
| 57 | Example 55 | —CONH$_2$ | H | 4-SMe-3-Me-phenyl | HCl salt: $\delta_H$ (CD$_3$OD, 400 MHz) 2.32 (3H, s), 2.43 (3H, s), 2.94 (6H, s), 4.47 (2H, s), 6.98 (2H, br), 7.27 (1H, br), 7.36 (1H, br), 7.62 (1H, br); MS m/z (TS$^+$) 331 (MH$^+$) |

Compounds of formula If, i.e. compounds of general formula I where $R^1$ and $R^2$ are methyl, shown in Table 8 were prepared according to Preparation 69 from the precursors indicated

TABLE 8

| Example | Precursor | $R^4$ | $R^5$ | Z | data |
|---|---|---|---|---|---|
| 58 | Example 52 | H | —CH$_2$OH | 2,3-dihydrobenzothiophene | HCl salt: $\delta_H$ (DMSO-d$_6$, 400 MHz) 2.76 (6H, s), 3.22 (2H, m), 3.40 (2H, m), 4.30 (2H, s), 4.49 (2H, s), 5.27 (1H, br, s), 6.68 (1H, d), 6.83 (1H, d), 6.97 (1H, s), 7.25 (1H, d), 7.37 (1H, d), 7.60 (1H, s), 10.07 (1H, br); MS m/z (TS$^+$) 316 (MH$^+$) |
| 59 | Example 53 | —CH$_2$OH | H | 4-SMe-3-Me-phenyl | HCl salt: $\delta_H$ (CD$_3$OD, 400 MHz) 2.34 (3H, s), 2.46 (3H, s), 2.90 (6H, s), 4.40 (2H, s), 4.55 (2H, s), 6.89 (1H, s), 6.95 (2H, m), 7.18 (1H, d), 7.28 (1H, d), 7.50 (1H, d); MS m/z (TS$^+$) 318 (MH$^+$) |

EXAMPLE 60

4-(2,3-Dihydro-1-benzothien-5-yloxy)-3-[(methylamino)methyl]benzamide

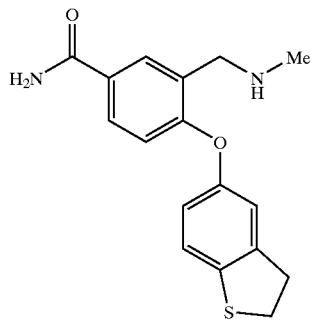

The protected amine of Preparation 59 (317 mg, 0.76 mmol) was dissolved in a saturated solution of HCl in DCM (25 mL) at 0° C. and left for 1 h before being neutralised by the addition of 10% aq $K_2CO_3$ (25 mL). Water (50 mL) was added and the layers were separated. The aqueous layer was extracted with DCM (25 mL) and the combined organic layers were dried ($MgSO_4$) and evaporated. The resulting oil was dissolved in EtOAc (10 mL) and treated with 1M ethereal HCl (1 mL). The white precipitate was collected by filtration and dried in vacuo to give the desired product (211 mg, 77%); $\delta_H$ ($CD_3OD$, 400 MHz) 2.77 (3H, s), 3.35 (2H, obs), 3.39 (2H, t), 4.34 (2H, s), 6.79 (1H, d), 6.90 (1H, dd), 7.02 (1H, s), 7.21 (1H, d), 7.83 (1H, d), 8.00 (1H, s); MS m/z ($TS^+$) 315 ($MH^+$).

Compounds of formula Ig, i.e. compounds of general formula I where $R^1$ and $R^4$ are hydrogen and $R^2$ is methyl, shown in Table 9 were prepared according to Example 60 from the precursors indicated.

TABLE 9

(Ig)

| Ex | Prec | $R^5$ | Z | data |
|---|---|---|---|---|
| 61 | Prep 61 | HN-C(=O)-CH2CH2-OMe | 5-yl-2,3-dihydrobenzothiophene | HCl salt: $\delta_H$ (CDCl$_3$, 400 MHz) 2.77 (3H, d), 3.35 (2H, obs), 3.36 (3H, s), 3.39 (2H, t), 3.51 (4H, s), 4.35 (2H, s), 6.80 (1H, d), 6.90 (1H, dd), 7.01 (1H, s), 7.21 (1H, d), 7.79 (1H, d), 7.96 (1H, s); MS m/z (TS$^+$) 373 (MH$^+$) |
| 62 | Prep 60 | HN-C(=O)-Me | 5-yl-2,3-dihydrobenzothiophene | HCl salt: $\delta_H$ (CD$_3$OD, 400 MHz) 2.77 (3H, s), 2.88 (3H, s), 3.35 (2H, obs), 3.39 (2H, t), 4.35 (2H, s), 6.79 (1H, d), 6.90 (1H, dd), 7.01 (1H, s), 7.20 (1H, d), 7.78 (1H, d), 7.96 (1H, s); MS m/z (TS$^+$) 329 (MH$^+$) |
| 63 | Prep 62 | H$_2$N-C(=O)- | 4-SMe-3-F-phenyl | HCl salt: $\delta_H$ (d$_6$-DMSO, 300 MHz) 2.52 (3H, obs), 2.61 (3H, s), 4.21 (3H, s), 6.90 (1H, d), 7.07 (1H, d), 7.19 (1H, d), 7.40 (1H, brs), 7.48 (1H, t), 7.92 (1H, d), 7.96 (1H, s), 8.21 (1H, s); MS m/z (TS$^+$) 321 (MNH$_4^+$) |

TABLE 9-continued

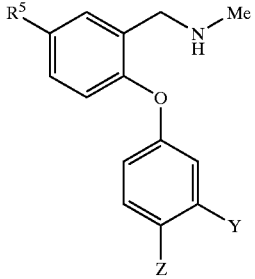

(Ig)

| Ex | Prec | R⁵ | Z | data |
|---|---|---|---|---|
| 64 | Prep 63 | 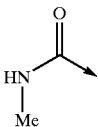 | 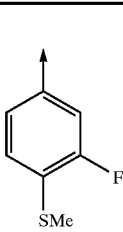 | HCl salt: δ$_H$ (d$_6$-DMSO, 300 MHz) 2.52 (3H, obs), 2.60 (3H, s), 2.79 (3H, d), 4.21 (2H, s), 6.89 (1H, d), 7.07 (1H, d), 7.19 (1H, d), 7.48 (1H, t), 7.85 (1H, d), 8.19 (1H, s), 8.48 (1H, d); MS m/z (TS⁺) 335 (MH⁺) |
| 65 | Prep 64 | 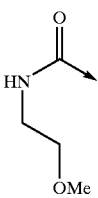 | 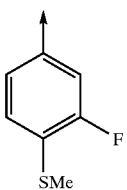 | HCl salt: δ$_H$ (d$_6$-DMSO, 300 MHz) 2.52 (3H, obs), 2.60 (3H, s), 3.27 (3H, s), 3.46 (4H, m), 4.22 (2H, s), 6.91 (1H, d), 7.08 (1H, d), 7.20 (1H, d), 7.50 (1H, t), 7.89 (1H, d), 8.10 (1H, s), 8.58 (1H, brs); MS m/z (TS⁺) 379 (MH⁺) |
| 66 | Prep 65 | 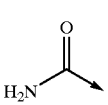 | 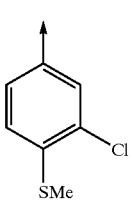 | HCl salt: δ$_H$ (d$_6$-DMSO, 300 MHz) 2.52 (3H, obs), 2.60 (3H, t), 4.11 (2H, s + H$_2$O), 6.82 (1H, d), 7.21 (1H, d), 7.40 (3H, s + d), 7.88 (1H, d), 7.96 (1H, brs), 8.21 (1H, s); MS m/z (ES⁺) 337 (MH⁺) |
| 67 | Prep 66 | 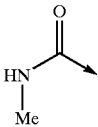 | 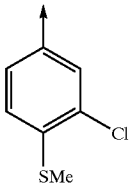 | HCl salt: δ$_H$ (d$_6$-DMSO, 300 MHz) 2.52 (3H, obs), 2.60 (3H, t), 2.79 (3H, d), 4.22 (2H, t), 6.94 (1H, d), 7.22 (1H, d), 7.40 (2H, s + d), 7.83 (1H, d), 8.19 (1H, d), 8.46 (1H, d; MS m/z (ES⁺) 351 (MH⁺) |
| 68 | Prep 67 | 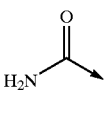 | 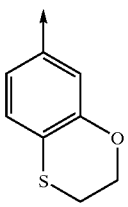 | δ$_H$ (CDCl$_3$, 400 MHz) 2.41 (3H, s), 3.08 (2H, m), 3.80 (2H, s), 4.37 (2H, m), 5.94–6.36 (2H, brd), 6.46 (1H, s), 6.49 (1H, d), 6.81 (1H, d), 6.96 (1H, d), 7.65 (1H, d), 7.86 (1 H, s); MS m/z (TS⁺) 331 (MH⁺) |

TABLE 9-continued (Ig)

| Ex | Prec | R⁵ | Z/Y group | data |
|---|---|---|---|---|
| 69 | Prep 68 | HN(C=O)CH₂CH₂OMe | 2,3-dihydrobenzo[1,4]oxathiine (O up, S down) | HCl salt: δ_H (CDCl₃, 400 MHz) 2.42 (3H, s), 3.08 (2H, m), 3.44–3.50 (4H, m), 3.80 (2H, s), 4.40 (2H, m), 6.45 (1H, s), 6.49 (1H, d), 6.62 (1H, brs), 6.83 (1H, d), 6.96 (1H, d), 7.62 (1H, d), 7.78 (1H, s); MS m/z (TS⁺) 390 (MH⁺) |
| 70 | Prep 70 | HOCH₂– | Y=F, Z=SMe | HCl salt: δ_H (d₆-DMSO, 300 MHz) 2.48 (3H, s), 2.58 (3H, s), 4.12 (2H, s), 4.50 (2H, d), 5.32 (1H, t), 6.92 (2H, m), 7.03 (1H, dd), 7.39 (1H, dd), 7.46 (1H, d), 7.60 (1H, s); MS m/z (TS⁺) 308 (MH⁺) |
| 71 | Prep 69 | HOCH₂– | Y=Cl, Z=SMe | HCl salt: δ_H (d₆-DMSO, 300 MHz) 2.52 (3H, obs), 2.58 (3H, t), 4.10 (2H, s + H₂O), 4.48 (2H, s), 6.94 (1H, d), 7.11 (1H, d), 7.21 (1H, s), 7.25 (2H, m), 7.57 (1H, s); MS m/z (ES⁺) 324 (MH⁺) |
| 72 | Prep 49 | —C≡N | Y=F, Z=SMe | HCl salt: δ_H (d₆-DMSO, 300 MHz) 2.52 (3H, s), 2.60 (3H, s), 4.24 (2H, s), 6.94 (1H, d), 7.04 (1H, d), 7.28 (1H, d), 7.50 (1H, t), 7.86 (1H, d), 8.08 (1H, s); MS m/z (TS⁺) 303 (MH⁺) |

TABLE 9-continued (Ig)

| Ex | Prec | R⁵ | Z | data |
|---|---|---|---|---|
| 73 | Prep 73 | Me-S(=O)(=O)-NH-CH₂- | 3-F, 4-SMe phenyl | HCl salt: δ_H (CDCl₃, 300 MHz) 2.48 (3H, s), 2.64 (3H, s), 2.99 (3H, s), 4.23 (2H, s), 4.30 (2H, d), 6.40 (1H, br), 6.81–6.89 (3H, m), 7.26–7.35 (2H, obs), 7.92 (1H, s); MS m/z (ES⁺) 385 (MH⁺), (ES⁻) 383 (M − H⁺) |
| 74 | Prep 71 | HO-CH₂- | 3-Me, 4-SMe phenyl | HCl salt: δ_H (CD₃OD, 400 MHz) 2.30 (3H, s), 2.44 (3H, s), 2.73 (3H, s), 4.25 (2H, s), 4.59 (2H, s), 6.81 (1H, d), 6.88–6.92 (2H, m), 7.24 (1H, d), 7.37 (1H, d), 7.46 (1H, s); MS m/z (ES⁺) 304 (MH⁺) |
| 75 | Prep 72 | Me-S(=O)(=O)-NH-CH₂- | 3-Me, 4-SMe phenyl | HCl salt: δ_H (CD₃OD, 300 MHz) 2.37 (3H, s), 2.48 (3H, s), 2.78 (3H, s), 2.96 (3H, s), 4.27 (2H, s), 4.31 (2H, s), 6.85 (1H, d), 6.92–7.00 (2H, m), &.31 (1H, d), 7.41 (1H, d), 7.57 (1H, s); MS m/z (ES⁺) 381 (MH⁺), (ES⁻) 379 (M − H⁺) |
| 76 | Prep 75 | CF₃-S(=O)(=O)-NH-CH₂- | 3-Me, 4-SMe phenyl | HCl salt: δ_H (CD₃OD, 400 MHz) 2.29 (3H, s), 2.41 (3H, s), 2.43 (3H, s), 3.76 (2H, s), 4.30 (2H, s), 6.72–6.79 (3H, m), 7.12 (1H, br), 7.27 (2H, obs); MS m/z (ES⁺) 435 (MH⁺), (ES⁻) 433 (M − H⁺) |

EXAMPLE 77

N-{4-[(Dimethylamino)methyl]-3-[3-methyl-4-(methylsulfanyl)phenoxy]benzyl}methanesulfonamide

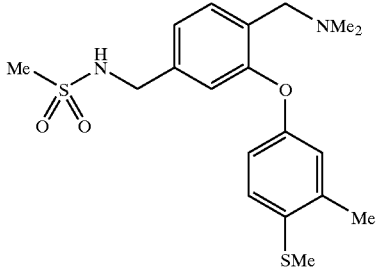

Example 77 was prepared from the Boc protected sulfonamide of Preparation 74 by the method of Example 60; HCl salt: $\delta_H$ (CD$_3$OD, 400 MHz) 2.29 (3H, s), 2.42 (3H, s), 2.82 (3H, s), 2.89 (6H, s), 4.17 (2H, s), 4.39 (2H, s), 6.39 (3H, m), 7.19 (1H, d), 7.48 (1H, d); MS m/z (TS$^+$) 395 (MH$^+$).

EXAMPLE 78

3-[(Methylamino)methyl]-4-[3-methyl-4-(methylsulfanyl)phenoxy]benzonitrile

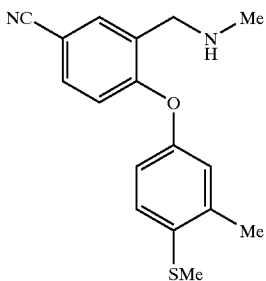

Zn(CN)$_2$ (700 mg, 5.96 mmol) and Pd(PPh$_3$)$_4$ (1.97 g, 1.7 mmol) were added to a solution of the bromide of Example 44 (3.0 g, 8.52 mmol) in DMF (20 mL) and the mixture was heated at 100° C. for 17 h. The reaction was cooled to room temperature, diluted with water (100 mL) and extracted with ether (2×100 mL then 3×50 mL). The combined organic layers were washed with water (3×50 mL), dried (MgSO$_4$) and evaporated to a yellow oil. Initial purification by column chromatography [SiO$_2$; 95:5:0.5 (DCM/MeOH/880 NH$_3$)] was unsuccessful so the material was re-chromatographed [SiO$_2$; 50% pentane in 95:5:0.5 (DCM/MeOH/880 NH$_3$) increasing polarity to 0% pentane] to give the product (1.275 g, 50%) as a pale yellow oil. A sample was taken up in DCM (5 mL) and treated with 1M ethereal HCl to give the HCl salt as a white powder which was collected by filtration; $\delta_H$ (CDCl$_3$, 300 MHz) 2.35 (3H, s), 2.47 (6H, s), 3.88 (2H, s), 6.79 (1H, d), 6.87 (2H, m), 7.20 (1H, d), 7.46 (1H, d), 7.72 (1H, s); MS m/z (TS$^+$) 299 (MH$^+$).

EXAMPLE 79

3-[(Methylamino)methyl]-4-[3-methyl-4-(methylsulfanyl)phenoxy]benzamide

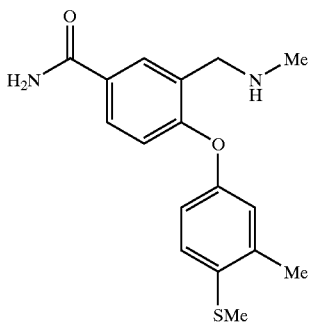

A mixture of the nitrile of Example 78 (404 mg, 1.35 mmol) and KOH (304 mg, 5.42 mmol) in tert-butanol (10 mL) was heated at reflux for 1 h under N$_2$. After cooling to room temperature the solvent was removed in vacuo and the residue was partitioned between water (10 mL) and DCM (10 mL). The aqueous layer was extracted with DCM (4×20 mL) and the combined organic layers were washed with brine, dried (MgSO$_4$) and evaporated. The residue was purified by column chromatography [SiO$_2$; 93:7:1 (DCM/MeOH/880 NH$_3$)] to give the desired product (376 mg, 88%) as a white foam; $\delta_H$ (CDCl$_3$, 300 MHz) 2.35 (3H, s), 2.47 (3H, s), 2.49 (3H, s), 3.88 (2H, s), 5.90–6.30 (2H, brs), 6.82 (3H, m), 7.19 (1H, d), 7.70 (1H, d), 7.90 (1H, s); MS m/z (TS$^+$) 317 (MH$^+$).

Compounds of formula Ih, i.e. compounds of general formula I where R$^1$ and R$^2$ are methyl and R$^4$ is hydrogen, shown in Table 10 where prepared according to Example 12 from the precursors indicated.

TABLE 10

(Ih)

[Structure: A benzene ring with R⁵ at position 5, CH₂NMe₂ ortho to an O linker connecting to a second benzene ring bearing Y and Z substituents. Below, a generic Z-aryl-Y fragment is shown.]

| Example | Precursor | R⁵ | Z [aryl group] | data |
|---|---|---|---|---|
| 80 | Example 60 | H₂N-C(=O)- | 2,3-dihydrobenzothiophen-5-yl | δ_H (CD₃OD, 400 MHz) 2.91 (6H, s), 3.35 (2H, obs), 3.38 (2H, t), 4.45 (2H, s), 6.81 (1H, d), 6.90 (1H, d), 7.03 (1H, s), 7.21 (1H, d), 7.86 (1H, d), 8.03 (1H, s); MS m/z (TS⁺) 329 (MH⁺) |
| 81 | Example 62 | MeHN-C(=O)- | 2,3-dihydrobenzothiophen-5-yl | δ_H (CD₃OD, 400 MHz) 2.90–2.99 (9H, m), 3.35 (2H, obs), 3.43 (2H, t), 4.50 (2H, s), 6.88 (1H, d), 6.97 (1H, d), 7.07 (1H, s), 7.28 (1H, d), 7.85 (1H, d), 8.03 (1H, s); MS m/z (TS⁺) 343 (MH⁺) |
| 82 | Example 61 | MeO(CH₂)₂NH-C(=O)- | 2,3-dihydrobenzothiophen-5-yl | δ_H (CDCl₃, 400 MHz) 2.90 (6H, brm), 3.35 (2H, obs), 3.37 (2H, brm), 3.51 (4H, brm), 4.43 (2H, brs), 6.80–6.94 (2H, brd), 7.01 (1H, brs), 7.20 (1H, brs), 7.82 (1H, brs), 7.98 (1H, brs); MS m/z (TS⁺) 387 (MH⁺) |
| 83 | Example 63 | H₂N-C(=O)- | 3-fluoro-4-methylthiophenyl | δ_H (CDCl₃, 300 MHz) 2.29 (6H, s), 2.47 (3H, s), 3.51 (2H, s), 6.73 (2H, s), 6.97 (1H, d), 7.30 (1H, t), 7.79 (1H, d), 7.97 (1H, s); MS m/z (TS⁺) 335 (MNH₄⁺) |
| 84 | Example 64 | MeHN-C(=O)- | 3-fluoro-4-methylthiophenyl | δ_H (CDCl₃, 300 MHz) 2.29 (6H, s), 2.46 (3H, s), 3.02 (3H, d), 3.54 (2H, s), 6.20 (1H, brs), 6.69 (2H, m), 6.97 (1H, d), 7.30 (1H, t), 7.75 (1H, d), 7.91 (1H, s); MS m/z (TS⁺) 349 (MH⁺) |

TABLE 10-continued

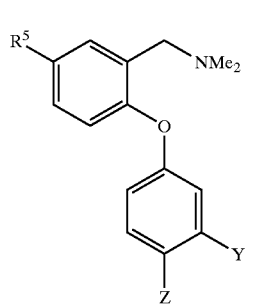

(Ih)

| Example | Precursor | R⁵ | Y / Z | data |
|---|---|---|---|---|
| 85 | Example 65 | HN-C(O)-CH₂CH₂-OMe | Y=F, Z=SMe | HCl salt: δ_H (CDCl₃, 300 MHz) 2.49 (3H, s), 2.94 (6H, s), 3.42 (3H, s), 3.65 (4H, m), 4.33 (2H, s), 6.79 (2H, d), 6.96 (1H, d), 7.35 (1H, t), 7.39 (1H, brs), 7.98 (1H, d), 8.68 (1H, s); MS m/z (TS⁺) 393 (MH⁺) |
| 86 | Example 66 | H₂N-C(O)- | Y=Cl, Z=SMe | δ_H (CDCl₃, 400 MHz) 2.38 (6H, s), 2,47 (3H, s), 3.53 (2H, s), 6.88 (2H, d), 7.03 (1H, s), 7.19 (1H, d), 7.77 (1H, d), 7.95 (1H, s); MS m/z (ES⁺) 351 (MH⁺) |
| 87 | Example 67 | HN(Me)-C(O)- | Y=Cl, Z=SMe | δ_H (CDCl₃, 400 MHz) 2.27 (6H, s), 2.46 (3H, s), 3.01 (3H, d), 3.50 (2H, s), 6.19 (1H, brs), 6.88 (2H, m), 7.00 (1H, s), 7.19 (1H, d), 7.72 (1H, d), 7.85 (1H, s); MS m/z (ES⁺) 365 (MH⁺) |
| 88 | Example 68 | H₂N-C(O)- | benzo[b][1,4]oxathiane | HCl salt: δ_H (CDCl₃, 400 MHz) 2.25 (6H, s), 3.07 (2H, s), 3.49 (2H, s), 4.37 (2H, m), 5.47–6.22 (2H, brd), 6.44 (1H, s), 6.49 (1H, d), 6.86 (1H, d), 6.95 (1H, d), 7.68 (1H, d), 7.87 (1H, s); MS m/z (TS⁺) 346 (MH⁺) |
| 89 | Example 69 | HN-C(O)-CH₂CH₂-OMe | benzo[b][1,4]oxathiane | HCl salt: δ_H (CD₃OD, 400 MHz) 2.91 (6H, s), 3.13 (2H, s), 3.27 (3H, s), 4.39 (2H, s), 4.46 (2H, s), 6.64 (2H, s + d), 6.87 (1H, d), 7.08 (1H, d), 7.95 (1H, d), 8.00 (1H, s); MS m/z (TS⁺) 403 (MH⁺) |

TABLE 10-continued

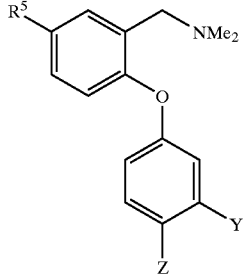

(Ih)

| Example | Precursor | R⁵ | Z | data |
|---|---|---|---|---|
| 90 | Example 70 | HO⟋ | 3-F, 4-SMe phenyl | HCl salt: δ_H (d_6-DMSO, 300 MHz) 2.46 (3H, s), 2.74 (6H, s), 4.29 (2H, s), 4.51 (2H, s), 5.32 (1H, brs), 6.93 (2H, d), 7.08 (1H, d), 7.41 (2H, m), 7.63 (1H, 5); MS m/z (TS⁺) 322 (MH⁺) |
| 91 | Example 71 | HO⟋ | 3-Cl, 4-SMe phenyl | HCl salt: δ_H (d_6-DMSO, 400 MHz) 2.52 (3H, obs), 2.76 (6H, s), 4.09 (2H, s), 4.49 (2H, s), 5.32 (1H, brs), 6.87 (1H, d), 7.08 (1H, d), 7.26 (1H, s), 7.38 (2H, m), 7.60 (1H, s); MS m/z (ES⁺) 338 (MH⁺) |
| 92 | Example 78 | —C≡N | 3-Me, 4-SMe phenyl | HCl salt: δ_H (CDCl_3, 400 MHz) 2.35 (3H, s), 2.48 (3H, s), 2.87 (6H, d), 4.39 (2H, d), 6.85 (1H, d), 6.90 (1H, d), 6.93 (1H, dd), 7.21 (1H, d), 7.60 (1H, d), 8.17 (1H, s); MS m/z (TS⁺) 313 (MH⁺) |
| 93 | Example 72 | —C≡N | 3-F, 4-SMe phenyl | HCl salt: δ_H (d_6-DMSO, 300 MHz) 2.49 (3H, obs), 2.79 (6H, s), 4.41 (2H, s), 6.97 (1H, d), 7.14 (1H, d), 7.32 (1H, d), 7.49 (1H, t), 7.87 (1H, d), 8.22 (1H, s); MS m/z (TS⁺) 317 (MH⁺) |
| 94 | Example 45 | H | 3-Me, 4-SMe phenyl | HCl salt: δ_H (d_6-DMSO, 400 MHz) 2.23 (3H, s), 2.42 (3H, s), 2.76 (6H, s), 4.34 (2H, s), 6.80 (1H, d), 7.97 (1H, dd), 7.00 (1H, s), 7.19 (1H, t), 7.24 (1H, d), 7.40 (1H, t), 7.67 (1H, d); MS m/z (ES⁺) 288 (MH⁺) |

TABLE 10-continued

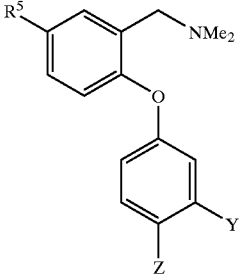

(Ih)

| Example | Precursor | R[5] | Z | data |
|---|---|---|---|---|
| 95 | Example 46 | H | 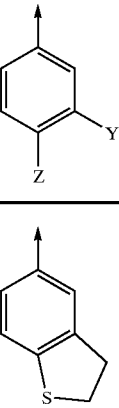 | HCl salt: $\delta_H$ (CDCl$_3$, 400 MHz) 2.74 (6H, s), 3.22 (2H, m), 3.38 (2H, m), 4.26 (2H, s), 6.71 (1H, d), 6.80 (2H, brm), 7.15 (2H, brm), 7.32 (1H, d), 7.79 (2H, d); MS m/z (ES$^+$) 286 (MH$^+$) |
| 96 | Example 73 | 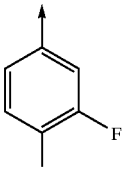 | 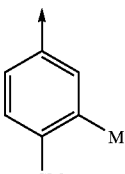 | HCl salt: $\delta_H$ (CD$_3$OD, 300 MHz) 2.46 (3H, s), 3.93 (6H, s), 3.97 (3H, s), 4.24 (2H, s), 4.42 (2H, s), 6.91–7.00 (3H, m), 7.41–7.54 (2H, m), 7.61 (1H, s); MS m/z (TS$^+$) 399 (MH$^+$), (ES$^-$) 397 (M − H$^+$) |
| 97 | Example 75 | 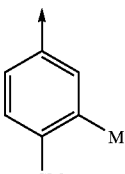 | 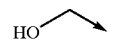 | HCl salt: $\delta_H$ (CD$_3$OD, 400 MHz) 2.31 (3H, s), 2.43 (3H, s), 2.86–2.94 (9H, m), 4.22 (2H, s), 4.39 (2H, s), 6.83 (1H, d) 6.89–6.94 (2H, m), 7.26 (1H, d), 7.40 (1H, d), 7.54 (1H, s); MS m/z (ES$^-$) 393 (M − H$^+$) |
| 98 | Example 74 | HO⌒ | 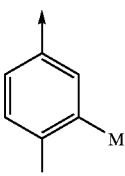 | HCl salt: $\delta_H$ (CD$_3$OD, 300 MHz) 2.36 (3H, s), 2.47 (3H, s), 2.98 (6H, s), 4.43 (2H, s), 4.63 (2H, s), 6.89 (1H, d), 6.91–7.00 (2H, m), 7.30 (1H, d), 7.43 (1H, d), 7.55 (1H, s); MS m/z (ES$^+$) 318 (MH$^+$) |

TABLE 10-continued (Ih)

[Structure: R5 group on benzene ring with CH2NMe2 substituent, connected via O to another benzene ring bearing Y and Z substituents]

| Example | Precursor | R⁵ | Z | data |
|---------|-----------|-----|---|------|
| 99 | Example 76 | CF₃-S(=O)(=O)-N(H)-CH₂- | [3-Me, 4-SMe phenyl] | HCl salt: $\delta_H$ (CD$_3$OD, 300 MHz) 2.39 (3H, s), 2.47 (3H, s), 2.85 (6H, s), 4.32 (2H, s), 4.44 (2H, s), 6.80–6.86 (3H, m), 7.21 (1H, d), 7.35 (1H, d), 8.08 (1H, s); MS m/z (ES⁺) 449 (MH⁺), (ES⁻) 447 (M − H⁺) |
| 100 | Example 102 | H₂N-C(=O)-CH₂- | [quinolin-6-yl] | $\delta_H$ (CD$_3$OD, 400 MHz) 2.26 (6H, s), 3.58 (2H, s), 6.97 (1H, d), 7.35 (1H, d), 7.46 (1H, dd), 7.54 (1H, d), 7.80 (1H, d), 8.03 (2H, m), 8.20 (1H, d), 8.74 (1H, d); MS m/z (TS⁺) 322 (MH⁺) |

Example 94 was Also Prepared as Follows

A solution of the product from Preparation 30 (200 g, 0.78 mol) in DCM (1.4 L) was added to THF (1.4 L). To this mixture was added dimethylamine hydrochloride (69.5 g, 0.85 mol) and triethylamine (235 g, 2.33 mol) successively. The temperature was adjusted to 20° C. and after 3 h sodium triacetoxyborohydride (246 g, 1.16 mol) was added (After 20 h, if the reaction has completed, continue with work up; otherwise see note below). Dichloromethane (2 L) was added and a solution of 8% sodium bicarbonate (0.9 L) was added over 0.5 h. The layers were separated and the organic layer washed with water (1 L). The layers were again separated and the organic layer was concentrated. Ethyl acetate (0.27 L) was added and the solvent removed replacing with fresh ethyl acetate (800 ml). The solution was then cooled to below 5° C. and 7.02 M HCl/IPA (0.117 L, 0.82 mol) added whist the temperature was maintained below 10° C. After stirring for 1 h at below 5° C., the slurry was filtered, washed with ethyl acetate (3×0.2 L) and dried in a vacuum oven at 50° C. overnight to give the desired product as a powdery solid (141.5 g, 56%). [Note: if reaction hasn't completed after 20 h. Add another portion of dimethylamine hydrochloride (13 g, 0.16 mol) and triethylamine (43.4 g, 0.43 mol) successively. After 2 h at room temperature add sodium triacetoxyborohydride (46 g, 0.22 mol). Leave for a further 20 h and then work up as above].

Compounds of formula Ii, i.e. compounds of general formula I where R² is methyl, R⁴ is hydrogen and R⁵ is —C(=O)NH₂, shown in Table 11 were prepared according to Example 79 form the precursors indicated.

TABLE 11

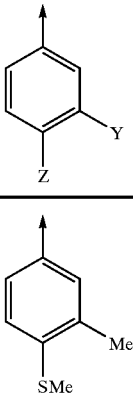

| Example | Precursor | R¹ | Z | data |
|---|---|---|---|---|
| 101 | Example 92 | Me | (3-Me-4-SMe-phenyl) | $\delta_H$ (CDCl$_3$, 300 MHz) 2.30 (6H, s), 2.35 (3H, s), 2.46 (3H, s), 3.58 (2H, s), 5.60–5.80 (1H, brs), 6.00–6.20 (1H, brs), 6.32 (3H, m), 7.19 (1H, m), 7.71 (1H, d), 7.90 (1H, s); MS m/z (TS$^+$) 331 (MH$^+$) |
| 102 | Example 49 | H | (quinolin-6-yl) | $\delta_H$ (CDCl$_3$, 400 MHz) 2.43 (3H, s), 3.84 (2H, s), 6.94 (1H, d), 7.20 (1H, d), 7.34–7.39 (1H, m), 7.43 (1H, dd), 7.70 (1H, d), 7.91 (1H, s), 7.99 (1H, d), 8.09 (1H, d), 8.82 (1H, d); MS m/z (ES$^+$) 309 (MH$^+$) |

EXAMPLE 103

N-{5-Amino-2-[3-methyl-4-(methylsulfanyl)phenoxy]benzyl}-N,N-dimethylamine

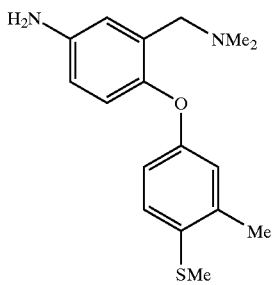

A mixture of the nitro compound of Example 27 (2.0 g, 6 mmol), Fe powder (2.51 g, 44.9 mmol) and CaCl$_2$ (300 mg, 2.7 mmol) in EtOH (20 mL) and water (4 mL) was heated at reflux for 20 h. After cooling to room temperature the solvent was removed in vacuo and the residue was partitioned between brine (100 mL) and ether (100 mL). The aqueous layer was extracted with ether (50 mL) and the combined organic layers were dried (MgSO$_4$) and evaporated to give the product (1.47 g, 81%) as an orange oil; $\delta_H$ (CDCl$_3$, 300 MHz) 2.22 (6H, s), 2.32 (3H, s), 2.40 (3H, s), 3.33 (2H, s), 6.59 (1H, dd), 6.60–6.75 (2H, m), 6.78 (1H, dd), 6.94 (1H, s), 7.10–7.20 (3H, m); MS m/z (ES$^+$) 303 (MH$^+$).

EXAMPLE 104

N-[5-Amino-2-(2,3-dihydro-1-benzothien-5-yloxy)benzyl]-N,N-dimethylamine

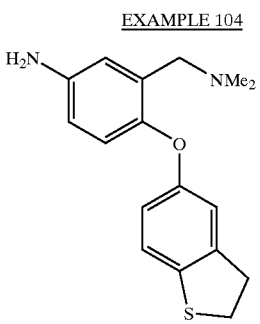

N-[5-Amino-2-(2,3-dihydro-1-benzothien-5-yloxy)benzyl]-N,N-dimethylamine

The title compound was prepared from the nitro compound of Example 28 by the method of Example 103; $\delta_H$ (CDCl$_3$, 400 MHz) 2.20 (6H, s), 3.16 (2H, t), 3.30 (4H, m), 3.54 (2H, br), 6.53 (1H, dd), 6.60 (1H, d), 6.71 (2H, m), 6.79 (1H, d), 7.01 (1H, d); MS m/z (ES$^+$) 301 (MH$^+$).

EXAMPLE 105
N-[3-(Aminomethyl)-4-(2,3-dihydro-1,4-benzoxathiin-6-yloxy)phenyl]-methanesulfonamide

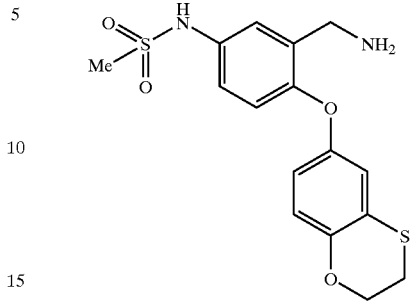

The nitrile of Preparation 95 (720 mg, 1.99 mmol) was dissolved in a 1M solution of BH$_3$.THF in THF (10 mL, 10 mmol) and the mixture was heated at reflux for 3 h. After cooling to room temperature the reaction was quenched by the cautious addition of MeOH (10 mL). The solvent was evaporated, the residue was treated with 6M HCl (10 mL) and heated at reflux for 1 h. After cooling, the mixture was basified with 2M NaOH and the pH was adjusted to 7 with sat aq NH$_4$Cl. The mixture was extracted with EtOAc (3×50 mL) and DCM (2×50 mL) and the combined organic layers were dried (MgSO$_4$) and evaporated to give a beige foam (685 mg, 94%) which was used without further purification; $\delta_H$ (CDCl$_3$, 400 MHz) 3.00 (3H, s), 3.13 (2H, m), 3.87 (2H, s), 4.40 (2H, m), 6.62 (1H, d), 6.67 (1H, s), 6.79 (2H, d), 7.08 (1H, d), 7.25 (1H, d); MS m/z (TS$^+$) 367 (MH$^+$).

Compounds of formula Ij, i.e. compounds of general formula I where R$^1$, R$^2$ and R$^4$ are hydrogen and R$^5$ is —NR$^8$—SO$_2$Me, shown in Table 12 were prepared according to Example 105 from the precursors indicated

TABLE 12

(Ij)

| Example | Precursor | Z, Y structure | R$^8$ | data |
|---|---|---|---|---|
| 106 | Prep 96 | Y=Cl, Z=SMe | H | $\delta_H$ (CDCl$_3$, 300 MHz) 2.47 (3H, s), 3.02 (3H, s), 3.08 (3H, br), 3.85 (2H, s), 6.87 (2H, m), 6.99 (1H, d), 7.15 (1H, dd), 7.20 (1H, d), 7.30 (1H, d); MS m/z (ES$^-$) 371 (M − H$^+$) |

TABLE 12-continued (Ij)

[Structure: Methanesulfonamide-substituted phenyl with R8-N, CH2NH2, phenoxy linker to phenyl with Y and Z substituents]

| Example | Precursor | Z / Y structure | R8 | data |
|---|---|---|---|---|
| 107 | Prep 97 | Y=F, Z=SMe | H | Used crude in a subsequent step: $\delta_H$ (CD$_3$OD, 400 MHz) 2.37 (3H, s), 2.95 (3H, s), 3.75 (2H, s), 6.58 (1H, d), 6.71 (2H, m), 6.89 (1H, d), 7.15 (1H, dd), 7.28 (1H, obs) |
| 108 | Prep 100 | Y=Me, Z=SMe | Me | Used crude in a subsequent step: $\delta_H$ (CDCl$_3$, 300 MHz) 2.36 (3H, s), 2.46 3H, s), 2.90 (3H, s), 3.36 (3H, s), 3.93 (2H, s), 6.83 (3H, m), 7.20 (2H, m), 7.42 (1H, d). |
| 109 | Prep 99 | Y=SMe, Z=Me | H | $\delta_H$ (CD$_3$OD, 400 MHz) 2.24 (3H, s), 2.40 (3H, s), 2.97 (3H, s), 3.80 (2H, s), 6.60 (1H, d), 6.81–6.87 (2H, m), 7.08–7.17 (2H, m), 7.29 (1H, d); MS m/z (ES$^+$) 353 (MH$^+$), (ES$^-$) 351 (M − H$^+$) |

EXAMPLE 110

N-{4-(2,3-Dihydro-1,4-benzoxathiin-6-yloxy)-3-[(methylamino)methyl]phenyl}-methanesulfonamide

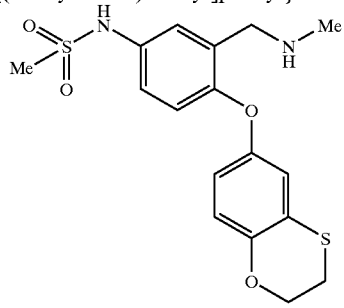

Dicyclohexylcarbodiimide (460 mg, 2.23 mmol) was added to a solution of pentafluorophenol (413 mg, 2.24 mmol) in ether (10 mL) followed by formic acid (95 μL, 2.5 mmol). The mixture was stirred for 2 h and then filtered, washing the residue with ether. The filtrate was concentrated to ~5 mL and a solution of the primary amine of Example 105 (411 mg, 1.1 mmol) in DCM (10 mL) was added. The mixture was stirred for 16 h then concentrated to an oily residue. This crude oil was taken up in a solution of BH$_3$.THF in THF (1M, 20 mL, 20 mmol) and heated at reflux for 1.5 h under N$_2$. After cooling to room temperature the reaction was quenched by the cautious addition of MeOH (10 mL) and then concentrated in vacuo. The oily residue was treated with 6M HCl and heated at reflux for 30 min. After cooling to room temperature the mixture was basified with aq K$_2$CO$_3$ and extracted with DCM (3×). The combined organic extracts were dried (MgSO$_4$) and evaporated. The residue was purified by column chromatography [SiO$_2$; 90:10:1 (DCM/MeOH/880 NH$_3$)] to give a colourless oil which was taken up in EtOAc (20 mL) and treated with 1M ethereal HCl (2 mL). After stirring for 1.5 h the solid was collected by filtration to give the title product (282 mg, 60%); δ_H (CD_3OD, 400 MHz) 2.78 (3H, s), 2.98 (3H, s), 3.18 (2H, m), 4.29 (2H, s), 4.39 (2H, m), 6.74 (1H, d), 6.80–6.90 (3H, m), 7.22 (1H, d), 7.44 (1H, s); MS m/z (TS+) 381 (MH+).

Compounds of formula Ik, i.e. compounds of general formula I where $R^1$ and $R^4$ are hydrogen, $R^2$ is methyl and $R^5$ is —NHSO_2Me, shown in Table 13 were prepared according to Example 110 from the precursors indicated.

TABLE 13

(Ik)

| Example | Precursor | | data |
|---|---|---|---|
| 111 | Example 107 | 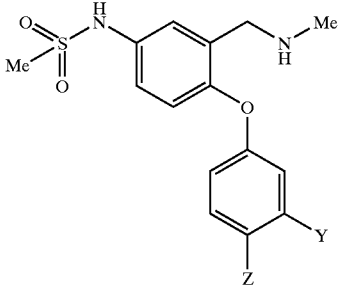 | δ_H (CDCl_3, 400 MHz) 2.40 (6H, s), 2.99 (3H, s), 3.70 (2H, s), 6.64 (2H, t), 6.88 (1H, d), 7.15 (1H, d), 7.25 (2H, s); MS m/z (TS+) 371 (MH+) |
| 112 | Example 106 | 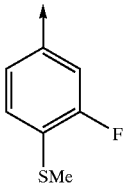 | HCl salt: δ_H (CD_3OD, 400 MHz) 2.55 (3H, s), 3.82 (3H, s), 3.04 (3H, s), 4.32 (2H, s), 6.97 (1H, d), 7.11 (1H, d), 7.23 (1H, s), 7.30 (1H, d), 7.39 (1H, d), 7.56 (1H, s); MS m/z (TS+) 387 (MH+) |
| 113 | Example 109 | 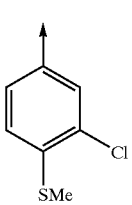 | HCl salt: δ_H (CD_3OD, 400 MHz) 2.24 (3H, s), 2.39 (3H, s), 2.76 (3H, s), 2.93 (3H, s), 4.25 (2H, s), 6.69 (1H, d), 6.82 (1H, d), 6.93 (1H, s), 7.17 (1H, d), 7.21 (1H, d), 7.43 (1H, s); MS m/z (ES+) 367 (MH+), (ES−) 365 (M − H+) |

Compounds of formula Im, i.e. compounds of general formula I where $R^1$ and $R^4$ are hydrogen, $R^2$ is methyl and $R^5$ is —$NR^8SO_2Me$, shown in Table 14 were prepared according to Example 110 from the precursors indicated.

TABLE 14

(Im)

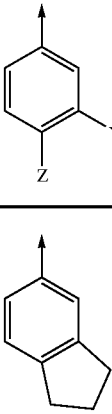

| Example | Precursor | $R^8$ | (Y/Z aryl) | data |
|---|---|---|---|---|
| 114 | Prep 85 | H | 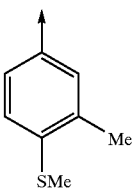 | HCl salt: $\delta_H$ (CDCl$_3$, 400 MHz) 2.09 (2H, m), 2.73 (3H, s), 2.88 (4H, t), 3.00 (3H, s), 4.21 (2H, s), 6.80 (2H, m), 6.88 (1H, s), 7.19 (1H, d), 7.34 (1H, d), 7.75 (1H, s); MS m/z (TS$^+$) 347 (MH$^+$) |
| 115 | Prep 84 | H | (3-Me, 4-SMe phenyl) | HCl salt: $\delta_H$ (d$_6$-DMSO, 400 MHz) 2.20 (3H, s), 2.40 (3H, s), 2.55 (3H, s), 2.97 (3H, s), 4.08 (2H, s), 6.80 (1H, d), 6.87 (1H, d), 6.91 (1H, s), 7.14 (1H, d), 7.20 (1H, d), 7.39 (1H, s); MS m/z (TS$^+$) 367 (MH$^+$) |
| 116$^a$ | Prep 88 | Me | (3-Me, 4-SMe phenyl) | $\delta_H$ (CDCl$_3$, 300 MHz) 2.17 (3H, s), 2, 37 (3H, s), 2.48 (3H, s), 2.62 (3H, s), 2.97 (3H, s), 3.34 (3H, s), 4.23 (2H, s), 6.79 (1H, d), 6.94 (2H, s), 7.35 (2H, m), 7.81 (1H, s); MS m/z (TS$^+$) 381 (MH$^+$) |

TABLE 14-continued
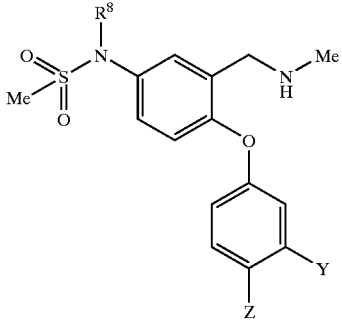
(Im)
| Example | Precursor | R⁸ | Z 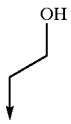 Y | data |
|---|---|---|---|---|
| 117 | Prep 89 | OH-CH2CH2- | Me, SMe | HCl salt: $\delta_H$ (CDCl₃, 400 MHz) 2.29 (3H, s), 2.39 (3H, s), 2.42 (3H, s), 2.94 (3H, s), 3.60 (2H, t), 3.74 (2H, t), 3.79 (2H, s), 6.78 (3H, m), 7.14 (2H, m), 7.41 (1H, s); MS m/z (TS⁺) 410 (MH⁺) |
| 118 | Prep 87 | H | 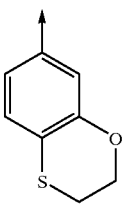 | $\delta_H$ (CDCl₃, 400 MHz) 2.42 (3H, s), 2.58–2.79 (2H, br), 2.94 (3H, s), 3.08 (2H, m), 3.71 (2H, s), 4.38 (2H, m), 6.39 (1H, s), 6.47 (1H, d), 6.82 (1H, d), 6.94 (1H, d), 7.07 (1H, d), 7.18 (1H, s); MS m/z (TS⁺) 381 (MH⁺) |
| 119 | Prep 86 | H | 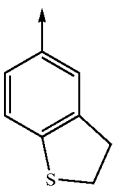 | $\delta_H$ (CD₃OD, 400 MHz) 2.80 (3H, s), 3.00 (3H, s), 3.27 (2H, m), 3.40 (2H, m), 4.28 (2H, m), 6.85 (2H, m), 7.00 (1H, s), 7.20 (1H, d), 7.24 (1H, dd), 7.47 (1H, d); MS m/z (TS⁺) 365 (MH⁺) |
ᵃ—Also made from Example 108 by the method of Example 110.

Compounds of formula In, i.e. compounds of general formula I where R¹ and R² are methyl, R⁴ is hydrogen, and R⁵ is —NR⁸SO₂Me, shown in Table 15 were prepared according to Example 12 from the precursors indicated.

TABLE 15

(In)

[Structure: phenyl ring with N(R⁸)SO₂Me group, CH₂NMe₂ substituent, and O-linked to a second phenyl ring bearing Y and Z substituents]

| Example | Precursor | R⁸ | Y/Z aryl | Data |
|---|---|---|---|---|
| 120 | Example 111 | H | 3-F, 4-SMe phenyl | HCl salt: $\delta_H$ (CD₃OD, 400 MHz) 2.42 (3H, s), 2.89 (6H, s), 2.98 (3H, s), 4.37 (2H, s), 6.88 (2H, m), 6.97 (1H, d), 7.28 (1H, d), 7.39 (1H, t), 7.48 (1H, s); MS m/z (TS⁺) 385 (MH⁺) |
| 121 (from primary amine) | Example 105 | H | 2,3-dihydro-1,4-benzoxathiine-6-yl | $\delta_H$ (CDCl₃, 400 MHz) 3.00 (3H, s), 3.13 (2H, m), 3.87 (2H, s), 4.40 (2H, m), 6.62 (1H, d), 6.67 (1H, s), 6.79 (2H, d), 7.08 (1H, d), 7.25 (1H, d); MS m/z (TS⁺) 367 (MH⁺) |
| 122 (from primary amine) | Example 106 | H | 3-Cl, 4-SMe phenyl | HCl salt: $\delta_H$ (CD₃OD, 400 MHz) 2.49 (3H, s), 2.93 (6H, s), 3.00 (3H, s), 4.41 (2H, s), 6.95 (1H, d), 7.07 (1H, d), 7.21 (1H, s), 7.33 (2H, m), 7.54 (1H, s); MS m/z (TS⁺) 395 (MH⁺) |
| 123 | Example 114 | H | indan-5-yl | HCl salt: $\delta_H$ (CDCl₃, 400 MHz) 2.12 (2H, m), 2.81 (6H, s), 2.91 (4H, t), 3.13 (3H, s), 4.25 (2H, s), 6.73 (1H, d), 6.83 (2H, m), 7.10 (1H, d), 7.39 (1H, d), 7.90 (1H, s); MS m/z (TS⁺) 360 (MH⁺) |

TABLE 15-continued (In)

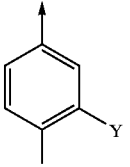

| Example | Precursor | R[8] | Z | Data |
|---|---|---|---|---|
| 124 | Example 118 | H | (benzodioxine-thio structure) | δ$_H$ (CDCl$_3$, 400 MHz) 2.22 (6H, s), 2.98 (3H, s), 3.07 (2H, m), 3.41 (2H, s), 4.38 (2H, m), 6.36 (1H, s), 6.45 (1H, d), 6.86 (1H, d), 6.92 (1H, d), 7.12 (1H, d), 7.27 (1H, s); MS m/z (TS$^+$) 395 (MH$^+$) |
| 125 | Example 117 | OH (CH$_2$CH$_2$OH) | Me / SMe substituted phenyl | HCl salt: δ$_H$ (CDCl$_3$, 300 MHz) 2.38 (3H, s), 2.48 (3H, s), 2.86 (6H, brs), 3.15 (3H, s), 3.73 (2H, brs), 3.87 (2H, brs), 4.35 (2H, brs), 6.82 (3H, brs), 7.20 (2H, m), 7.41 (1H, d); MS m/z (TS$^+$) 425 (MH$^+$) |
| 126 (from primary amine) | Example 108 | Me | Me / SMe substituted phenyl | HCl salt: δ$_H$ (CD$_3$OD, 400 MHz) 2.29 (3H, s), 2.43 (3H, s), 2.89 (3H, s), 2.91 (6H, s), 3.26 (3H, s), 4.42 (2H, s), 6.84 (1H, d), 6.97 (2H, m), 7.27 (1H, d), 7.47 (1H, dd), 7.60 (1H, d); MS m/z (TS$^+$) 395 (MH$^+$) |
| 127 (from primary amine) | Example 109 | H | SMe / Me substituted phenyl | HCl salt: δ$_H$ (CD$_3$OD, 400 MHz) 2.27 (3H, s), 2.42 (3H, s), 2.94 (6H, s), 2.99 (3H, s), 4.42 (2H, s), 6.77 (1H, d), 6.89 (1H, d), 6.99 (1H, s), 7.19 (1H, d), 7.28 (1H, dd), 7.50 (1H, s); MS m/z (TS$^+$) 381 (MH$^+$), (ES$^+$) 381 (MH$^+$), (ES$^-$) 379 (M − H$^+$) |

EXAMPLE 128

N-{3-[(Dimethylamino)methyl]-4-[3-methyl-4-(methylsulfanyl)phenoxy]-phenyl}methanesulfonamide

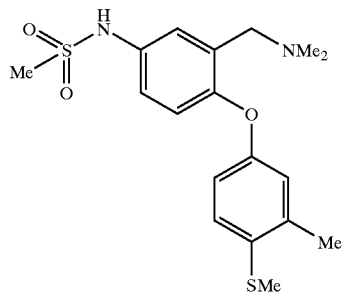

Methanesulfonyl chloride (371 μL, 4.79 mmol) was added to a solution of the aniline of Example 103 (725 mg, 2.4 mmol) and Et₃N (1 mL, 7.17 mmol) in DCM (10 mL) at 0° C. After stirring at 0° C. for 1 h the reaction was allowed to warm to room temperature before the solvent was removed in vacuo. 2M NaOH (10 mL) was added to the residue and the mixture was stirred overnight. The resulting clear solution was neutralised by the addition of sat aq $NH_4Cl$ and extracted with DCM (2×30 mL). The combined organic layers were dried ($MgSO_4$) and evaporated to give an oil. This was taken up in EtOAc (10 mL), the HCl salt was precipitated by the addition of 1M ethereal HCl and the product (669 mg, 67%) was collected by filtration; $\delta_H$ (d₆-DMSO, 400 MHz) 2.23 (3H, s), 2.42 (3H, s), 2.75 (6H, s), 3.04 (3H, s), 4.38 (2H, s), 6.84 (1H, d), 6.93 (1H, d), 6.98 (1H, s), 7.17–7.25 (2H, m), 7.50 (1H, s); MS m/z (ES⁺) 381 (MH⁺).

Compounds of formula Ip, i.e. compounds of general formula I where $R^1$ and $R^2$ are methyl, $R^4$ is hydrogen, and $R^5$ is —$NHSO_2R^9$, shown in Table 16 were prepared according to Example 128 from the precursors indicated.

TABLE 16

(Ip)

| Example | Precursor | $R^9$ | Z | data |
|---|---|---|---|---|
| 129 | Example 104 | Me | (2,3-dihydrobenzothiophen-5-yl) | HCl salt: $\delta_H$ (CD₃OD, 400 MHz) 2.92 (6H, s), 2.99 (3H, s), 3.26 (2H, t), 3.40 (2H, t), 4.41 (2H, s), 6.88 (2H, d), 7.00 (1H, s), 7.10 (1H, d), 7.27 (1H, d), 7.50 (1H, s); MS m/z (TS⁺) 381 (MH⁺) |
| 130 | Example 103 | Et | (3-methyl-4-methylsulfanylphenyl) | HCl salt: $\delta_H$ (d₆-DMSO, 400 MHz) 1.21 (3H, t), 2.23 (3H, s), 2.42 (3H, s), 2.74 (6H, s), 3.16 (2H, q), 4.26 (2H, s), 6.92 (1H, d), 6.92 (1H, d), 6.98 (1H, s), 7.18–7.25 (2H, m), 7.51 (1H, s); MS m/z (ES⁺) 395 (MH⁺) |

Peparations

Preparation 1

5-(Aminosulfonyl)-2-fluoro-N-methylbenzamide

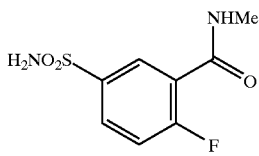

To a solution of 5-(aminosulfonyl)-2-fluorobenzoic acid [prepared according to Chem. Pharm. Bull. 1995, 43, 582–7] (22.98 g, 105 mmol) in THF (500 mL) at room temperature under nitrogen was added carbonyldiimidazole (17 g, 105 mmol). After stirring for 2.25 h a solution of methylamine in THF (2M, 70 mL, 140 mmol) was added dropwise and the reaction was allowed to stir for 18 h. The crude reaction mixture was concentrated to a low volume and EtOAc (150 mL) was added to the resulting thick oil. This mixture was stirred and a granular precipitate formed which was collected by filtration. This crude product, contaminated with imidazole, was suspended in DCM (300 mL) and heated at reflux for 5 h. After cooling to room temperature the mixture was filtered to give the desired product (19.8 g, 81%) containing <2% w/w imidazole; $^1$H NMR $\delta_H$ (300 MHz, $d_4$-MeOH) 2.97 (3H, s), 7.40 (1H, t), 8.05 (1H, m), 8.29 (1H, d); MS m/z (TS$^+$) 250 (MNH$_4^+$).

Preparation 2

3-Chloro-4-(methylsulfanyl)phenol

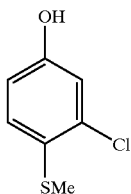

(i) Preparation of 2-chloro-1-(methylsulfanyl)-4-nitrobenzene

To a solution of 4-fluoro-3-chloronitrobenzene (27 g, 156 mmol) in DMF (150 mL) at room temperature was added 5-tert-butyl-4-hydroxy-2-methylphenyl sulfide (100 mg) followed by sodium thiomethoxide (NaSMe) (10 g, 143 mmol) and the reaction was stirred for 6 h. The DMF was removed in vacuo and the residue was partitioned between ether (1 L) and water (1 L). The ether layer was washed with water (1 L) and brine (1 L), dried (MgSO$_4$) and the solvent was removed under reduced pressure. The residue was purified by column chromatography (SiO$_2$; DCM: pentane 1:5 increasing polarity to 3:7) to give the title compound (15.22 g, 49%) as a yellow solid; $\delta_H$ (400 MHz, CDCl$_3$) 2.53 (3H, s), 7.20 (1H, d), 8.09 (1H, dd), 8.20 (1H, d).

(ii) Preparation of 3-chloro-4-(methylsulfanyl)aniline

To a mixture of the above compound (14.08 g, 69 mmol) in acetic acid (300 mL) and water (60 mL) was added Fe powder (23 g, 412 mmol) and the reaction mixture was swirled until all the starting material had dissolved. The mixture was left to stand for 1.5 h and the acetic acid was then removed under reduced pressure. The residue was taken up in sat NaHCO$_3$ (aq) (500 mL) and EtOAc (500 mL) and filtered through Arbocel®. The layers were separated, the aqueous phase was extracted with EtOAc (300 mL) and the combined organics were washed with brine, dried (MgSO$_4$) and the solvent was removed in vacuo to give the title compound (11.52 g, 96%) as a beige solid; $\delta_H$ (400 MHz, CDCl$_3$) 2.38 (3H, s), 3.66 (2H, br), 6.53 (1H, dd), 6.70 (1H, d), 7.12 (1H, d); MS m/z (ES$^+$) 174 (MH$^+$).

(iii) Preparation of 3-chloro-4-(methylsulfanyl)phenol

The above aniline (11.5 g, 66.2 mmol) was dissolved in the minimum THF (~15 mL) and water (500 mL) was added with vigorous stirring, followed by conc H$_2$SO$_4$ (25 mL). The mixture was cooled in an ice-water bath and a solution of NaNO$_2$ (5.0 g, 72.5 mmol) in iced water (10 mL), was added via pipette under the surface of the reaction mixture. The reaction was stirred at 0° C. for 1.5 h and the resulting yellow/brown solution was decanted from the remaining solid into a dropping funnel containing ice (~200 g). This solution was added at a steady rate over 7 min to a vigorously stirred mixture of Cu(NO$_3$)$_2$ (230 g, 0.99 mol) and Cu$_2$O (8.52 g, 67.4 mmol) in water (1 L) at room temperature. After the addition was complete the mixture was stirred for a further 15 min before being extracted with ether (500 mL). The residual red/brown solid in the reaction flask was taken up in MeOH (100 mL) and diluted with ether (300 mL) before being poured into the aqueous layer from above. The ether layer was separated and the combined organic layers were extracted with 1M NaOH (3×100 mL). The aqueous extracts were acidified with conc. HCl and then extracted with ether (2×150 mL). The ether layers were then washed with brine, dried (MgSO$_4$) and the solvent was removed in vacuo to give the phenol (5.465 g, 47%) as a brown crystalline solid; $\delta_H$ (400 MHz, CDCl$_3$) 2.44 (3H, s), 5.08 (1H, br), 6.77 (1H, d), 6.93 (1H, d), 7.18 (1H, d); MS m/z (ES$^-$) 173 (M-H$^+$).

Preparation 3

3-Fluoro-4-(methylsulfanyl)phenol

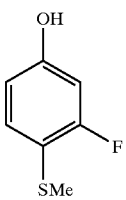

This compound was prepared using a similar method to that described above for Preparation 2 starting from commercially available 3,4-difluoronitrobenzene; $\delta_H$ (CDCl$_3$, 300 MHz) 2.40 (3H, s), 5.03 (1H, br), 6.60 (2H, m), 7.27 (1H, m obscured); MS m/z (ES $^-$) 157 (M-H$^+$).

Preparation 4

2,3-Dihydro-1,4-benzoxathiin-6-ol

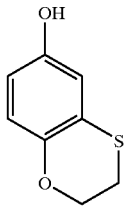

1,2-Dibromoethane (2.3 mL, 26.7 mmol) and $K_2CO_3$ (8.21 g, 59.4 mmol) were slurried in acetone (250 mL) and a solution of 2-sulfanyl-1,4-benzenediol (prepared according to *J. Org. Chem.* 1990, 55, 2736) (4.22 g, 29.7 mmol) in acetone (50 mL) was added over 4 h to the stirred mixture. Once the addition was complete stirring was continued for a further 10 h before the solvent was removed in vacuo. The residue was partitioned between water (50 mL) and EtOAc (50 mL), the aqueous layer was extracted with EtOAc (50 mL) and the combined organic layers were dried ($MgSO_4$) and evaporated. Purification of the residue by column chromatography [$SiO_2$; 9:1 (pentane/EtOAc)] gave the title compound (2.48 g, 55%) as a pale orange oil; $\delta_H$ ($CDCl_3$, 400 MHz) 3.08 (2H, m), 4.31 (2H, m), 4.44 (1H, s), 6.42 (1H, d), 6.49 (1H, s), 6.66 (1H, d); MS m/z ($ES^-$) 167 ($M-H^+$).

Preparation 5

2,3-Dihydro-1,4-benzoxathiin-7-ol

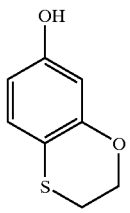

The title compound was prepared in a similar manner to the compound of Preparation 4 starting from 4-sulfanyl-1,3-benzenediol (prepared according to *J. Org. Chem.* 1979, 26, 4971–4973); $\delta_H$ ($CDCl_3$, 400 MHz) 3.05 (2H, t), 4.37 (2H, t), 6.32 (1H, s), 6.35 (1H, d), 6.84 (1H, d); MS m/z ($TS^+$) 169 ($MH^+$).

Preparation 6

1,3-Dihydro-2-benzofuran-5-ol

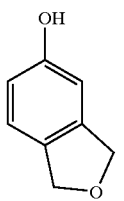

1,3-Dihydro-2-benzofuran-5-amine (prepared according to U.S. Pat. No. 4,000,286) (2.7 g, 20 mmol) was dissolved in a mixture of water (300 mL) and conc. $H_2SO_4$ (21 mL), cooled to 0° C. and $NaNO_2$ (1.43 g, 20.7 mmol) in water (10 mL) was added over 15 min. After stirring at 0° C. for 1 h the mixture was allowed to stir at 10° C. for 30 min and urea was added until a negative test with starch/KI paper was observed. The solution was then poured over 2 min into a mixture of water (180 mL) and conc. $H_2SO_4$ (12.6 mL) at 90° C. and stirred at this temperature for 1.5 h. The hot mixture was filtered then allowed to cool to room temperature. The aqueous mixture was extracted with EtOAc (2×100 mL) and the combined organic layers were dried ($MgSO_4$) and evaporated to give the title phenol (974 mg, 36%) as a cream solid; $\delta_H$ ($CDCl_3$, 400 MHz) 5.03 (4H, s), 6.71 (2H, m), 7.08 (1H, d).

Preparation 7

2,3-Dihydro-1-benzothiophen-6-ol

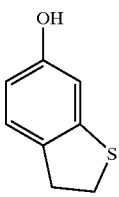

(i) Preparation of 2,3-dihydro-1-benzothiophen-6-ol 1,1-dioxide

A suspension of 2,3-dihydro-1-benzothiophen-6-amine 1,1-dioxide [prepared according to *J. Am. Chem. Soc.* 1955, 77, 5939] (15.73 g, 85.8 mmol) in water (500 mL) and conc. $H_2SO_4$ (35 mL) was warmed until solution was achieved. The mixture was cooled to 0° C. and a solution of $NaNO_2$ (6.22 g, 90 mmol) in water (15 mL) was then added over 5 min. The reaction was stirred at 0° C. for 1 h then urea was added, to remove excess nitrite, until a negative test with starch/KI paper was obtained. The mixture was allowed to warm to room temperature then added with stirring to a mixture of conc. $H_2SO_4$ (55 mL) and water (750 mL) at 90° C. The reaction was re-heated to 90° C. and stirred at this temperature for 30 min. The hot reaction mixture was filtered through Arbocel® then stirred at room temperature overnight. The aqueous mixture was extracted with ether (2.5 L) and then EtOAc (5×500 mL) and the combined organic layers were dried (MgSO4) and evaporated to give the desired phenol (12.7 g, 80%) which was used without further purification; $\delta_H$ ($CDCl_3$, 400 MHz) 3.30 (2H, m), 3.50 (2H, m), 7.05 (1H, m), 7.14 (1H, s), 7.23 (1H, m); MS m/z ($ES^-$) 183 ($M-H^+$).

(ii) Preparation of 2,3-dihydro-1-benzothiophen-6-ol

A solution of the sulfone from stage (i) (4.84 g, 26.3 mmol) in toluene (100 mL) and THF (70 mL) was added to a solution of DIBAL in toluene (1M, 100 mL, 100 mmol) and the mixture was then heated at reflux for 16 h. After cooling to room temperature EtOH (75 mL) was added cautiously followed by water (100 mL) with stirring. 6M HCl was added to the resulting thick suspension and the organic layer was separated. The aqueous layer was extracted with EtOAc (3×150 mL) and the combined organic layers were dried ($MgSO_4$) and evaporated to a beige solid. Purification by column chromatography [$SiO_2$; DCM/MeOH/880 $NH_3$ (97:3:0.25) increasing polarity to (95:5:0.5)] afforded the desired title phenol as a beige solid (1.85 g, 53%); $\delta_H$ ($CD_3OD$, 400 MHz) 3.13 (2H, t), 3.30 (2H, m), 6.41 (1H, d), 6.60 (1H, s), 6.98 (1H, d); MS m/z ($ES^-$) 151 ($M-H^+$).

Preparation 8

5-(Aminosulfonyl)-2-[3-methyl-4-(methylsulfanyl)phenoxy]-N-methylbenzamide

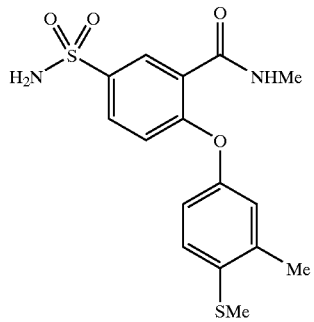

The fluoroamide of Preparation 1 (732 mg, 3.15 mmol) was treated with 4-(methylthio)-m-cresol (commercially available) (535 mg, 3.47 mmol) and potassium carbonate (457 mg, 3.31 mmol) in DMF (10 mL). The mixture was heated at 100° C. for 5 hours. The solvent was removed by evaporation under reduced pressure and the residue was treated with 2M HCl (10 mL). The resulting suspension was extracted several times with dichloromethane. The combined dichloromethane layers contained a suspension and were evaporated to a solid residue. The residue was triturated with ether (5 mL) and the remaining solid was washed with ether (3×10 mL) to give an off-white solid (765 mg, 66%). $\delta_H$ (300 MHz, $d_6$-DMSO) 2.28 (3H, s), 2.48 (3H, s), 2.70 (3H, d), 6.90 (1H, d) 7.02 (1H, d), 7.03 (1H, s), 7.30 (1H, d), 7.35 (2H, s), 7.79 (1H, d), 8.10 (1H, d), 8.30 (1H, m); MS m/z (TS$^+$) 367 (MH$^+$), 385 (MNH$_4^+$).

Preparations 9–18

Compounds of formula Va, i.e. compounds of general formula V where T is —C(=O)NHMe, $R^4$ is hydrogen and $R^5$ is —SO$_2$NH$_2$, shown in Table 17 were prepared according to Preparation 8 using the sulfonamide of Preparation 1 and the phenol indicated.

TABLE 17

(Va)

| Preparation | Precursor phenol | Z / Y structure | data |
|---|---|---|---|
| 9 | Synth. Commun. 1991, 21, 959–969 | 2,3-dihydrobenzothiophen-5-yl | $\delta_H$ (d$_6$-DMSO, 400 MHz) 2.80 (3H, d), 3.20 (2H, t), 3,40 (2H, t), 6.90 (1H, m), 7.05 (1H, s), 7.25 (1H, d), 7.35 (1H, s), 7.80 (1H, m), 8.10 (1H, s), 8.30 (1H, brs); MS m/z (TS$^+$) 365 (MH$^+$) |
| 10 | Prep 5 | 3,4-dihydro-2H-benzo[b][1,4]oxathiin-6-yl | $\delta_H$ (CD$_3$OD, 400 MHz) 2.92 (3H, s), 3.17 (2H, m), 4.41 (2H, m), 6.60–6.70 (2H, m), 6.97 (1H, m/z (TS$^+$) 381 (MH$^+$) |

TABLE 17-continued (Va)

| Preparation | Precursor phenol | Z–Y group | data |
|---|---|---|---|
| 11 | Prep 3 | 3-F, 4-SMe phenyl | δ$_H$ (CD$_3$OD, 400 MHz) 2.43 (3H, s), 2.97 (1H, s), 6.89 (2H, m), 7.00 (1H, d), 7.39 (1H, br), 7.88 (1H, brd), 8.23 (1H, s); MS m/z (ES$^+$) 371 (MH$^+$) |
| 12 | Prep 2 | 3-Cl, 4-SMe phenyl | δ$_H$ (CD$_3$OD, 400 MHz) 2.85 (3H, s), 2.99 (3H, s), 6.99 (1H, d), 7.09 (1H, d), 7.22 (1H, s), 7.37 (1H, d), 7.92 (1H, d), 8.28 (1H, s); MS m/z (ES$^+$) 387 (MH$^+$) |
| 13 | Prep 4 | 2,3-dihydro-1,4-benzoxathiine-6-yl | δ$_H$ (CD$_3$OD, 400 MHz) 2.87 (3H, brs), 3.13 (2H, brs), 4.37 (2H, brs), 6.73 (1H, brs), 6.82 (3H, m), 7.82 (1H, s), 8.28 (1H, brs); MS m/z (ES$^+$) 381 (MH$^+$) |
| 14 | Prep 6 | 1,3-dihydroisobenzofuran-5-yl | δ$_H$ (d$_6$-DMSO, 400 MHz) 2.79 (3H, s), 4.98 (4H, brs), 6.92 (1H, d), 7.04 (1H, d), 7.09 (1H, s), 7.37 (3H, m), 7.79 (1H, m), 8.10 (1H, s), 8.30 (1H, s); MS m/z (TS$^+$) 349 (MH$^+$) |
| 15 | Commercial | indan-5-yl | δ$_H$ (CD$_3$OD, 400 MHz) 2.08 (2H, m), 2.90 (7H, m), 6.84 (2H, m), 6.97 (1H, s), 7.23 (1H, d), 7.81 (1H, d), 8.31 (1H, s); MS m/z (TS$^+$) 347 (MH$^+$) |

TABLE 17-continued (Va)

[Structure: benzene ring with H₂N-SO₂- group, -C(O)NHMe group, and -O- linked to another benzene ring bearing Y and Z substituents]

[Generic substituent structure showing benzene ring with Y and Z positions]

| Preparation | Precursor phenol | Z [structure] | data |
|---|---|---|---|
| 16 | Tetrahedron 1982, 38, 2721 & Synthesis 1982, 475 | [benzene with SMe and Me] | Product used without purification |
| 17 | Prep 101 | [1,3-dihydrobenzo[c]thiophene] | $\delta_H$ (CD$_3$OD, 400 MHz) 2.88 (3H, s), 4.20 (4H, s), 6.89 (1H, d), 6.97 (1H, d), 7.01 (1H, s), 7.30 (1H, d), 7.84 (1H, d), 8.28 (1H, s); MS m/z (TS⁺) 382 (MNH$_4$⁺) |
| 18 | Prep 7 | [2,3-dihydrobenzothiophene] | $\delta_H$ (DMSO-d$_6$, 400 MHz) 2.78 (3H, d), 3.23 (2H, m), 3.40 (2H, m), 6.75 (1H, dd), 6.90 (1H, d), 7.02 (1H, s), 7.27 (1H, d), 7.34 (1H, d), 7.80 (1H, d), 8.10 (1H, s), 8.26 (1H, br, d); MS m/z (ES⁻) 363 (M − H⁺) |

Preparation 19

5-Bromo-2-(2,3-dihydro-1-benzothien-5-yloxy)benzaldehyde

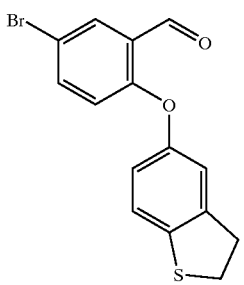

A mixture of 5-bromo-2-fluorobenzaldehyde (1.08 g, 5.32 mmol), 5-hydroxy-2,3-dihydrobenzothiophene (prepared as described in Synth. Commun. 1991, 21, 959–964) (808 mg, 5.31 mmol) and K$_2$CO$_3$ (1.47 g, 10.6 mmol) in DMF (5 mL) was heated at 90° C. for 16 h. After cooling to room temperature the mixture was partitioned between water (50 mL) and ether (50 mL), the aqueous layer being extracted with ether (50 mL). The combined organic extracts were washed with water (50 mL), dried (MgSO$_4$) and evaporated. The residue was purified by column chromatography [SiO$_2$; 9:1 (pentane/EtOAc)], then triturated with ether, to give the product (1.1 g, 62%) as a pale yellow solid; $\delta_H$ (CDCl$_3$, 400 MHz) 3.28 (2H, t), 3.41 (2H, t), 6.78 (1H, d), 6.84 (1H, d), 6.92 (1H, s), 7.20 (1H, d), 7.58 (1H, d), 8.00 (1H, s), 10.43 (1H, s).

Compounds of general formula II shown in Table 18 were prepared according to Preparation 19 by reacting the phenol indicated with the required 2-fluorobenzaldehyde.

In most cases the crude reaction product after aqueous work-up was used directly in subsequent steps without further purification.

TABLE 18

(II)

| Preparation | Precursor Phenol | R⁴ | R⁵ | Z | data |
|---|---|---|---|---|---|
| 20 | Prep 3 | H | Br | 4-SMe-3-F-phenyl | $\delta_H$ (CDCl$_3$, 300 MHz) 2.48 (3H, s), 6.81 (3H, m), 7.37 (1H, t), 7.64 (1H, d), 8.06 (1H, s), 10.39 (1H, s); MS m/z (TS⁺) 358, 360 (MNH$_4^+$) |
| 21 | Prep 5 | H | Br | 2,3-dihydro-1,4-benzoxathiin-6-yl | $\delta_H$ (CDCl$_3$, 400 MHz) 3.13 (2H, m), 4.42 (2H, m), 6.55 (1H, s), 6.59 (1H, d), 6.81 (1H, d), 7.04 (1H, d), 7.59 (1H, d), 8.01 (1H, s), 10.40 (1H, s) |
| 22 | Prep 2 | H | Br | 4-SMe-3-Cl-phenyl | $\delta_H$ (CDCl$_3$, 400 MHz) 2.43 (3H, s), 6.78 (1H, d), 6.94 (1H, d), 7.08 (1H, s), 7.19 (1H, d), 7.59 (1H, d), 8.00 (1H, s) |
| 23 | commercial | H | Br | 4-SMe-3-Me-phenyl | $\delta_H$ (CDCl$_3$, 300 MHz) 2.35 (3H, s), 2.49 (3H, s), 6.78 (1H, d), 6.90 (2H, s), 7.22 (1H, d), 7.59 (1H, d), 8.05 (1H, s), 10.45 (1H, s); MS m/z (TS⁺) 356, 354 (MNH$_4^+$) |
| 24 | commercial | H | MeO | 4-SMe-3-Me-phenyl | $\delta_H$ (CDCl$_3$, 300 MHz) 2.35 (3H, s), 2.45 (3H, s), 3.87 (3H, s), 6.82 (1H, d), 6.83 (1H, s), 6.92 (1H, d), 7.13 (1H, dd), 7.19 (1H, d), 7.40 (1H, d), 10.40 (1H, s); MS m/z (TS⁺) 389 (MH⁺) |

TABLE 18-continued

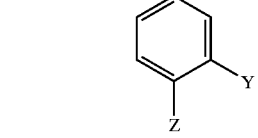
(II)

| Preparation | Precursor Phenol | R⁴ | R⁵ | Z | data |
|---|---|---|---|---|---|
| 25 | commercial | H | F | 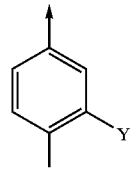 | $\delta_H$ (CDCl$_3$, 300 MHz) 7.02 (1H, dd), 7.21 (1H, s), 7.30 (1H, m), 7.40 (1H, m), 7.54 (1H, d), 7.66 (1H, dd), 8.01 (1H, d), 8.18 (1H, d), 8.88 (1H, d), 10.43 (1H, s); MS m/z (ES⁺) 268 (MH⁺) |
| 26 | commercial | H | H | 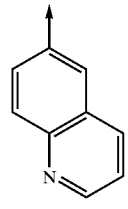 | $\delta_H$ (CDCl$_3$, 400 MHz) 6.97 (1H, d), 7.21–7.27 (2H, m), 7.38 (1H, dd), 7.49–7.58 (2H, m), 7.92–8.01 (2H, m), 8.11 (1H, d), 8.83 (1H, d), 10.50 (1H, s); MS m/z (ES⁺) 272 MNa⁺), (ES⁻) 248 (M − H⁺) |
| 27 | J. Chem. Soc. 1952, 4985–4993 | H | H | 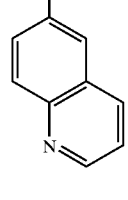 | $\delta_H$ (CDCl$_3$, 300 MHz) 7.08 (1H, d), 7.36 (2H, m), 7.65 (1H, m), 7.79 (1H, dd), 8.01 (1H, d), 8.13 (1H, d), 9.29 (1H, d), 10.45 (1H, s); MS m/z (TS⁺) 251 (MH⁺) |
| 28 | commercial | H | H | 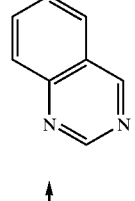 | $\delta_H$ (CDCl$_3$, 400 MHz) 7.09 (1H, d), 7.28 (1H, m), 7.35 (1H, m), 7.40 (1H, m), 7.50 (1H, br), 7.59 (1H, m), 7.86 (1H, dd), 7.99 (1H, dt), 8.15 (1H, d), 8.86 (1H, m), 10.46 (1H, s); MS m/z 250 (MH⁺) |
| 29 | Chem. Pharm. Bull., 1978, 26, 1443 | H | H | 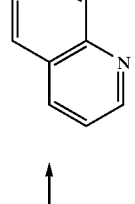 | $\delta_H$ (CDCl$_3$, 400 MHz) 6.91 (1H, d), 7.25 (2H, m), 7.55 (2H, m), 7.96 (1H, m), 8.12 (1H, d), 8.95 (1H, s), 10.5 (1H, s); MS m/z 256 (MH⁺) |

TABLE 18-continued

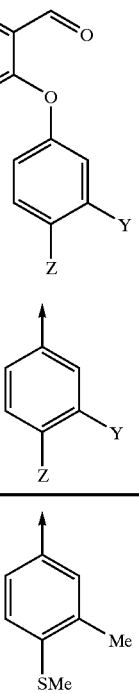

(II)

| Preparation | Precursor Phenol | R⁴ | R⁵ | Z | data |
|---|---|---|---|---|---|
| 30 | commercial | H | H | (4-SMe, 3-Me-phenyl) | δ_H (CDCl₃, 300 MHz) 2.35 (3H, s), 3.44 (3H, s), 6.87 (3H, m), 7.17 (2H, m), 7.50 (1H, t), 7.92 (1H, dd), 10.52 (1H, s); MS m/z (TS⁺) 259 (MH⁺) |
| 31 | Synth. Commun. 1991, 21, 959–964 | H | H | (2,3-dihydrobenzothiophen-5-yl) | δ_H (CDCl₃, 400 MHz) 3.26 (2H, t), 3.39 (2H, m), 6.85 (2H, t), 6.92 (1H, s), 7.18 (2H, m), 7.48 (1H, t), 7.92 (1H, d), 10.51 (1H, s); MS m/z (TS⁺) 257 (MH⁺) |
| 32 | commercial | Br | H | (4-SMe, 3-Me-phenyl) | δ_H (CDCl₃, 400 MHz) 2.36 (3H, s), 2.44 (3H, s), 6.88 (2H, m), 6.96 (1H, s), 7.18–7.25 (2H, obs), 7.77 (1H, d), 10.43 (1H, s) |
| 33 | Prep 7 | H | Br | (2,3-dihydrobenzothiophen-5-yl) | δ_H (CDCl₃, 400 MHz) 3.27 (2H, m), 3.42 (2H, m), 6.67 (1H, d), 6.80 (1H, d), 6.90 (1H, s), 71.6 (1H, d), 7.58 (1H, d), 8.01 (1H, s), 10.41 (1H, s); MS m/z (TS⁺) 354 (MNH₄⁺) |
| 34[a] | commercial | H | CN | (quinolin-6-yl) | δ_H (DMSO-d₆, 300 MHz) 6.26 (1H, d), 6.43 (1H, d), 7.49 (1H, d), 7.65–7.71 (2H, m), 7.88 (1H, d), 8.07 (1H, d), 8.17 (1H, s), 8.73 (1H, d), 8.89 (1H, s); MS m/z (ES−) 273 (M − H), (ES⁺) 275 (MH⁺) |

[a]—4-Fluoro-3-formylbenzonitrile was synthesised according to Synth. Commun. 1997, 27(7), 1199 and J. Org. Chem. 1961, 26, 2522.

The product from Preparation 30 was also prepared as follows.

Potassium carbonate (334.1 g, 2.42 mol) and 4-(methylthio)-m-cresol (273.4 g, 1.77 mol) were added successively to DMF (2 L). 2-Fluorobenzaldehyde (200 g, 1.61 mol) was then added to the slurry and the mixture heated in the range 100–110° C. After 48 h the reaction mixture was allowed to cool to room temperature and water (1.2 L) added. The solution was cooled to below 10° C. and the pH adjusted to 5 with concentrated HCl (0.37 L), keeping the temperature below 10° C. Water (0.15 L) and dichloromethane (0.9 L) were added and the mixture stirred. The layers were separated and the organic layer was washed with water (4×0.75 L). The solvent was distilled to azeotropically remove the water. Fresh dichloromethane was added as required. The dry dichloromethane solution was then concentrated in vacuo to give the crude product as an oil (422 g, 100%).

Compounds of formula IX shown in Table 19 were prepared according to Preparation 19, using either 2-chloro-5-nitrobenzaldehyde or 2-chloro-5-nitrobenzonitrile with the phenol indicated. For these reactions a shorter reaction time (ca. 2–3 h) was usually sufficient to achieve good conversion. In most cases the crude reaction product after aqueous work-up was used directly in subsequent steps without further purification.

TABLE 19

(IX)

| Preparation | Precursor | W | Z | data |
|---|---|---|---|---|
| 35 | Prep 3 | —C≡N | 4-SMe, 3-F phenyl | $\delta_H$ (CDCl$_3$, 400 MHz) 2.48 (3H, s), 6.85–6.95 (3H, m), 7.28 (1H, t), 8.30 (1H, d), 8.52 (1H, s) |
| 36 | Prep 5 | —CHO | 2,3-dihydro-1,4-benzoxathiine-6-yl | $\delta_H$ (CDCl$_3$, 400 MHz) 3.14 (2H, d), 4.43 (2H, d), 6.62 (2H, m), 6.92 (1H, d), 7.08 (1H, d), 8.27 (1H, d), 8.72 (1H, s), 10.51 (1H, s); MS m/z (TS$^+$) 318 (MH$^+$) |
| 37 | Prep 2 | —C≡N | 4-SMe, 3-Cl phenyl | $\delta_H$ (CDCl$_3$, 300 MHz) 2.55 (3H, s), 6.94 (1H, d), 7.09 (1H, dd), 7.22 (1H, d), 7.27 (1H, d), 8.36 (1H, dd), 8.60 (1H, d); MS m/z (TS$^+$) 338 (MNH$_4^+$) |
| 38 | Synth. Commun. 1991, 21, 959–964 | —CHO | 2,3-dihydrobenzothiophen-5-yl | $\delta_H$ (CDCl$_3$, 400 MHz) 3.29 (2H, m), 3.42 (2H, m), 6.88 (2H, m), 6.96 (1H, s), 7.23 (1H, d), 8.26 (1H, d), 8.75 (1H, s), 10.54 (1H, s) |

TABLE 19-continued (IX)

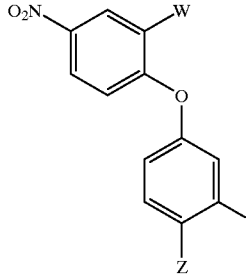

| Preparation | Precursor | W | Z | data |
|---|---|---|---|---|
| 39 | commercial | 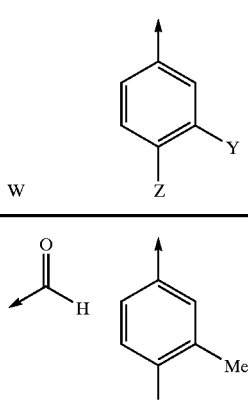 | 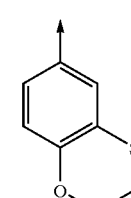 | δ$_H$ (CDCl$_3$, 400 MHz) 2.38 (3H, s), 2.50 (3H, s), 6.92 (1H, d), 6.99 (2H, m), 7.24 (1H, d), 8.28 (1H, dd), 8.78 (1H, d), 10.57 (1H, s) |
| 40 | commercial | 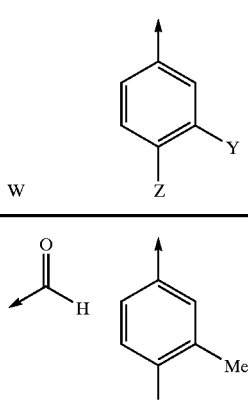 | 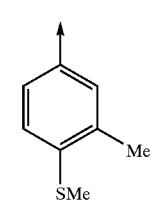 | δ$_H$ (CDCl$_3$, 400 MHz) 2.18 (2H, m), 2.95 (4H, t), 6.90 (2H, m), 7.29 (1H, d), 8.27 (1H, d), 8.79 (1H, s), 10.59 (1H, s); MS m/z (TS$^+$) 301 (MNH$_4^+$) |
| 41 | Prep 4 | —C≡N | 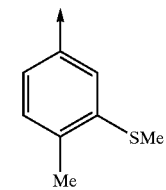 | δ$_H$ (CDCl$_3$, 400 MHz) 3.18 (2H, t), 4.44 (2H, t), 6.76 (1H, d), 6.86 (1H, s), 6.92 (2H, d), 8.32 (1H, d), 8.57 (1H, s); MS m/z (TS$^+$) 332 (MNH$_4^+$) |
| 42 | commercial | —C≡N | 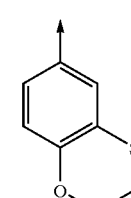 | δ$_H$ (CDCl$_3$, 400 MHz) 2.32 (3H, s), 2.47 (3H, s), 6.87 (1H, d), 6.94 (2H, m), 7.21 (1H, d), 8.26 (1H, dd), 8.51 (1H, d); MS m/z (TS$^+$) 318 (MNH$_4^+$) |
| 43 | Tetrahedron 1982, 38, 2721 & Synthesis 1982, 475 | —C≡N | 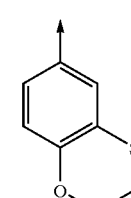 | δ$_H$ (CDCl$_3$, 400 MHz) 2.31 (3H, s), 2.41 (3H, s), 6.76 (1H, dd), 6.85 (2H, m), 7.19 (1H, d), 8.24 (1H, dd), 8.53 (1H, d); MS m/z (TS$^+$) 318 (MNH$_4^+$) |

Preparation 44 tert-Butyl 5-bromo-2-(2,3-dihydro-1-benzothien-5-yloxy)benzyl(methyl)carbamate

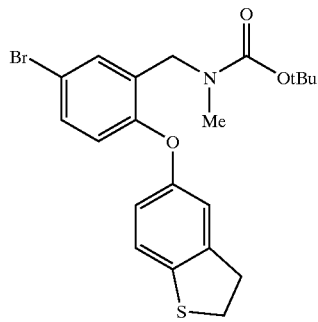

The hydrochloride salt of Example 36 (1.04 g, 2.7 mmol) was slurried in DCM (12 mL) and Et$_3$N (750 μL, 5.38 mmol) was added, followed by di-tert-butyl dicarbonate (766 mg, 3.51 mmol). After stirring at room temperature for 20 min the reaction was quenched by the addition of 0.2M HCl (20 mL). The well shaken mixture was separated and the aqueous layer was extracted with DCM (10 mL). The combined organic layers were dried (MgSO$_4$) and evaporated to give the product (assumed quantitative yield) as a colourless oil which was used without further purification; $\delta_H$ (CDCl$_3$, 400 MHz) 1.56 (9H, s), 2.82–2.98 (3H, brd), 3.23 (2H, t), 3.40 (2H, t), 4.44 (2H, brd), 6.71 (2H, d), 6.79 (1H, s), 7.12 (1H, d), 7.29 (1H, d), 7.39 (1H, s).

Compounds of formula X shown in Table 20 were prepared according to Preparation 44 starting from the precursors indicated.

TABLE 20

(X)

| Preparation | Precursor | Z / Y | data |
|---|---|---|---|
| 45 | Example 38 | [2,3-dihydro-1,4-benzodioxin-6-yl, S in ring] | $\delta_H$ (CDCl$_3$, 400 MHz) 1.41 (9H, brs), 2.81 (3H, m), 3.07 (2H, m), 4.36 (4H, m), 6.38 (1H, s), 6.43 (1H, d), 6.71 (1H, d), 6.92 (1H, d), 7.26 (1H, d), 7.34 (1H, s); MS m/z (ES$^+$) 468 (MH$^+$) |
| 46 | Example 39 | Y = Cl, Z = SMe | $\delta_H$ (CDCl$_3$, 400 MHz) 1.48 (9H, s), 2.41 (3H, s), 2, 82 (3H, brd), 4.39 (2H, brd), 6.73 (1H, d), 6.80 (1H, d), 6.93 (1H, s), 7.04 (1H, d), 7.32 (1H, d), 7.39 (1H, s); MS m/z (TS$^+$) 474 (MH$^+$) |

TABLE 20-continued

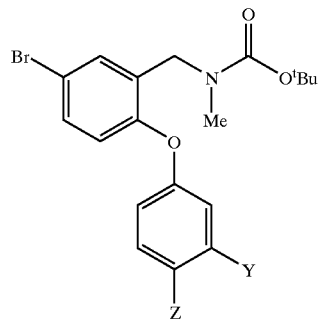

| Preparation | Precursor | Z | data |
|---|---|---|---|
| 47 | Example 37 |  (Y=F, Z=SMe) | $\delta_H$ (CDCl$_3$, 300 MHz) 1.46 (9H, brs), 2.46 (3H, s), 2.89 (3H, brs), 4.41 (2H, brs), 6.68 (2H, m), 6.82 (1H, d), 7.27 (1H, obs), 7.40 (1H, d), 7.43 (1H, s); MS m/z (TS$^+$) 458 (MH$^+$) |
| 48 | Example 44 | (Y=Me, Z=SMe) | $\delta_H$ (CDCl$_3$, 300 MHz) 1.45 (9H, br) 2.38 (3H, s), 2.44 (3H, s), 2.90 (3H, br), 4.47 (2H, br), 6.70–6.81 (3H, m) 7.20 (1H, d), 7.24–7.58 (2H, m) |

Preparation 49 tert-Butyl 5-cyano-2-[3-fluoro-4-(methylsulfanyl)phenoxy]benzyl-(methyl)carbamate

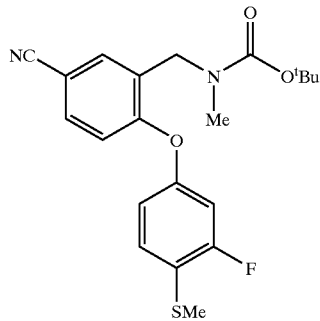

The title compound was prepared from the bromide of Preparation 47 by the method of Example 78; $\delta_H$ (CDCl$_3$, 300 MHz) 1.48 (9H, brs), 2.50 (3H, s), 2.93 (3H, brs), 4.55 (2H, brs), 6.79 (2H, m), 6.88 (1H, d), 7.35 (1H, t), 7.53 (1H, d), 7.59 (1H, s); MS m/z (TS$^+$) 403 (MH$^+$).

Preparation 50

Methyl 3-{[(tert-butoxycarbonyl)(methyl)amino]methyl}-4-(2,3-dihydro-1-benzothien-5-yloxy)benzoate

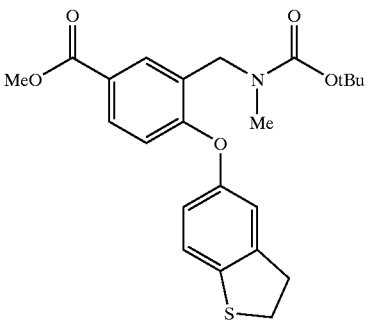

A mixture of the bromide of Preparation 44 (1.22 g, 2.7 mmol), Et$_3$N (1.13 mL, 8.11 mmol) and dichlorobis(triphenylphosphine)palladium (II) (190 mg, 0.27 mmol) in MeOH (14 mL) was heated at 80° C. under 100 psi pressure of CO for 18 h. Analysis by tlc indicated the reaction was not complete so a further portion of catalyst (190 mg, 0.27 mmol) was added and the mixture was heated at 100° C. under 100 psi pressure of CO for 24 h. The mixture was diluted with EtOAc (20 mL) and filtered through a pad of silica gel, eluting with excess EtOAc. The solvent was removed in vacuo and the residue was partitioned between EtOAc (50 mL) and a 2:1 mixture of water:880 NH$_3$ (50 mL). The aqueous layer was extracted with EtOAc (25 mL) and the combined organic layers were dried (MgSO$_4$) and evaporated. Purification by column chromatography [SiO$_2$; 4:1 (pentane/EtOAc)] gave the product (970 mg, 84%) as an oil; $\delta_H$ (CDCl$_3$, 400 MHz) 1.42 (9H, s), 2.90 (3H, brs), 3.22 (2H, t), 3.38 (2H, t), 3.84 (3H, s), 4.50 (2H, brd), 6/74 (2H, d), 6.82 (1H, s), 7.13 (1H, d), 7.82 (1H, d), 7.93 (1H, brd); MS m/z (ES$^+$) 430 (MH$^+$).

Compounds of formula XI shown in Table 21 were prepared according to Preparation 50 starting from the precursors indicated.

TABLE 21

(XI)

| Preparation | Precursor | Z | data |
|---|---|---|---|
| 51 | Prep 45 | (2,3-dihydro-1,4-benzoxathiin-6-yl, O on upper, S on lower) | $\delta_H$ (CDCl$_3$, 400 MHz) 1.42 (9H, s), 2.86 (2H, m), 3.07 (2H, m), 3.85 (3H, s), 4.37 (2H, m), 4.48 (2H, m), 6.48 (2H, m), 6.79 (1H, d), 6.97 (1H, d), 7.83 (1H, d), 7.95 (1H, s); MS m/z (ES$^+$) 446 (MH$^+$) |
| 52 | Prep 46 | (phenyl with Y=Cl, Z=SMe) | $\delta_H$ (CDCl$_3$, 400 MHz) 1.43 (9H, brs), 2.47 (3H, s), 2.88 (3H, brd), 3.90 (3H, s), 4.51 (2H, brd), 6.81 (1H, d), 6.91 (1H, d), 7.06 (1H, s), 7.20 (1H, d), 7.89 (1H, d), 7.98 (1H, brd); MS m/z (TS$^+$) 469 (MNH$_4^+$) |
| 53 | Prep 47 | (phenyl with Y=F, Z=SMe) | $\delta_H$ (CDCl$_3$, 300 MHz) 147 (9H, brs), 2.46 (3H, s), 2.91 (3H, brs), 3.94 (3H, s), 4.52 (2H, brs), 6.78 (2H, m), 6.91 (1H, d), 7.35 (1H, m), 7.92 (1H, d), 8.02 (1H, brs); MS m/z (TS$^+$) 453 (MNH$_4^+$) |
| 54 | Prep 48 | (phenyl with Y=Me, Z=SMe) | $\delta_H$ (CDCl$_3$, 300 MHz) 1.44 (9H, s), 2.37 (3H, s), 2.47 (3H, s), 2.94 (3H, br), 3.90 (3H, s), 4.73 (2H, br), 6.79–6.87 (3H, m), 7.20 (1H, d), 7.86 (1H, d), 8.00 (1H, br); MS m/z (ES$^+$) 454 (MNa$^+$) |

Preparation 55

3-{[(tert-Butoxycarbonyl)(methyl)amino]methyl}-4-(2,3-dihydro-1-benzothien-5-yloxy)benzoic acid

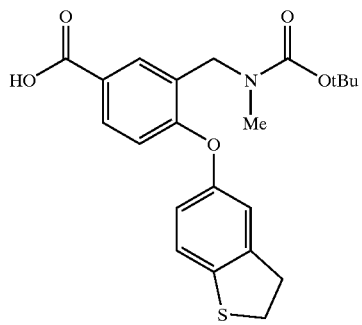

A solution of the ester of Preparation 50 (970 mg, 2.26 mmol) in THF (20 mL) and 1M LiOH (20 mL) was heated at reflux for 16 h. After cooling to room temperature the THF was removed in vacuo, the residue was neutralised with sat aq $NH_4Cl$ and the mixture was extracted with DCM (100 mL) and then ether (100 mL). The combined organic layers were dried ($MgSO_4$) and evaporated to give a white foam (960 mg) which was used without further purification; $\delta_H$ ($CDCl_3$, 400 MHz) 1.30 (9H, s), 2.78 (3H, brs), 3.20 (2H, brs), 3.38 (2H, t), 4.41 (2H, m), 6.62 (2H, m), 6.78 (1H, m), 7.10 (1H, m) 7.84 (1H, m), 7.99 (1H, m); MS m/z ($ES^-$) 414 (M−H).

Compounds of formula XII shown in Table 22 were prepared according to Preparation 55 from the precursors indicated.

TABLE 22

(XII)

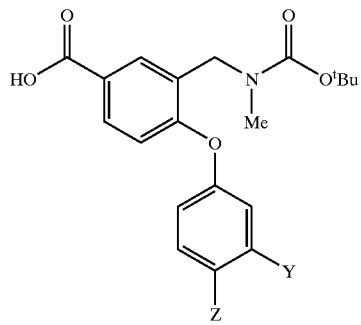

| Preparation | Precursor | | data |
|---|---|---|---|
| 56 | Prep 51 | 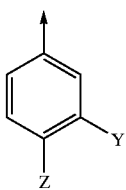 | $\delta_H$ ($CDCl_3$, 400 MHz) 1.26 (9H, s), 2.74 (3H, s), 3.02 (2H, m), 4.31 (4H, m), 6.38 (2H, m), 6.64 (1H, d), 6.87 (1H, d), 7.68 (1H, brs), 7.78 (1H, brs); MS m/z ($ES^-$) 430 (M − $H^+$) |

TABLE 22-continued

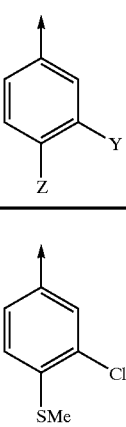

(XII)

| Preparation | Precursor | Z / Y | data |
|---|---|---|---|
| 57 | Prep 52 | Y=Cl, Z=SMe | δ$_H$ (CDCl$_3$, 400 MHz) 1.44 (9H, brs), 2.49 (3H, s), 2.92 (3H, brd), 4.57 (2H, brd), 6.82 (1H, d), 6.94 (1H, d), 7.08 (1H, s), 7.21 (1H, d), 7.97 (1H, d), 8.04 (1H, brd); MS m/z (ES⁻) 436 (M − H⁺) |
| 58 | Prep 53 | Y=F, Z=SMe | δ$_H$ (CDCl$_3$, 300 MHz) 1.46 (9H, brs), 2.49 (3H, s), 2.93 (3H, brs), 4.57 (2H, brs), 6.77 (2H, m), 6.92 (1H, d), 7.32 (1H, t), 7.99 (1H, d), 8.08 (1H, brs); MS m/z (ES⁻) 420 (M − H⁺) |

Preparation 59 tert-Butyl 5-(aminocarbonyl)-2-(2,3-dihydro-1-benzothien-5-yloxy)benzyl-(methyl)carbamate

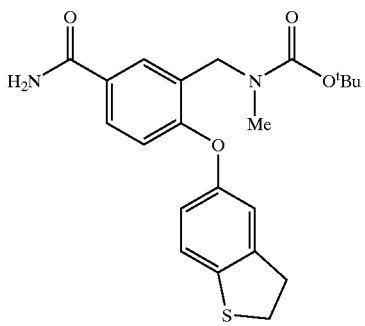

Et$_3$N (267 μL, 1.92 mmol), HOBt.H$_2$O (129 mg, 0.84 mmol) and WSCDI (191 mg, 1.0 mmol) were added to a solution of the acid of Preparation 55 (318 mg, 0.77 mmol) in DCM (10 mL) and the mixture was stirred for 1 h before the addition of a saturated solution of NH$_3$ in THF (2 mL). After stirring for a further 16 h the reaction was diluted with water (50 mL), 0.2M HCl (20 mL) and DCM (25 mL). The organic layer was separated and the aqueous layer was extracted with DCM (25 mL). The combined organic layers were dried (MgSO$_4$) and evaporated to give a white foam (assumed quantitative yield) which was used without further purification; δ$_H$ (CDCl$_3$, 400 MHz) 1.44 (9H, s), 2.91 (3H, br), 3.27 (2H, t), 3.40 (2H, t), 4.54 (2H, br), 6.75–6.88 (1H, m) 7.18 (1H, d), 7.68 (1H, d), 7.74 (1H, s).

Compounds of formula XII shown in Table 23 were prepared according to Preparation from the precursors indicated.

TABLE 23
(XIII)
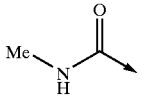
| Preparation | Precursor | R⁵ | Z | data |
|---|---|---|---|---|
| 60 | Prep 55 | 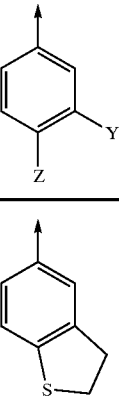 | 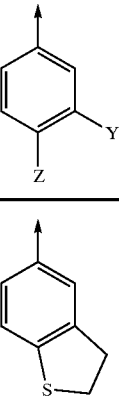 | δ_H (CDl₃, 400 MHz) 1.43 (9H, s), 2.83–3.00 (6H, m), 3.24 (2H, t), 3.39 (2H, t), 4.51 (2H, brs), 6.70–6.85 (3H, m), 7.15 (1H, d), 7.62 (1H, d), 7.68 (1H, s) |
| 61 | Prep 55 | 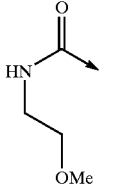 | 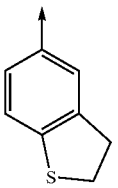 | δ_H (CDCl₃, 400 MHz) 1.46 (9H, s), 2.89 (3H, br), 3.24 (2H, t), 3.37–3.43 (5H, m), 3.56 (2H, t), 3.63 (2H, m), 4.54 (2H, br), 6.46 (1H, br), 6.75–6.86 (3H, m), 7.16 (1H, d), 7.62 (1H, d), 7.69 (1H, s) |
| 62 | Prep 58 | 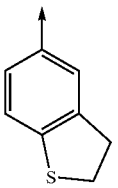 | 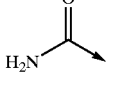 | δ_H (d₆-DMSO, 400 MHz) 1.29 (9H, br), 2.40 (3H, s), 2.75 (3H, s), 4.39 (2H, s), 6.78 (1H, d), 6.91 (2H, m), 7.23 (1H, br), 7.36 (1H, t), 7.78 (2H, m), 7.90 (1H, br); MS m/z (TS⁺) 438 (MNH₄⁺) |
| 63 | Prep 58 | 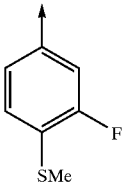 | 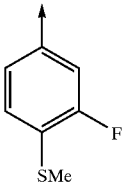 | δ_H (CDCl₃, 400 MHz) 1.41 (9H, s), 2.40 (3H, s), 2.92 (3H, brs), 2.98 (3H, d), 4.45 (2H, brs), 6.10 (1H, brs), 6.67 (2H, m), 6.88 (1H, d), 7.27 (1H, obs), 7.63 (2H, m); MS m/z (TS⁺) 452 (MNH₄⁺) |
| 64 | Prep 58 | 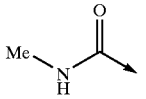 | 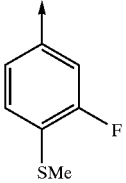 | δ_H (CDCl₃, 400 MHz) 1.40 (9H, s), 2.40 (3H, s), 2.81 (3H, brs), 3.35 (3H, s), 3.53 (2H, m), 3.61 (2H, m), 4.44 (2H, brs), 6.45 (1H, brs), 6.66 (2H, m), 6.87 (1H, d), 7.29 (1H, d), 7.64 (1H, d), 7.72 (1H, s); MS m/z (TS⁺) 479 (MH⁺) |

TABLE 23-continued
(XIII)
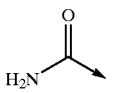
| Preparation | Precursor | R⁵ | Z Y | data |
|---|---|---|---|---|
| 65 | Prep 57 | 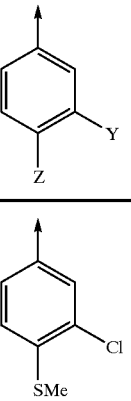 | 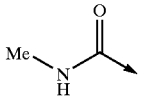 | $\delta_H$ (CDCl$_3$, 400 MHz) 1.43 (9H, brs), 2.47 (3H, s), 2.90 (3H, brd), 4.52 (2H, brs), 6.87 (1H, d), 6.91 (1H, d), 7.03 (1H, s), 7.10 (1H, d), 7.72 (1H, d), 7.78 (1H, s); MS m/z (ES⁺) 435 (M − H⁺) |
| 66 | Prep 57 | 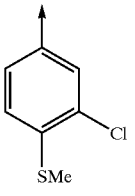 | 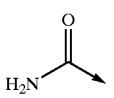 | $\delta_H$ (CDCl$_3$, 400 MHz) 1.42 (9H, brs), 2.47 (3H, s), 2.88 (3H, brd), 3.00 (3H, d), 4.48 (2H, brs), 6.16 (1H, brd), 6.85 (2H, m), 7.01 (1H, s), 7.19 (1H, d), 7.67 (2H, m); MS m/z (ES⁻) 449 (M − H⁺) |
| 67 | Prep 56 | 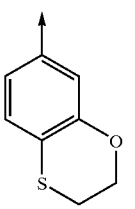 | 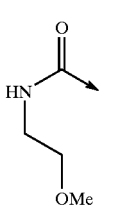 | $\delta_H$ (CDCl$_3$, 400 MHz) 1.42 (9H, s), 2.86 (3H, m), 3.08 (2H, m), 3.97 (2H, m), 4.48 (2H, brs), 5.86–6.27 (2H, brs), 6.45 (1H, s), 6.49 (1H, d), 6.82 (1H, d), 6.96 (1H, d), 7.64 (1H, d), 7.71 (1H, s); MS m/z (TS⁺) 331 (MH⁺ − Boc) |
| 68 | Prep 56 | 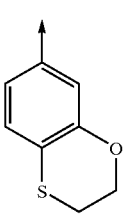 | 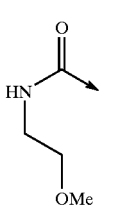 | $\delta_H$ (CDCl$_3$, 400 MHz) 1.26 (9H, s), 2.74 (3H, s), 3.02 (2H, m), 4.31 (4H, m), 6.38 (2H, m), 6.64 (1H, d), 6.87 (1H, d), 7.68 (1H, brs), 7.78 (1H, brs); MS m/z (ES⁻) 430 M − H⁺) |

Preparation 69 tert-Butyl 2-[3-chloro-4-(methylsulfanyl)phenoxy]-5-(hydroxymethyl)benzyl-(methyl)carbamate

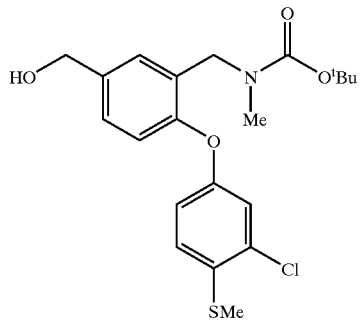

A solution of LiAlH$_4$ in THF (1M, 2 mL, 2 mmol) was added dropwise to a solution of the ester of Preparation 52 (452 mg, 1 mmol) in THF (10 mL) under N$_2$. Once the reaction was judged complete by tlc analysis, ether (10 mL) was added and the excess LiAlH$_4$ was quenched by the cautious addition of 2M NaOH. The organic layer was separated, washed with brine, dried (MgSO$_4$) and evaporated. Purification of the residue by column chromatography [SiO$_2$; 39:1 (DCM/MeOH)] gave the desired alcohol (200 mg, 47%) as a gummy white solid; $\delta_H$ (CDCl$_3$, 400 MHz) 1.41 (9H, brs), 1.80 (1H, brs), 2.43 (3H, s), 2.81 (3H, brd), 4.42 (2H, brd), 4.66 (2H, s), 6.82 (1H, d), 6.88 (1H, d), 6.96 (1H, s), 7.16 (1H, d), 7.27 (2H, obs); MS m/z (ES$^+$) 446 (MNa$^+$).

Compounds of formula XIV shown in Table 24 were prepared according to Preparation 69 starting from the precursors indicated.

TABLE 24

(XIV)

| Preparation | Precursor | | data | |
|---|---|---|---|---|
| 70 | Prep 53 | 3-F, 4-SMe phenyl | $\delta_H$ (CDCl$_3$, 400 MHz) 1.39 (9H, brs), 1.99 (1H, brs), 2.39 (3H, s), 2.78 (3H, brd), 4.39 (2H, brs), 4.62 (2H, d), 6.61 (2H, t), 6.88 (1H, d), 7.20–7.30 (3H, m + CHCl$_3$); MS m/z (TS$^+$) 408 (MH$^+$) | |
| 71 | Prep 54 | 3-Me, 4-SMe phenyl | $\delta_H$ (CDCl$_3$, 300 MHz) 1.45 (9H, s), 2.34 (3H, s), 2.46 (3H, s), 2.90 (3H, br), 4.49 (2H, s), 4.67 (2H, s), 6.72–6.81 (2H, m), 6.85 (1H, d), 7.18 (1H, d), 7.21–7.30 (2H, obs); MS m/z (TS$^+$) 404 (MH$^+$) | |

Preparation 72 tert-Butyl 3-{[(tert-butoxycarbonyl)(methyl)amino]methyl}-4-[3-methyl-4-(methylsulfanyl)phenoxy]benzyl(methylsulfonyl)carbamate

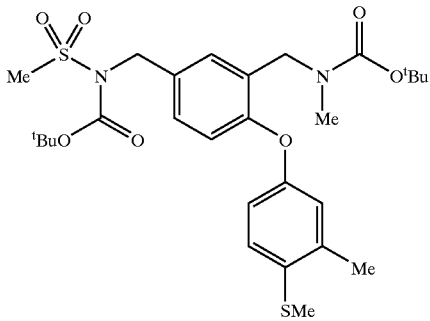

A solution of diethyl azodicarboxylate (505 μL, 3.21 mmol) in THF (5 mL) was added dropwise to a solution of tert-butyl methylsulfonylcarbamate (synthesised according to *Tetrahedron Lett.* 1994, 35, 379–380) (655 mg, 3.36 mmol), the alcohol of Preparation 71 (1.226 g, 3.04 mmol) and triphenylphosphine (880 mg, 3.36 mmol) in THF (15 mL) at 0° C. The reaction was stirred at 0° C. for 2 h then diluted with EtOAc (80 mL) and washed with 10% aq. $K_2CO_3$ (100 mL). The organic layer was washed with brine, dried ($MgSO_4$) and evaporated. The residue was purified by column chromatography [$SiO_2$; 1:4 EtOAc:pentane] to give the title compound (1.406 g, 80%) as a colourless oil; $\delta_H$ ($CDCl_3$, 300 MHz) 1.45 (9H, s), 1.52 (9H, s), 2.38 (3H, s), 2.44 (3H, s), 2.83 (3H, s) 3.22 (1H, s), 4.49 (2H, s), 4.85 (2H, s), 6.74–6.83 (3H, m), 7.18–7.29 (3H, obs); MS m/z ($TS^+$) 481 ($MH^+$–BOC).

Preparation 73 tert-Butyl 3-{[(tert-butoxycarbonyl)(methyl)amino]methyl}-4-[3-fluoro-4-(methylsulfanyl)phenoxy]benzyl(methylsulfonyl)carbamate

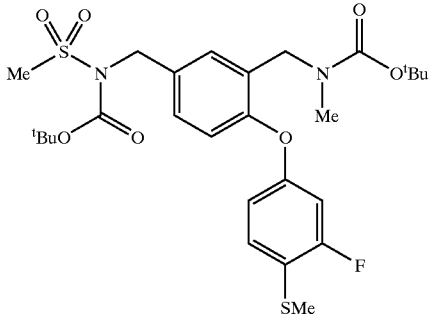

The title compound was prepared from the alcohol of Preparation 70 by the method of Preparation 72; $\delta_H$ ($CDCl_3$, 300 MHz) 1.44 (9H, s), 1.52 (9H, s), 2.44 (3H, s), 2.82 (3H, s), 3.23 (3H, s), 4.45 (2H, s), 4.87 (2H, s), 6.61–6.70 (2H, m), 6.90 (1H, d), 7.25–7.33 (3H, m); MS m/z ($ES^+$) 607 ($MNa^+$).

Preparation 74 tert-Butyl 4-[(dimethylamino)methyl]-3-[3-methyl-4-(methylsulfanyl)phenoxy]benzyl(methylsulfonyl)carbamate

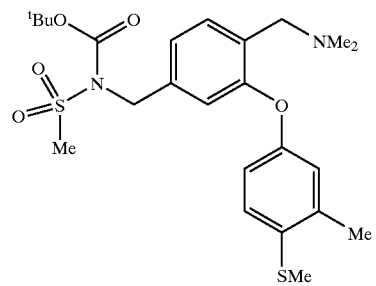

The title compound was prepared from the alcohol of Example 59 by the method of Preparation 72. The crude product was not purified by column chromatography but taken on directly to the next step; $\delta_H$ ($CDCl_3$, 400 MHz) 1.39 (9H, s), 2.22 (6H, s), 2.28 (3H, s), 2.38 (3H, s), 3.07 (3H, s), 3.42 (2H, s), 4.76 (2H, s), 6.72 (2H, m), 6.79 1H, s), 7.07 (1H, d), 7.12 (1H, d), 7.40 (1H, obs).

Preparation 75 tert-Butyl methyl[2-[3-methyl-4-(methylsulfanyl)phenoxy]-5-({[(trifluoromethyl)sulfonyl]amino}methyl)benzyl]carbamate

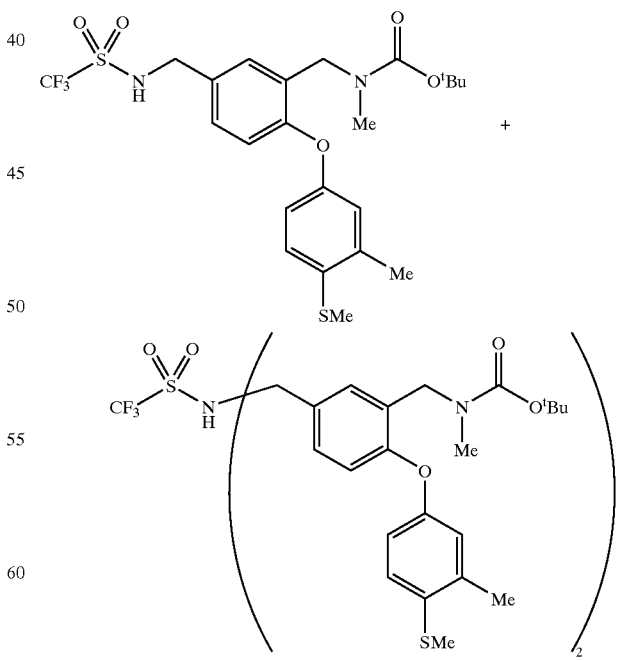

The title compound was prepared from the alcohol of Preparation 71 by the method of Preparation 72 using trifluoromethanesulfonamide instead of tert-butyl methylsulfonylcarbamate. The desired product was contaminated with tert-butyl 5-({{3-{[(tert-butoxycarbonyl)(methyl)amino](methyl)}-4-[3-methyl-4-(methylsulfanyl)phenoxy]benzyl}[(trifluoromethyl)sulfonyl]amino}methyl)-2-[3-methyl-4-(methylsulfanyl)phenoxy]benzyl(methyl)carbamate and was taken on as a mixture; MS m/z (ES⁻) 533 (M−H⁺).

Compounds of formula XV shown in Table 25 were prepared according to Preparation 44 using the precursors indicated.

TABLE 25

(XV)

| Preparation | Precursor | Z | data |
|---|---|---|---|
| 76 | Example 41 | 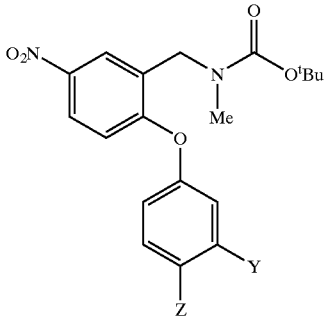 | δ_H (CDCl₃, 400 MHz) (major rotamer) 1.51 (9H, s), 2.92 (3H, s), 3.10 (2H, m), 4.40 (2H, m), 4.52 (2H, br), 6.53 (2H, m), 6.81 (1H, m), 7.03 (1H, d), 7.97–8.21 (2H, m); MS m/z (TS⁺) 433 (MH⁺) |
| 77 | Example 40 | 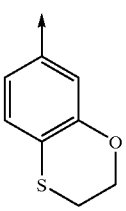 | δ_H (CDCl₃, 300 MHz) 1.50 (9H, br), 2.99 (3H, s), 3.29 (2H, m), 3.43 (2H, m), 4.60 (2H, br), 6.81 (2H, m), 6.91 (1H, s), 7.22 (1H, d), 8.04 (1H, d), 8.21 (1H, br) |
| 78 | Example 42 | 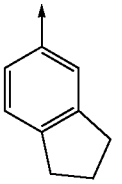 | δ_H (CDCl₃, 400 MHz) 1.56 (9H, s), 2.15 (2H, m), 2.85–3.00 (7H, m), 4.60 (2H, brd), 6.78 (2H, m), 6.87 (1H, s), 7.12 (1H, d), 8.03 (1H, d), 8.10 (1H, s); MS m/z (TS⁺) 399 (MH⁺) |

Preparation 79 tert-Butyl methyl{2-[3-methylsulfanyl)phenoxy]-5-nitrobenzyl}carbamate

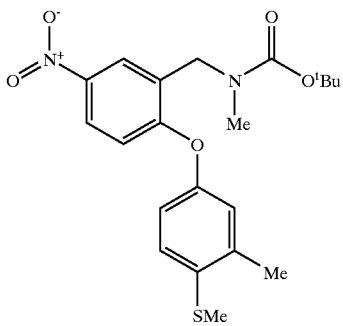

N-Methyl-N-{2-[3-methyl-4-(methylsulfanyl)phenoxy]-5-nitrobenzyl}amine and {2-[3-methyl-4-(methylsulfanyl)phenoxy]-5-nitrophenyl}methanol.

To a suspension of the aldehyde of Preparation 39 (21.0 g, 69.2 mmol) in EtOH (100 mL) was added 8M methylamine in EtOH (86.5 ml, 692 mmol). A solution was given and after stirring for a short time a precipitate was observed. This was re-dissolved by the addition of THF (100 mL), the solution was cooled to 0° C. and NaBH$_4$ (7.85 g, 208 mmol) was then added. The reaction was allowed to warm slowly to room temperature and stirred overnight before the solvent was removed in vacuo. The residue was taken up in water (150 mL) and ether (150 mL), and 2M HCl was added cautiously until pH 1. The layers were separated and the aqueous layer was washed with ether (2×100 mL). The combined organic extracts were dried and evaporated to give {2-[3-methyl-4-(methylsulfanyl)phenoxy]-5-nitrophenyl}methanol (18.9 g, 89%) as a yellow solid; δ$_H$ (CDCl$_3$, 400 MHz) 2.35 (3H, s), 2.48 (3H, s), 4.90 (2H, s), 6.79 (1H, d), 6.89 (1H, s), 6.91 (1H, d), 7.22 (1H, d), 8.07 (1H, dd), 8.41 (1H, d).

The aqueous layer from above was neutralised by pouring onto excess solid K$_2$CO$_3$. The basic solution was extracted with ether (2×100 mL) and these ether extracts were dried (MgSO$_4$) and evaporated to give N-methyl-N-{2-[3-methyl-4-(methylsulfanyl)phenoxy]-5-nitrobenzyl}amine (1.65 g, 7.5%) as an orange oil; MS m/z (ES$^+$) 319 (MH$^+$).

N-Methyl-N-{2-[3-methyl-4-(methylsulfanyl)phenoxy]-5-nitrobenzyl}amine from {2-[3-methyl-4-(methylsulfanyl)phenoxy]-5-nitrophenyl}methanol Methanesulfonyl chloride (4.81 mL, 61.9 mmol) was added slowly to a solution of {2-[3-methyl-4-(methylsulfanyl)phenoxy]-5-nitrophenyl}methanol (18.9 g, 61.9 mmol) and Et$_3$N (9.5 mL, 68.2 mmol) in DCM (60 mL). The mixture was stirred at room temperature for 3 h then poured into water and extracted with DCM (3 times). The combined organic extracts were dried (MgSO$_4$) and evaporated to give a dark, viscous oil. This oil was taken up in DCM (50 mL) and 8M methylamine in EtOH (200 mL, 1.6 mol) was added followed by Et$_3$N (10 mL, 71.7 mmol). After stirring for 18 h the mixture was concentrated in vacuo to give crude amine which was used without further purification.

tert-Butyl methyl{2-[3-methyl-4-(methylsulfanyl)phenoxy]-5-nitrobenzyl}carbamate The crude amine from above was dissolved in DCM (100 mL) at 0° C. and Et$_3$N (11.4 mL, 81.8 mmol) was added, followed by di-tert-butyl dicarbonate (15.0 g, 68.7 mmol). The reaction was allowed to warm to room temperature and stirred for 16 h before being concentrated in vacuo. The residue was partitioned between EtOAc and water and the aqueous layer was extracted with EtOAc (2 times). The combined organic layers were dried (MgSO$_4$) and evaporated. The residue was purified by column chromatography (SiO$_2$; 1$^{st}$ column–3% MeOH in DCM; 2$^{nd}$ column EtOAc-:pentane 1:3) to give the title compound (14.2 g, 54%) as a yellow oil; δ$_H$ (CDCl$_3$, 400 MHz) 1.44 (9H, s), 2.32 (3H, s), 2.44 (3H, s), 2.95 (3H, s), 4.56 (2H, br), 6.75 (1H, d), 6.84 (2H, m), 7.17 (1H, d), 8.00 (1H, d), 8.18 (1H, br); MS m/z (TS$^+$) 419 (MH$^+$).

Compounds of formula XVI shown in Table 26 were prepared according to Example 103 from the precursors indicated TABLE 26
(XVI)
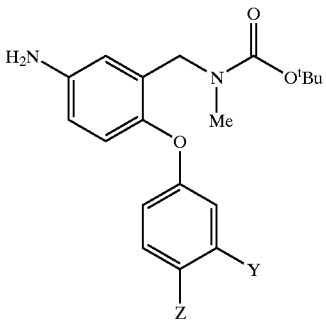
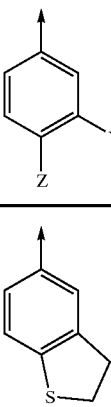
| Preparation | Precursor | | data |
|---|---|---|---|
| 80 | Prep 77 | 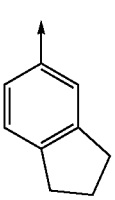 | δ$_H$ (CDCl$_3$, 300 MHz) 1.50 (9H, br), 2.80 (3H, br), 3.20 (2H, m), 2.37 (2H, m), 3.60 (2H, br), 4.40 (2H, s), 6.50–6.80 (5H, m), 7.05 (1H, d); MS m/z (ES$^+$) 387 (MH$^+$) |
| 81 | Prep 78 | 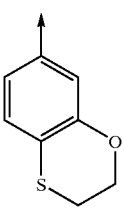 | δ$_H$ (CDCl$_3$, 400 MHz) 1.42 (9H, s), 2.05 (2H, m), 2.80 (7H, m), 4.37 (2H, s), 6.50–6.65 (3H, m), 6.69 (1H, s), 6.78 (1H, d), 7.08 (1H, d); MS m/z (TS$^+$) 369 (MH$^+$) |
| 82 | Prep 76 | | δ$_H$ (CDCl$_3$, 400 MHz) 1.43 (9H, s), 2.88 (3H, br), 3.07 (2H, m), 3.59 (2H, br), 4.30 (2H, s), 4.36 (2H, m), 6.32 (1H, s), 6.40 (1H, d), 6.49–6.65 (2H, m), 6.75 (1H, d), 6.88 (1H, d); MS m/z (TS$^+$) 403 (MH$^+$) |
| 83 | Prep 79 | 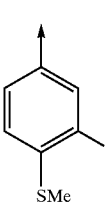 | δ$_H$ (CDCl$_3$, 300 MHz) 1.47 (9H, s), 2.33 (3H, s), 2.40 (3H, s), 2.82 (3H, br), 3.60 (2H, s), 4.35 (2H, s), 6.50–6.77 (4H, m), 6.80 (1H, d), 7.16 (1H, d); MS m/z(TS$^+$) 389 (MH$^+$) |

Preparation 84 tert-Butyl methyl{2-[3-methyl-4-(methylsulfanyl)phenoxy]-5-[(methylsulfonyl)amino]benzyl}carbamate

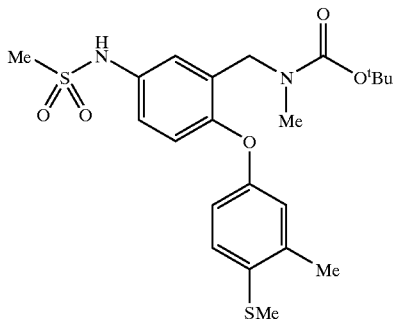

Methanesulfonyl chloride (4.16 mL, 53.7 mmol) was added dropwise to a solution of the aniline of Preparation 83 (9.5 g, 24.5 mmol) and Et$_3$N (7.5 mL, 53.8 mmol) in DCM (50 mL) at 0° C. After stirring at 0° C. for 30 min the reaction was allowed to warm to room temperature before the solvent was removed in vacuo. 2M NaOH (50 mL) was added to the residue and the mixture was stirred for 30 min. The mixture was extracted with EtOAc and the organic layer was washed with brine, dried (MgSO$_4$) and evaporated to give an oil. Purification by column chromatography [SiO$_2$; 97.5:2.5:0.25 (DCM/MeOH/OH/880 NH$_3$)] gave the product (9.0 g, 79%) as a brown foam; $\delta_H$ (CDCl$_3$, 300 MHz) 1.43 (9H, brs), 2.35 (3H, s), 2.42 (3H, s), 2.88 (3H, brs), 3.01 (3H, s), 4.46 (2H, brs), 6.76 (2H, d+s), 6.83 (1H, d), 7.16 (1H, s), 7.20 (2H, brs); MS m/z (ES$^+$) 467 (MH$^+$).

Compounds of formula XVII shown in Table 27 were prepared according to Preparation 84 from the precursors indicated.

TABLE 27

(XVII)

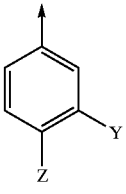

| Preparation | Precursor | Z | data |
|---|---|---|---|
| 85 | Prep 81 | 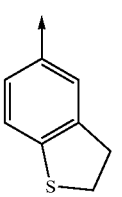 | $\delta_H$ (CDCl$_3$, 400 MHz) (rotamers) 1.44 and 1.48 (9H, 2xs), 2.10 (2H, quintet), 2.88 (7H, m), 3.00 (3H, s), 4.49 (2H, br), 6.23 (1H, br), 6.72 (1H, d), 6.81 (1H, s), 6.83 (1H, d), 7.13 (3H, m); MS m/z (TS$^+$) 347 (MH$^+$ − Boc) |
| 86 | Prep 80 | | Product used without purification. |

TABLE 27-continued (XVII)

[Structure XVII shown at top of table]

| Preparation | Precursor | ![Z/Y substituent] | data |
|---|---|---|---|
| 87 | Prep 82 | 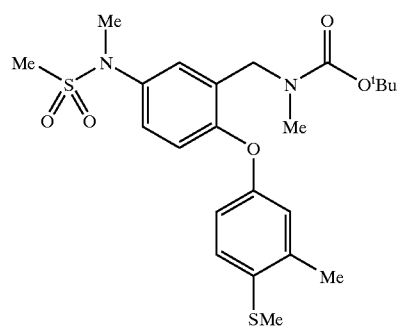 | δ$_H$ (CDCl$_3$, 400 MHz) (rotamers) 1.40 and 1.44 (9H, 2xs), 2.80 and 2.85 (3H, 2xs), 2.95 (3H, s), 3.07 (2H, m), 4.38 (2H, m), 6.36 (1H, s), 6.44 (1H, d), 6.84 (1H, d), 6.92 (1H, d), 7.12 (2H, m); MS m/z (TS$^+$) 498 (MNH$_4^+$) |

Preparation 88 tert-Butyl methyl{2-[3-methyl-4-(methylsulfanyl)phenoxy]-5-[methyl(methyl-sulfonyl)amino]benzyl}carbamate MeI (1.07 mL, 17.2 mmol) was added dropwise to a mixture of the sulfonamide of Preparation 84 (2.0 g, 4.3 mmol) and K$_2$CO$_3$ (592 mg, 4.3 mmol) in CH$_3$CN (10 mL) under N$_2$. The mixture was stirred for 16 h and then partitioned between EtOAc (50 mL) and 2M NaOH (50 mL). The organic layer was washed with brine, dried (MgSO$_4$) and evaporated. The residue was purified by column chromatography [SiO$_2$; 590:10:1 (DCM/MeOH/880 NH$_3$)] to give the product (1.23 g, 60%) as a yellow oil; δ$_H$ (CDCl$_3$, 300 MHz) 1.45 (9H, s), 2.34 (3H, s), 2.42 (3H, s), 2.86 (3H, s), 2.90 (3H, s), 3.28 (3H, s), 4.49 (2H, s), 6.80 (3H, br), 7.18 (3H, m); MS m/z (TS$^+$) 498 (MNH$_4^+$).

Preparation 89 tert-Butyl 5-[(2-hydroxyethyl)(methylsulfonyl)amino]-2-[3-methyl-4-(methylsulfanyl)phenoxy]benzyl(methyl)carbamate

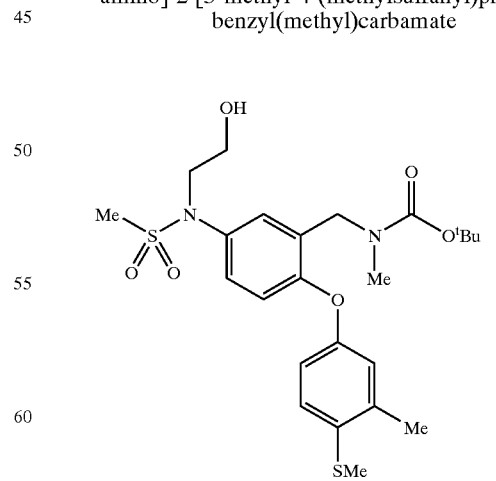

2-Bromoethanol (1.34 mL, 18.9 mmol) was added to a mixture of the sulfonamide of Preparation 84 (2.0 g, 4.3 mmol) and K$_2$CO$_3$ (2.605 g, 18.8 mmol) in CH$_3$CN (10 mL) under N$_2$. The mixture was heated at reflux for 16 h, cooled and then partitioned between EtOAc (50 mL) and 2M NaOH (50 mL). The organic layer was washed with brine, dried (MgSO$_4$) and evaporated. The residue was purified by column chromatography [SiO$_2$; 390:10:1 (DCM/MeOH/880 NH$_3$)] to give the product (524 mg, 24%) as a pink foam; $\delta_H$ (CDCl$_3$, 300 MHz) 1.42 (9H, s), 2.37 (3H, s), 2.43 (3H, s), 2.91 (3H, s), 2.98 (3H, s), 3.68 (2H, brs), 3.79 (2H, d), 4.49 (2H, s), 6.81 (3H, m); MS m/z (TS$^+$) 528 (MNH$_4^+$).

Preparation 90

5-Amino-2-(2,3-dihydro-1,4-benzoxathin-6-yloxy)benzonitrile

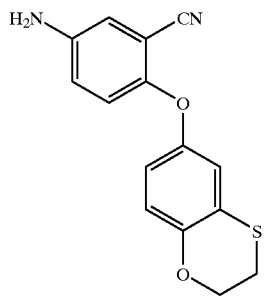

Fe powder (930 mg, 16.7 mmol) was added to the nitro compound of Preparation 41 (740 mg, 2.38 mmol) in AcOH (5 mL) and water (1 mL) and the mixture was stirred at room temperature for 16 h. The solvent was removed in vacuo, the residue was taken up in EtOAc (50 mL) and 10% aq K$_2$CO$_3$ (50 mL) and filtered through Arbocel®. The organic layer was separated and the aqueous layer was extracted with EtOAc (50 mL). The combined organic extracts were dried (MgSO$_4$) and evaporated to a brown foam (670 mg, 99%) which was used without further purification; $\delta_H$ (CDCl$_3$, 400 MHz) 3.18 (2H, m), 4.36 (2H, m), 6.60–6.70 (2H, m), 6.70–6.80 (3H, m), 6.85 (1H, s); MS m/z (TS$^+$) 302 (MNH$_4^+$).

Compounds of formula Vb, i.e. compounds of formula V where T is cyano, R$^4$ is hydrogen and R$^5$ is amino, shown in Table 28 were prepared according to Preparation 90 from the precursors indicated.

TABLE 28

(Vb)

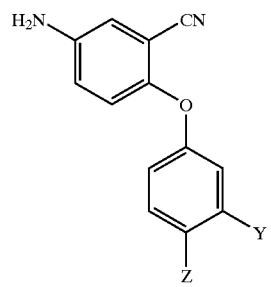

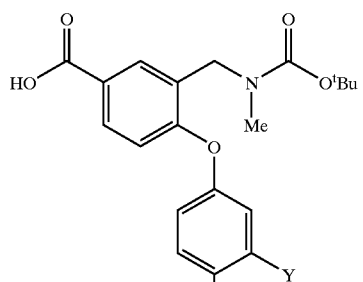

| Preparation | Precursor | data |
|---|---|---|
| 91 | Prep 35 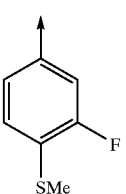 | $\delta_H$ (CDCl$_3$, 400 MHz) 2.40 (3H, s), 6.62–6.72 (2H, m), 6.80–6.90 (3H, m), 7.28 (1H, d) |

TABLE 28-continued

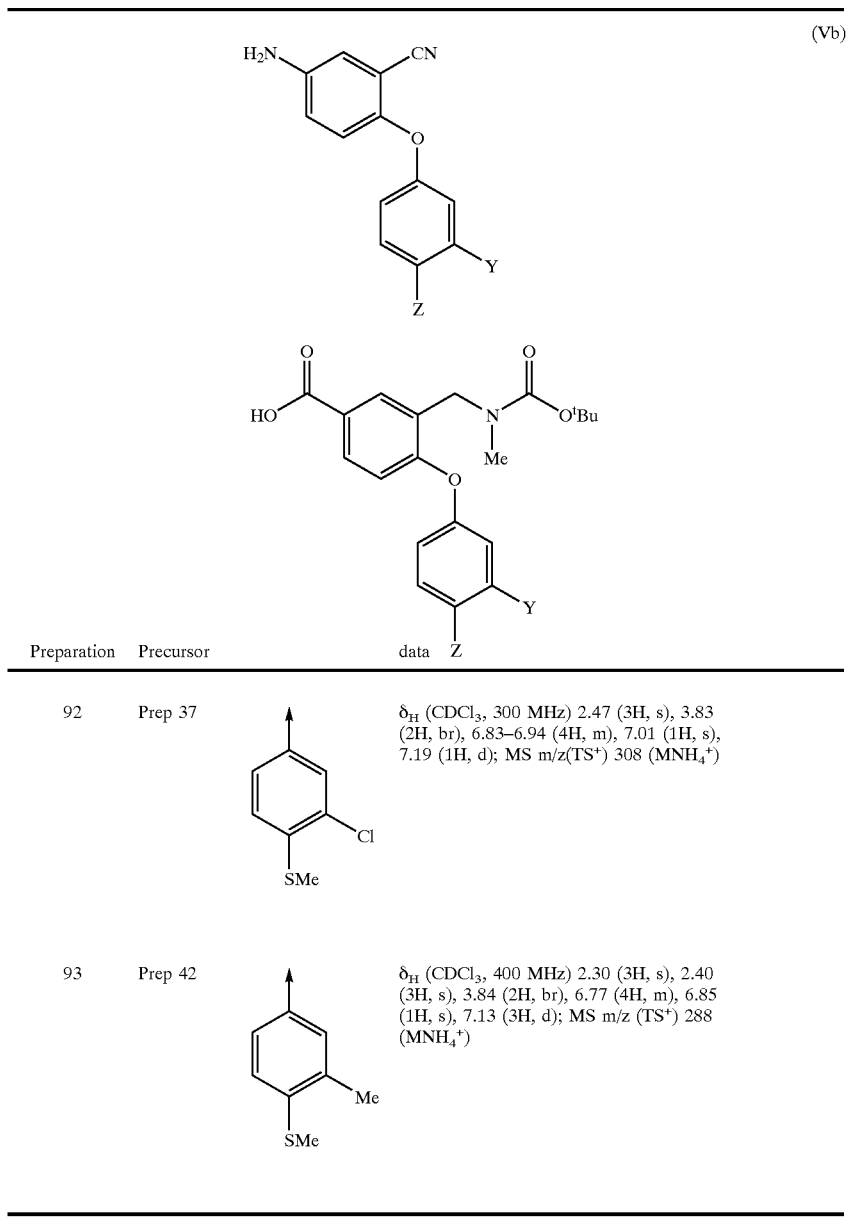

| Preparation | Precursor | | data |
|---|---|---|---|
| 92 | Prep 37 | 3-Cl-4-SMe-phenyl | δ_H (CDCl₃, 300 MHz) 2.47 (3H, s), 3.83 (2H, br), 6.83–6.94 (4H, m), 7.01 (1H, s), 7.19 (1H, d); MS m/z(TS⁺) 308 (MNH₄⁺) |
| 93 | Prep 42 | 3-Me-4-SMe-phenyl | δ_H (CDCl₃, 400 MHz) 2.30 (3H, s), 2.40 (3H, s), 3.84 (2H, br), 6.77 (4H, m), 6.85 (1H, s), 7.13 (3H, d); MS m/z (TS⁺) 288 (MNH₄⁺) |

Preparation 94

5-Amino-2-[4-methyl-3-(methylsulfanyl)phenoxy]benzonitrile

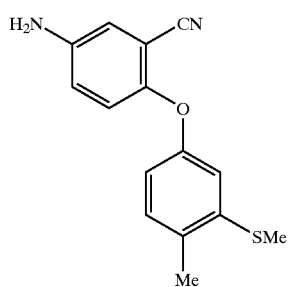

The title compound was prepared from the nitro compound of Preparation 43 by the method of Example 103; δ_H (CDCl₃, 400 MHz) 2.27 (3H, s), 2.41 (3H, s), 3.66 (2H, br), 6.62 (1H, d), 6.79 (2H, s), 6.82 (1H, s), 6.89 (1H, s), 7.08 (1H, d); MS m/z (ES⁺) 293 (MNa⁺), (ES⁻) 269 (M–H⁺).

Compounds of formula Vc, i.e. compounds of formula V where T is cyano, $R^4$ is hydrogen and $R^5$ is —NHSO₂Me, shown in Table 29 were prepared according to Preparation 84 from the precursors indicated.

TABLE 29

(Vc)

| Preparation | Precursor | Z (structure with Y) | data |
|---|---|---|---|
| 95 | Prep 90 | benzo[1,4]oxathiane (S, O fused) | δ_H (CDCl₃, 400 MHz) 2.98 (3H, s), 3.10 (2H, m), 4.39 (2H, m), 6.67 (1H, dd), 6.76 (1H, s), 6.81 (1H, d), 7.33 (1H, dd), 7.49 (1H, s); MS m/z (TS⁺) 380 (MNH₄⁺) |
| 96 | Prep 92 | Y=Cl, Z=SMe | δ_H (CDCl₃, 300 MHz) 2.51 (3H, s), 3.06 (3H, s), 6.52 (1H, br), 6.92 (1H, d), 7.02 (1H, dd), 7.14 (1H, d), 7.24 (1H, d), 7.41 (1H, dd), 7.57 (1H, d); MS m/z (ES⁺) 391 (MNa⁺) |
| 97 | Prep 91 | Y=F, Z=SMe | δ_H (CDCl₃, 400 MHz) 2.43 (3H, s), 3.02 (3h, S), 6.41 (1H, brs), 6.72–6.85 (2H, m), 6.92 (1H, d), 7.28 (1H, t), 7.38 (1H, d), 7.51 (1H, s); MS m/z (ES⁺) 351 (MH⁺) |
| 98 | Prep 93 | Y=Me, Z=SMe | δ_H (CDCl₃, 400 MHz) 2.19 (3H, s), 2.42 (3H, s), 2.99 (3H, s), 6.81 (1H, d), 6.86 (2H, m), 7.15 (1H, d), 7.33 (1H, d), 7.51 (1H, s); MS m/z (TS⁺) 366 (MNH₄⁺) |
| 99 | Prep 94 | Y=SMe, Z=Me | δ_H (CDCl₃, 400 MHz) 2.31 (3H, s), 2.43 (3H, s), 3.02 (3H, s), 6.61 (1H, s), 6.72 (1H, dd), 6.83 (1H, d), 6.88 (1H, s), 7.17 (1H, d), 7.37 (1H, dd), 7.55 (1H, s); MS m/z (TS⁺) 366 (MNH₄⁺) |

Preparation 100

N-{3-Cyano-4-[3-methyl-4-(methylsulfanyl)phenoxy]phenyl}-N-methylmethanesulfonamide

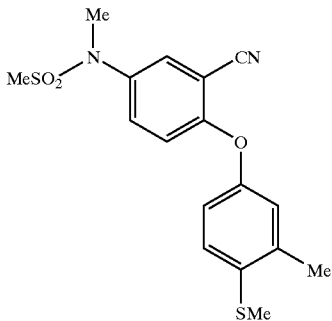

The title compound was prepared from the sulfonamide of Preparation 98 by the method of Preparation 88; $\delta_H$ (CDCl$_3$, 400 MHz) 2.31 (3H, s), 2.44 (3H, s), 2.83 (3H, s), 3.27 (3H, s), 6.79 (1H, d), 6.88 (2H, m), 7.17 (1H, d), 7.44 (1H, dd), 7.58 (1H, d); MS m/z (ES$^+$) 385 (MNa$^+$).

Preparation 101

1,3-Dihydro-2-benzothiophen-5-ol

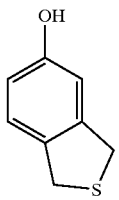

(i) Preparation of [4-(allyloxy)-2-(hydroxymethyl)phenyl]methanol

Dimethyl 4-(allyloxy)phthalate [prepared according to Inouye, M.; Tsuchiya, K.; Kitao, T. Angew. Chem. 1992, 104, 198–200 (See also Angew. Chem., Int. Ed. Engl, 1992, 204–205)] (9.9 g, 38 mmol) was dissolved in THF (40 mL) and cooled to 0° C. before the dropwise addition of lithium aluminium hydride (1M in THF, 77 mL, 77 mmol) over 10 min. The mixture was then allowed to stir at room temperature for 3 h before being quenched cautiously by the addition of water (1.4 mL) followed by 2M NaOH (1.4 mL). Excess MgSO$_4$ was then added followed by water until a granular precipitate formed (ca. 5 mL). The mixture was then filtered and evaporated to a brown oil (7.1 g, ca. 95%). $^1$H NMR showed the material to be of ca. 85% purity. It was used directly in the next stage without further purification; $\delta_H$ (CDCl$_3$, 400 MHz) 2.63 (1H, brs), 2.91 (1H, brs), 4.52 (2H, m), 4.67 (4H, m), 5.26 (1H, dd), 5.38 (1H, dd), 5.97–6.09 (1H, m), 6.80 (1H, dd), 6.92 (1H, d), 7.22 (1H, d).

(ii) Preparation of 5-(allyloxy)-1,3-dihydro-2-benzothiophene

Crude diol from stage (i) (3.5 g, 18 mmol) was dissolved in DCM (60 mL) and treated with Et$_3$N (10 mL, 72 mmol) and the solution was cooled to 0° C. Methanesulfonyl chloride (4.2 mL, 54 mmol) was added dropwise and the solution was stirred for 1 h being allowed to reach room temperature. The reaction was then quenched by the addition of water followed by 2M HCl (50 mL). The DCM layer was separated and the aqueous layer was re-extracted with DCM (50 mL). The combined organic fractions were washed with water (50 mL), dried (MgSO$_4$) and concentrated to a volume of ca. 30 mL. Benzyltriethylammonium chloride (1 g) was added followed by a solution of sodium sulfide (5 g, 91 mmol) in water (50 mL). The mixture was stirred rapidly under a nitrogen atmosphere for 15 h. The organic layer was separated and the aqueous layer was re-extracted with DCM (50 mL). The combined organic layers were dried (MgSO$_4$) and evaporated to a yellow oil. Flash chromatography afforded two fractions; the first was pure product and the second product contaminated with dimeric material. Trituration of the second fraction caused crystallisation of the dimeric material which was removed by filtration. The filtrate was combined with the first chromatography fraction to afford the desired product (800 mg, 23%); $\delta_H$ (CDCl$_3$, 400 MHz) 4.16 (2H, s), 4.19 (2H, s), 4.48 (2H, m), 5.26 (1H, d), 5.37 (1H, d), 5.95–6.06 (1H, m), 6.74 (2H, m), 7.09 (1H, d).

(iii) Preparation of 1,3-dihydro-2-benzothiophen-5-ol

The allyl ether from stage (ii) (800 mg, 4.16 mmol) was dissolved in THF (10 mL) and treated with palladium tetrakis(triphenylphosphine) (481 mg, 0.42 mmol) followed by sodium borohydride (944 mg, 25 mmol). The mixture was then heated to 45° C. and stirred at this temperature for 15 h. After cooling to room temperature the THF was evaporated and the residue partitioned between 2M NaOH solution (25 mL) and diethyl ether (25 mL). The aqueous layer was separated and the organic layer re-extracted with 2M NaOH solution (25 mL). The combined aqueous layers were neutralised to pH 7–8 with concentrated hydrochloric acid and extracted with EtOAc (2×25 mL). The combined organic extracts were dried (MgSO$_4$) and evaporated to a clear oil of the title phenol which solidified upon standing (540 mg, 85%); 4.14 (2H, s), 4.17 (2H, s), 6.63–6.68 (2H, m), 7.04 (1H, d).

Biological Activity

A number of compounds were tested for biological activity by their ability to inhibit the uptake of serotonin by human serotonin transporters as follows.

(i) Cell Culture

Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C. and 5% CO$_2$ in DMEM-culture media (supplemented with 10% dialysed foetal calf serum (FCS), 2mM l-glutamine and 250 μg/ml geneticin)). Cells were harvested for the assay to yield a cell suspension of 750,000 cells/ml.

(i) Determination of Inhibitor Potency

All test compounds were dissolved in 100% DMSO and diluted down in assay buffer to give appropriate test concentrations. Assays were carried out in 96-well filter bottom plates. Cells (7500 cells/assay well) were pre-incubated in standard assay buffer containing either test compound, standard inhibitor or compound vehicle (1% DMSO) for 5 minutes. Reactions were started by addition of either $^3$H-Serotonin, $^3$H-Noradrenaline or $^3$H-Dopamine substrates. All reactions were carried out at room temperature in a shaking incubator. Incubation times were 5 minutes for the hSERT and hDAT assays and 15 minutes for the hNET assay. Reactions were terminated by removal of the reaction mixture using a vacuum manifold followed by rapid washing with ice cold assay buffer. The quantity of $^3$H-substrate incorporated into the cells was then quantified.

Assay plates were dried in a microwave oven, scintillation fluid added, and radioactivity measured. Potency of test compounds was quantified as IC$_{50}$ values (concentration of test compound required to inhibit the specific uptake of radiolabelled substrate into the cells by 50%).

147

(iii) Standard Assay Buffer Composition
Trizma hydrochloride (26 mM)
NaCl (124 mM)
KCl (4.5 mM)
$KH_2PO_4$ (1.2 mM)
$MgCl_2.6H_2O$ (1.3 mM)
Ascorbic acid (1.136 mM)
Glucose (5.55 mM)
pH 7.40
$CaCl_2$ (2.8 mM)
Pargyline (100 $\mu$M)
Note: The pH of the buffer was adjusted to 7.40 with 1M NaOH before addition of $CaCl_2$ and pargyline.

(iv) Summary of Assay Parameters

|  | hSERT Assay | hDAT Assay | hNET Assay |
| --- | --- | --- | --- |
| Cell concentration per assay well. | 75,000 | 75,000 | 75,000 |
| Substrate Concentration. | $^3$H-5HT (50 nM) | $^3$H-Dopamine (200 nM) | $^3$H-Noradrenaline (200 nM) |
| Incubation time (minutes) | 5 | 5 | 15 |

Compounds having a serotonin re-uptake inhibition (SRI) $IC_{50}$ value of less than or equal to 100 nM include the title compounds of Examples 1–6, 8–23, 25, 26, 29–32, 34–36, 43, 45–49, 51, 56–102, 109–130.

Compounds having an serotonin re-uptake inhibition (SRI) $IC_{50}$ value of less than or equal to 100 nM and which are more than 10-fold as potent in the inhibition of serotonin re-uptake than in the inhibition of dopamine re-uptake or noradrenaline re-uptake include the title compounds of Examples 1–6, 9–13, 16–19, 21, 22, 25, 26, 29–32, 34–36, 43, 45, 47–49, 51, 57–88, 90–102, 109–121, 123, 124, 127, 129.

Compounds having an serotonin re-uptake inhibition (SRI) $IC_{50}$ value of less than or equal to 100 nM and which are more than 100-fold as potent in the inhibition of serotonin re-uptake than in the inhibition of dopamine re-uptake or noradrenaline re-uptake include the title compounds of Examples 1, 2, 4, 5, 9, 12, 13, 16–19, 21, 22, 25, 26, 29–32, 34–36, 43, 45, 48, 49, 58–80, 83–88, 90, 92–97, 99–102, 111–113, 115–118, 120, 123, 124, 127.

Compounds having an serotonin re-uptake inhibition (SRI) $IC_{50}$ value of less than or equal to 50 nM and which are more than 100-fold as potent in the inhibition of serotonin re-uptake than in the inhibition of dopamine re-uptake and noradrenaline re-uptake include the title compounds of Examples 1, 2, 4, 9, 12, 17, 18, 26, 29, 30, 36, 43, 45, 48, 49, 60–66, 68–75, 78, 79, 90, 92–94, 100, 102, 116, 118, 124.

In particular, the title compound of Example 16 had a serotonin re-uptake inhibition (SRI) $IC_{50}$ of 4.7 nM; the title compound of Example 29 had a serotonin re-uptake inhibition (SRI) $IC_{50}$ of 2.0 nM; and the title compound of Example 62 had a serotonin re-uptake inhibition (SRI) $IC_{50}$ of 3.7 nM.

What is claimed is:
1. A compound of general formula (I), pharmaceutically acceptable salts, or solvates or polymorphs thereof;

148

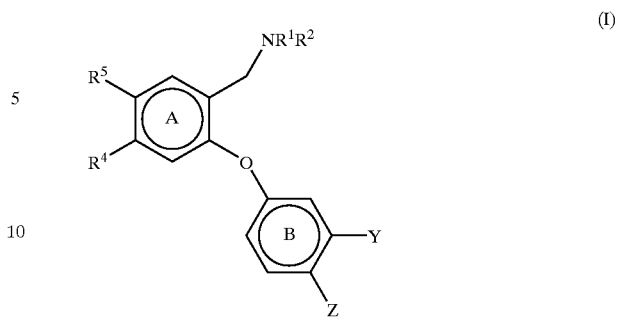

wherein;
$R^1$ and $R^2$, which may be the same or different, are H, $C_1$–$C_6$alkyl or $(CH_2)_d(C_3$–$C_6$cycloalkyl) wherein d=0, 1, 2 or 3; or $R^1$ and $R^2$ together with the nitrogen to which they are attached form an azetidine ring;
Z or Y is —$SR^3$ and other Z or Y is halogen or —$R^3$; wherein $R^3$ is independently $C_1$–$C_4$ alkyl optionally substituted with fluorine; except that $R^3$ is not $CF_3$;
$R^4$ and $R^5$, which may be the same or different, are:
A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$ alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F, OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or
a 5- or 6-membered heterocyclic ring containing 1, 2 or 3 heteroatoms selected from N, S and O, optionally substituted independently by one or more $R^{13}$;
wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)_2$.

2. A compound according to claim 1, pharmaceutically acceptable salts, solvates or polymorphs thereof, wherein $R^1$ and $R^2$, which may be the same or different, are hydrogen or $C_1$–$C_6$alkyl.

3. A compound according to claim 2, pharmaceutically acceptable salts, solvates or polymorphs thereof, wherein $R^1$ and $R^2$, which may be the same or different, are hydrogen or methyl.

4. A compound according to claims 1 or 2, pharmaceutically acceptable salts, solvates or polymorphs thereof, wherein when Z or Y is —$SR^3$, $R^3$ is methyl or ethyl.

5. A compound according to claim 1, pharmaceutically acceptable salts, solvates or polymorphs thereof, wherein $R^6$ and $R^7$, which may be the same or different, are hydrogen, $C_1$–$C_3$alkyl optionally substituted by hydroxy, —$CONH_2$ or $C_1$–$C_3$alkoxy.

6. A compound according to claim 1, pharmaceutically acceptable salts, solvates or polymorphs thereof, wherein $R^8$ is hydrogen, hydroxyethyl or methyl.

7. A compound according to claim 1, pharmaceutically acceptable salts, solvates or polymorphs thereof, wherein $R^9$ is methyl, ethyl, isopropyl, trifluoromethyl or methoxyethyl.

8. A compound according to claim 1, pharmaceutically acceptable salts, solvates or polymorphs thereof, wherein p is 1 or 0.

9. A compound according to claim 1, pharmaceutically acceptable salts, solvates or polymorphs thereof, wherein $R^4$ and $R^5$, which may be the same or different, are —$(CH_2)_p$—X, where p is 0, 1 or 2; X is hydrogen, hydroxy, $CONR^6R^7$, $SO_2NR^6R^7$, $NR^8SO_2R^9$, $SR^{10}$, $SOR^9$ or $SO_2R^{10}$ wherein $R^6$, $R^7$, $R^8$, $R^9$ and $R^{10}$ are as defined in claim 1, or
a 5- or 6-membered heterocyclic ring containing 1, 2 or 3 heteroatoms selected from N, S and O.

10. A compound according to claim 1, pharmaceutically acceptable salts, solvates or polymorphs thereof, wherein $R^4$ and $R^5$, which may be the same or different, are:
—$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen or $C_1$–$C_3$alkyl optionally substituted by hydroxy, —$CONH_2$ or $C_1$–$C_3$alkoxy (preferably methoxy); $R^8$ is hydrogen, hydroxyethyl or methyl; or $R^9$ is methyl, ethyl, isopropyl, trifluoromethyl or methoxyethyl; or triazolyl, imidazolyl or pyrazolyl.

11. A compound according to claim 1, pharmaceutically acceptable salts, solvates or polymorphs thereof, wherein $R^4$ and $R^5$ are not both hydrogen.

12. A compound according to claim 1, pharmaceutically acceptable salts, solvates or polymorphs thereof, wherein at least one of $R^4$ and $R^5$ is A—X, wherein X is $NR^6R^{11}$, $R^{11}$ is hydrogen or $C_{1-6}$ alkyl and A and $R^6$ are as defined in claim 1.

13. A compound according to claim 1, pharmaceutically acceptable salts, solvates or polymorphs thereof, wherein $R^4$ is hydrogen.

14. A compound according to claim 1, pharmaceutically acceptable salts, solvates or polymorphs thereof, wherein $R^6$ and $R^7$, which may be the same or different, are hydrogen, $C_1$–$C_3$alkyl optionally substituted by hydroxy, —$CONH_2$ or $C_1$–$C_3$alkoxy.

15. A compound according to claim 14, pharmaceutically acceptable salts, solvates or polymorphs thereof, wherein $R^6$ and $R^7$, which may be the same or different, are hydrogen or methyl.

16. A compound according to claim 14, pharmaceutically acceptable salts, solvates or polymorphs thereof, wherein $R^6$ and $R^7$ are hydrogen.

17. A compound according to claim 1, pharmaceutically acceptable salts, solvates or polymorphs thereof, wherein $R^6$ and $R^7$, together with the nitrogen to which they are attached, form a heterocyclic ring, selected from a pyrrolidine ring optionally substituted with OH or $CONH_2$, a piperidine ring optionally substituted with OH or $CONH_2$ and a morpholine ring optionally substituted with $CONH_2$.

18. A compound according to claim 1, pharmaceutically acceptable salts, solvates or polymorphs thereof, wherein at least one of $R^4$ and $R^5$ is A—X, wherein X is $CO_2R^{10}$, $SR^{10}$ or $SO_2R^{10}$, $R^{10}$ is independently for each occurrence methyl or ethyl and A is as defined in claim 1.

19. A compound according to claim 1, pharmaceutically acceptable salts, solvates or polymorphs thereof, wherein $R^1$ and $R^2$, which may be the same or different, are hydrogen or methyl,
Z or Y is —$SR^3$ and the other Z or Y is halogen or —$R^3$, wherein $R^3$ is methyl or ethyl and
$R^4$ and $R^5$, which may be the same or different, are $(CH_2)_p$—X or an oxadiazolyl, triazolyl, imidazolyl, oxazolyl, pyrazolyl, pyridinyl or pyrimidinyl group,
wherein:
p is 0 or 1; X is hydrogen, hydroxy, $CONR^6R^7$, $SO_2NR^6R^7$, $NR^8SO_2R^9$, $SR^{10}$, $SOR^9$ or $SO_2R^{10}$ and wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); or $R^6$ and $R^7$, together with the nitrogen to which they are attached, form a morpholine, pyrrolidine or piperidine ring each of which may be substituted by OH or $CONH_2$; $R^8$ is hydrogen, hydroxyethyl or methyl; $R^9$ is methyl, ethyl, isopropyl, trifluoromethyl or methoxyethyl; and $R^{10}$ is methyl or ethyl.

20. A compound according to claim 18, pharmaceutically acceptable salts, solvates or polymorphs thereof, wherein Z or Y is —$SR^3$ and the other Z or Y is halogen or —$R^3$, wherein $R^3$ is methyl or ethyl; and
$R^4$ and $R^5$, which may be the same or different, are —$(CH_2)_p$—X, triazolyl, imidazolyl or pyrazolyl,
wherein:
p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy; $R^8$ is hydrogen, hydroxyethyl or methyl; $R^9$ is methyl, ethyl, isopropyl, trifluoromethyl or methoxyethyl.

21. A compound according to claim 19, pharmaceutically acceptable salts, solvates or polymorphs thereof, wherein $R^4$ is hydrogen.

22. A compound according to claim 20, pharmaceutically acceptable salts, solvates or polymorphs thereof, with the proviso that $R^4$ and $R^5$ are not both hydrogen.

23. A compound according to claim 1, pharmaceutically acceptable salts, solvates or polymorphs thereof, selected from the group:
4-(2,3-dihydro-1-benzothien-5-yloxy)-3-[(methylamino)methyl]-benzenesulfonamide;
3-[(dimethylamino)methyl]-4-[3-methyl-4-(methylsulfanyl)phenoxy]-benzenesulfonamide;
4-(2,3-dihydro-1-benzothien-5-yloxy)-3-[(dimethylamino)methyl]-benzenesulfonamide;
4-[3-chloro-4-(methylsulfanyl)phenoxy]-3-[(dimethylamino)methyl]-benzenesulfonamide;
3-[(dimethylamino)methyl]-4-[3-fluoro-4-(methylsulfanyl)phenoxy]-benzenesulfonamide;
N,N-dimethyl-N-[2-(6-quinolinyloxy)benzyl]amine;
3-[(methylamino)methyl]-4-(6-quinolinyloxy)benzenesulfonamide;
4-(2,3-dihydro-1-benzothien-5-yloxy)-3-[(methylamino)methyl]benzamide;
4-(2,3-dihydro-1-benzothien-5-yloxy)-N-methyl-3-[(methylamino)methyl]-benzamide;
N-{3-[(methylamino)methyl]4-[3-methyl-4-(methylsulfanyl)phenoxy]benzyl}methanesulfonamide;
3-[(methylamino)methyl]-4-[3-methyl-4-(methylsulfanyl)phenoxy]benzamide;
4-(2,3-dihydro-1,4-benzoxathiin-7-yloxy)-3-[(dimethylamino)methyl]benzamide;
{3-[(dimethylamino)methyl]-4-[3-fluoro-4-(methylsulfanyl)phenoxy]phenyl}-methanol;
3-[(dimethylamino)methyl]-4-(6-quinolinyloxy)benzamide;
3-[(methylamino)methyl]-4-(6-quinolinyloxy)benzamide;
N-methyl-N-{3-[(methylamino)methyl]-4-[3-methyl-4-(methylsulfanyl)phenoxy]-phenyl}methanesulfonamide and
N-{4-(2,3-dihydro-1,4-benzoxathiin-7-yloxy)-3-[(dimethylamino)methyl]phenyl}-methanesulfonamide.

24. A pharmaceutical composition comprising a compound as defined in claim 1, or pharmaceutically acceptable salts, solvates or polymorphs thereof, and a pharmaceutically acceptable adjuvant, diluent or carrier.

25. A method of treatment or prevention of premature ejaculation, comprising the administration of an effective amount of a compound as defined in claim 1, pharmaceutically acceptable salts, solvates or polymorphs thereof, to a patient in need of such treatment or prevention.

26. A method of increasing ejaculatory latency which comprises the administration of an effective amount of a compound as defined in claim 1, pharmaceutically acceptable salts, solvates or polymorphs thereof, to a male desiring increased ejaculatory latency.

27. A process for the preparation of a compound of general formula (I);

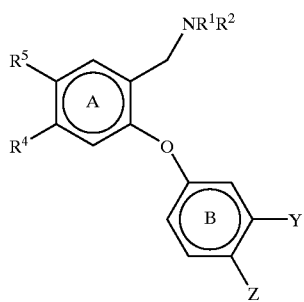

(I)

wherein $R^1$, $R^2$, $R^4$, $R^5$, X and Z are as defined in claim 1 comprising reacting a compound of general formula Ia

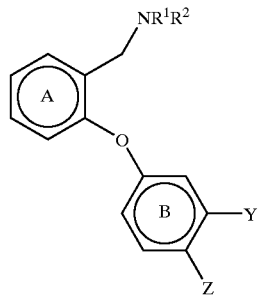

(Ia)

under suitable reaction conditions to form the compound of formula I, wherein the suitable reaction conditions are:

i) where $R^4/R^5$ are halogen, by reaction of (Ia) with a suitable halogenating agent in an inert solvent which does not adversely affect the reaction;

ii) where $R^4/R^5$ are —$NO_2$, by reaction of (Ia) with a suitable nitrating agent in an inert solvent which does not adversely affect the reaction at, or below, room temperature; or ii) where $R^4/R^5$ is —$SO_2NR^6R^7$ by reaction of an intermediate sulfonyl chloride with the requisite amine of formula $HNR^6R^7$ in a suitable solvent.

28. A process according to claim 27 for preparing a compound of formula (Iq),

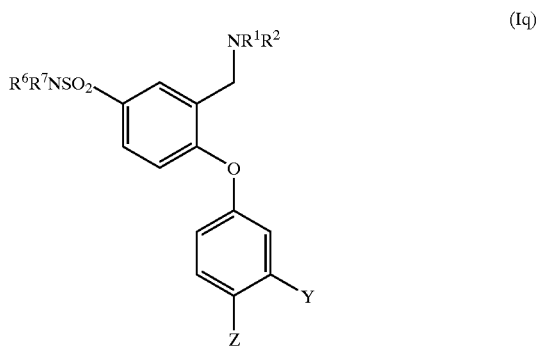

(Iq)

comprising a) reacting a compound of formula Ia, optionally in a suitable solvent, with chlorosulfonic acid to give a compound of formula XVIII

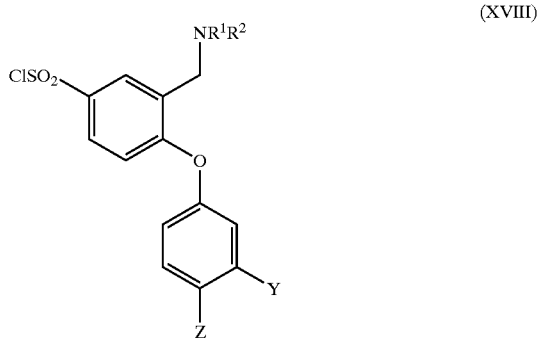

(XVIII)

followed by b) reacting with $HNR^6R^7$ to give the compound of formula (Iq).

29. A process according to claim 28 wherein the compound of formula XVIII is generated in situ and reacted with $HNR^6R^7$ without isolation.

30. A process according to claim 27, 28 or 29 which further comprises the step of preparing compounds of formula (Ia), by reacting compounds of formula (IIa)

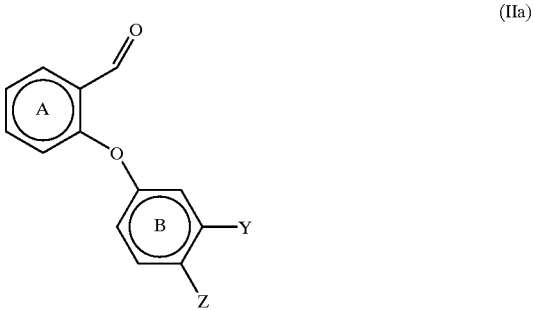

(IIa)

with a compound of formula $HNR^1R^2$, or with a suitable salt form thereof, together with a hydride reducing agent in a suitable solvent, to form the compound of formula (Ia).

31. An intermediate compound of formula (XVIII) as defined in claims 28 or 29.

32. An intermediate compound of formula (IIa) as defined in claim 30.

33. A process for preparing a compound of formula I

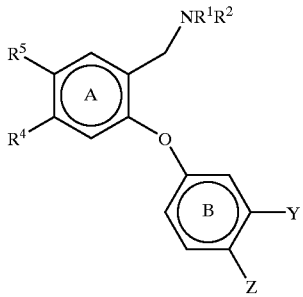
(I)

wherein $R^1$, $R^2$, $R^4$, $R^5$, X and Z are as defined in claim 1, comprising reacting a compound of formula II

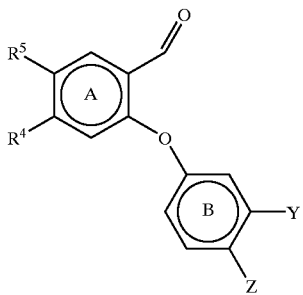
(II)

with a compound of formula $HNR^1R^2$ or with a suitable salt form thereof, together with a hydride reducing agent in a suitable solvent.

34. A process according to claim 33 which further comprises coupling under suitable reaction conditions a compound of formula III,

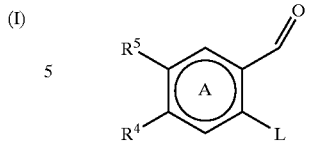
(III)

wherein L is a suitable leaving group such as halogen or a sulfonate ester such as trifluoromethanesulfonate or methanesulfonate, with a compound of formula IV

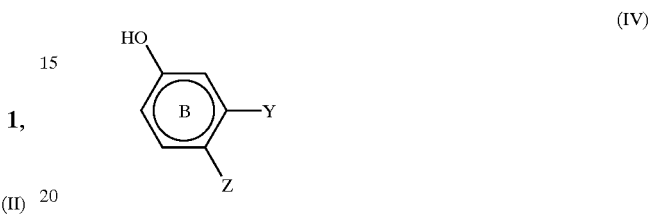
(IV)

to give the compound of formula II.

35. An intermediate compound of formula II as defined in claim 33.

36. A compound of general formula (I), or pharmaceutically acceptable salts, solvates or polymorphs thereof, wherein $R^1$, $R^2$, Y and Z are as defined in claim 1; and $R^4$ and $R^5$, which may be the same or different, are —$(CH_2)_p$—A', wherein p is 0, 1 or 2 and A' is a polar group.

37. A compound according to claim 36, wherein the polar group has a δ-value more negative than −0.1.

38. A compound comprising 3-[(methylamino)methyl]-4-[3-methyl-4-methylsulfanyl)phenoxy]-benzenesulfonamide or 3-[(dimethylamino)methyl]-4-[3-methyl-4-(methylsulfanyl)phenoxy]-benzenesulfonamide, pharmaceutically acceptable salts, or solvates or polymorphs thereof.

39. A compound as recited claim 1 wherein $R^1$ and $R^2$ are methyl, $R^4$ is H, $R^5$ is —$SO_2NR^6R^7$ where $R^6$ and $R^7$ are H, Y is $R^3$ and Z is $SR^3$ wherein $R^3$ is methyl, pharmaceutically acceptable salts, or solvates or polymorphs thereof.

* * * * *